(12) United States Patent
Hayamizu et al.

(10) Patent No.: US 12,204,744 B2
(45) Date of Patent: *Jan. 21, 2025

(54) ENDOSCOPE PROCESSOR, PROGRAM, AND INFORMATION PROCESSING METHOD

(71) Applicant: HOYA CORPORATION, Tokyo (JP)

(72) Inventors: Eiji Hayamizu, Tokyo (JP); Katsuya Tannai, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/404,072

(22) Filed: Jan. 4, 2024

(65) Prior Publication Data
US 2024/0143155 A1 May 2, 2024

Related U.S. Application Data

(63) Continuation of application No. 17/610,948, filed as application No. PCT/JP2020/019280 on May 14, 2020, now Pat. No. 11,966,574.
(Continued)

(51) Int. Cl.
G06F 3/048 (2013.01)
A61B 1/00 (2006.01)
(Continued)

(52) U.S. Cl.
CPC ...... G06F 3/04847 (2013.01); A61B 1/00006 (2013.01); A61B 1/0004 (2022.02);
(Continued)

(58) Field of Classification Search
CPC .. G06F 3/04847; G06F 3/0482; G06F 3/0488; G06F 3/04886; G06F 3/041;
(Continued)

(56) References Cited

U.S. PATENT DOCUMENTS

2003/0093503 A1 5/2003 Yamaki et al.
2004/0124791 A1 7/2004 Takahashi
(Continued)

FOREIGN PATENT DOCUMENTS

JP 2003-126032 5/2003
JP 2006-075240 3/2006
(Continued)

OTHER PUBLICATIONS

Japanese Examiner's Reconsideration Report dated Dec. 11, 2023 in corresponding Japanese Application No. 2021-519478 and machine translation thereof.
(Continued)

Primary Examiner — Aleksey Olshannikov
(74) Attorney, Agent, or Firm — GREENBLUM & BERNSTEIN, P.L.C.

(57) ABSTRACT

An endoscope processor includes a processor executing program code to a) display on a touch panel a setting region combining an on-off switch accepting switching between on and off states of a function of an endoscope and an adjustment switch accepting adjustment of a level of the function; b) accept operations performed on the switches that are displayed; and c) change a state of the function based on an accepted operation. The adjustment switch includes a range display indicating an adjustable range and a slider movable along the range display. The accepting operation accepts a tap operation performed around the range display at a position away from the slider. In addition, the slider moves by a predetermined amount causing a predetermined amount of change in the level of the function of the endoscope in response to the tap operation performed at a location spaced from the range display.

1 Claim, 54 Drawing Sheets

Related U.S. Application Data

(60) Provisional application No. 62/848,743, filed on May 16, 2019.

(51) Int. Cl.
*G06F 3/0482* (2013.01)
*G06F 3/04847* (2022.01)
*G06F 3/0488* (2022.01)
*G06F 3/04886* (2022.01)
*A61B 1/015* (2006.01)
*A61B 1/06* (2006.01)

(52) U.S. Cl.
CPC ........ *A61B 1/00045* (2013.01); *G06F 3/0482* (2013.01); *G06F 3/0488* (2013.01); *G06F 3/04886* (2013.01); *A61B 1/015* (2013.01); *A61B 1/0655* (2022.02)

(58) Field of Classification Search
CPC .............. A61B 1/00006; A61B 1/0004; A61B 1/00045; A61B 1/015; A61B 1/0655; A61B 1/0002; A61B 1/05; A61B 1/0676; A61B 1/0684; A61B 1/00009; A61B 1/00004; A61B 1/00039; A61B 1/00043; A61B 1/00048; A61B 1/04
See application file for complete search history.

(56) References Cited

U.S. PATENT DOCUMENTS

| | | |
|---|---|---|
| 2005/0097191 A1 | 5/2005 | Yamaki et al. |
| 2007/0088193 A1 | 4/2007 | Omori et al. |
| 2013/0077119 A1 | 3/2013 | Arai |
| 2015/0227303 A1 | 8/2015 | Sudo et al. |
| 2016/0262600 A1 | 9/2016 | Yamaoka |
| 2018/0184881 A1 | 7/2018 | Urasaki et al. |
| 2019/0183591 A1 | 6/2019 | Johnson et al. |
| 2021/0038340 A1 | 2/2021 | Itkowitz et al. |

FOREIGN PATENT DOCUMENTS

| | | |
|---|---|---|
| JP | 2006-174882 | 7/2006 |
| JP | 2006-341104 | 12/2006 |
| JP | 2009-037344 | 2/2009 |
| JP | 2013-84256 | 5/2013 |
| JP | 2019-058528 | 4/2019 |
| WO | 2015/098229 | 7/2015 |
| WO | 2019/083805 | 5/2019 |

OTHER PUBLICATIONS

Japanese Official Notice mailed Dec. 19, 2023 in corresponding Japanese Patent Application No. 2021-519478 (notifying that the case will be transferred to the collegiate) and machine translation thereof.
May 17, 2023 Chinese Office Action in Chinese Application No. 202080036164.3.
Jan. 11, 2023 Extended European Search Report in corresponding European Application No. 20805411.4 and translation thereof.
Jun. 9, 2023 Extended European Search Report in corresponding European Application No. 20805696.0 and translation thereof.
International Search Report issued in International Patent Application No. PCT/JP2020/019280, dated Jul. 14, 2020 and English translation thereof.

| USER No. | USER NAME | PROFILE |
|---|---|---|
| 01 | Hxxx | S001 |
| 02 | Ixxxx | S002 |
| 03 | Jxxxx | S003 |
| 04 | Kxxxx | S004 |

| PURPOSE No. | PURPOSE | PROFILE |
|---|---|---|
| 01 | UPPER REGION OBSERVATION | S001 |
| 02 | UPPER REGION CLOSE EXAMINATION | S002 |
| 03 | ERCP | S003 |
| 04 | EMR | S004 |

| ORDER | PATIENT ID | NAME | AGE | SEX | NOTE | COMPLETE |
|---|---|---|---|---|---|---|
| 1 | Z01 | Axxxx Axxxxxx | 42 | M | | Y |
| 2 | A10 | Bx Bxxxxx | 39 | M | | N |
| 3 | R02 | Cxxxx Cxx | 28 | F | | N |
| 4 | B97 | Dxx Dxxxxxx | 59 | M | | N |

FIG. 16

| | △No. | ▽ID | △Name | |
|---|---|---|---|---|
| ● | 01 | Z01 | Axxxx Axxxxxx | > |
| ○ | 02 | A10 | Bx Bxxxxx | > |
| ○ | 03 | R02 | Cxxxx Cxx | > |
| ○ | 04 | B97 | Dxx Dxxxxxxx | > |

Patient

FIG. 17

|  | △No. | ▲ID | △Name |  |
|---|---|---|---|---|
| ○ | 02 | A10 | Bx Bxxxxx | > |
| ○ | 04 | B97 | Dxx Dxxxxxxx | > |
| ○ | 03 | R02 | Cxxxx Cxx | > |
| ● | 01 | Z01 | Axxxx Axxxxxx | > |

Patient

FIG. 18

|  | ▼No. | △ID | △Name |  |
|---|---|---|---|---|
| ○ | 04 | B97 | Dxx Dxxxxxxx | > |
| ○ | 03 | R02 | Cxxxx Cxx | > |
| ○ | 02 | A10 | Bx Bxxxxx | > |
| ● | 01 | Z01 | Axxxx Axxxxxx | > |

Patient

ENDOSCOPE PROCESSOR, PROGRAM, AND INFORMATION PROCESSING METHOD

CROSS-REFERENCE TO RELATED APPLICATIONS

This is a continuation of U.S. patent application Ser. No. 17/610,948, filed Nov. 12, 2021, which is a U.S. National Phase Appl. of International Pat. Appl. No. PCT/JP2020/019280, filed May 14, 2020, and claims benefit of U.S. Provisional Appl. No. 62/848,743, filed May 16, 2019. The entire disclosure of each of the above-identified documents, including the specification, drawings, and claims, is incorporated herein by reference in its entirety.

TECHNICAL FIELD

The present invention relates to an endoscope processor, a program, and an information processing method.

BACKGROUND ART

An endoscope processor that accepts an operation of a lamp or a pump via a touch panel has been proposed (Patent Document 1).

PRIOR ART DOCUMENT

Patent Document

[Patent Document 1] Japanese Patent Application Laid-Open No. 2019-58528

SUMMARY OF THE INVENTION

Problems to be Solved by Invention

In the endoscope processor disclosed in Patent Document 1, an operation of turning on and off of the functions of a lamp, a pump and the like in the event of emergency can promptly be performed. During endoscopy, however, it is difficult for the user to promptly adjust these functions.

According to an aspect, an object is to provide an endoscope processor capable of promptly adjusting the functions.

Means for Solving Problems

An endoscope processor, comprises: a setting region display unit that displays on a touch panel a setting region where an on-off switch accepting switching between an on state and an off state of a function of an endoscope is combined with an adjustment switch accepting adjustment of a level of the function; an operation acceptance unit that accepts operations performed on the on-off switch and the adjustment switch that are displayed; and a change control unit that changes an operating state of the function based on an accepted operation.

Effects of Invention

According to an aspect, it is possible to provide the endoscope processor capable of promptly adjusting the functions.

BRIEF DESCRIPTION OF DRAWINGS

FIG. 5 illustrates the record layout of a profile DB.
FIG. 6 illustrates the record layout of the profile DB as a modification.
FIG. 7 illustrates the record layout of a patient DB.
FIG. 16 illustrates a patient list screen.
FIG. 17 illustrates sorting of a patient list.
FIG. 18 illustrates sorting of the patient list.

MODE FOR CARRYING OUT INVENTION

Embodiment 1

Figure 1:
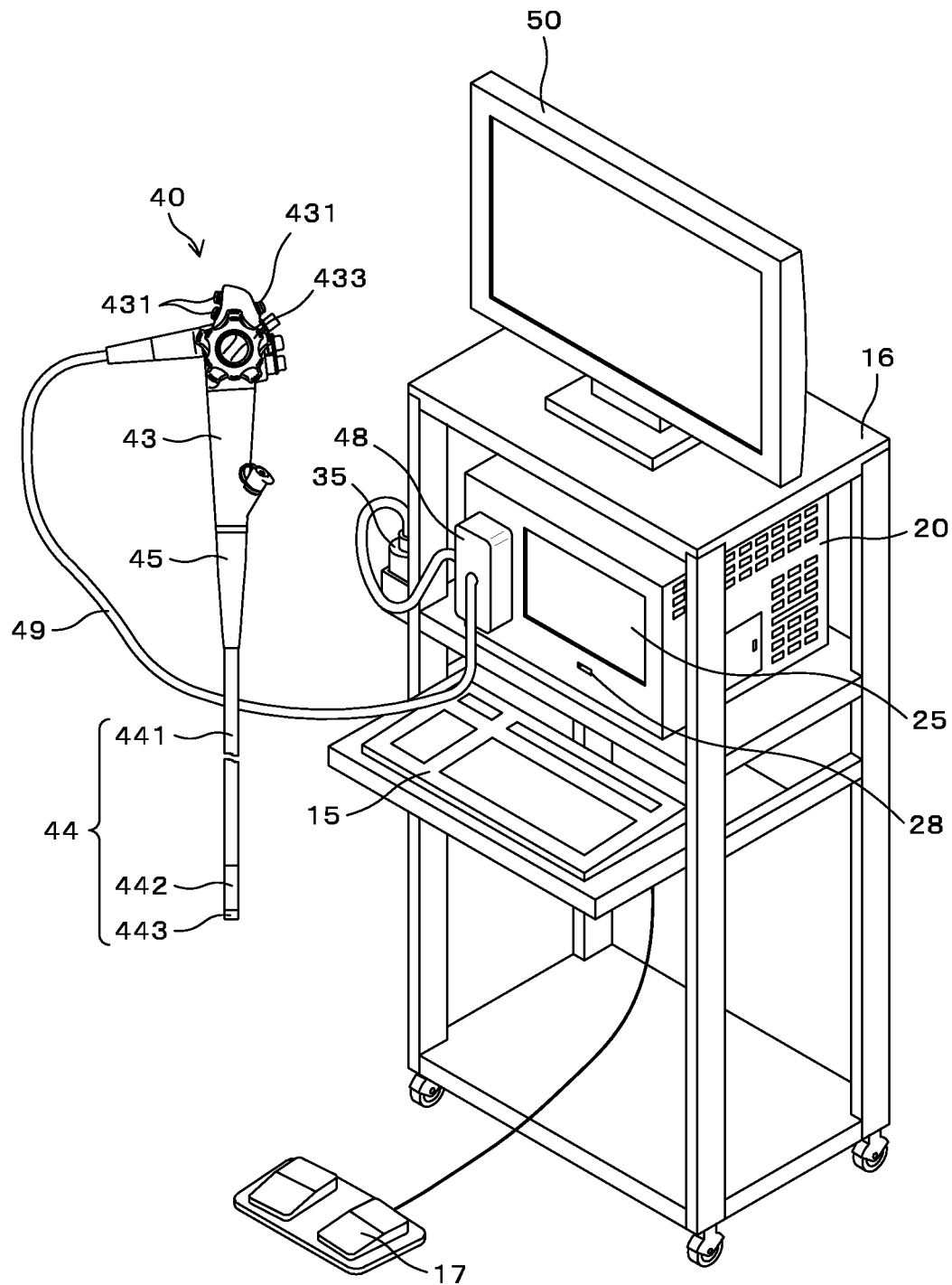
FIG. 1 illustrates an external appearance of an endoscope system.

FIG. 1 illustrates an external appearance of an endoscope system 10. The endoscope system 10 includes an endoscope processor 20, an endoscope 40 and a display device 50. The display device 50 is a display device such as a liquid crystal display or an organic electro luminescence (EL) display, for example.

The display device 50 is installed on the upper section of a storage rack with casters 16. The endoscope processor 20 is stored at the middle section of the storage rack 16. The storage rack 16 is located near a bed for endoscopy (not illustrated). The storage rack 16 contains a slide-out drawer mounted with a keyboard 15 connected to the endoscope processor 20. A foot switch 17 connected to the endoscope processor 20 is placed on the floor.

The endoscope processor 20 has a shape of a substantially parallelepiped and has one surface provided with a touch panel 25. Below the touch panel 25, a reading part 28 is located. The reading part 28 is an interface for connection, which is a universal serial bus (USB) connector, a secure digital (SD) card slot, a compact disc read only memory (CD-ROM) drive or the like, to perform reading and writing from/to a portable recording medium. Note that the touch panel 25 may be a device separate from the endoscope processor 20.

The endoscope 40 has an insertion part 44, an operation part 43, a universal cord 49 and a scope connector 48. The operation part 43 is provided with control buttons 431. The insertion part 44 is long and has one end connected to the operation part 43 through a bending proof portion 45. The insertion part 44 has, from the operation part 43 side, a flexible portion 441, a bending portion 442 and a head portion 443. The bending portion 442 bends in response to the operation of a bending knob 433.

The universal cord 49 is long and has one end connected to the operation part 43 and the other end connected to the scope connector 48. The universal cord 49 is flexible. The scope connector 48 has a substantially parallelepiped shape. The scope connector 48 is attached with an air/water supply port 36 (see FIG. 2) to which an air/water supply tube is connected.

Figure 2:
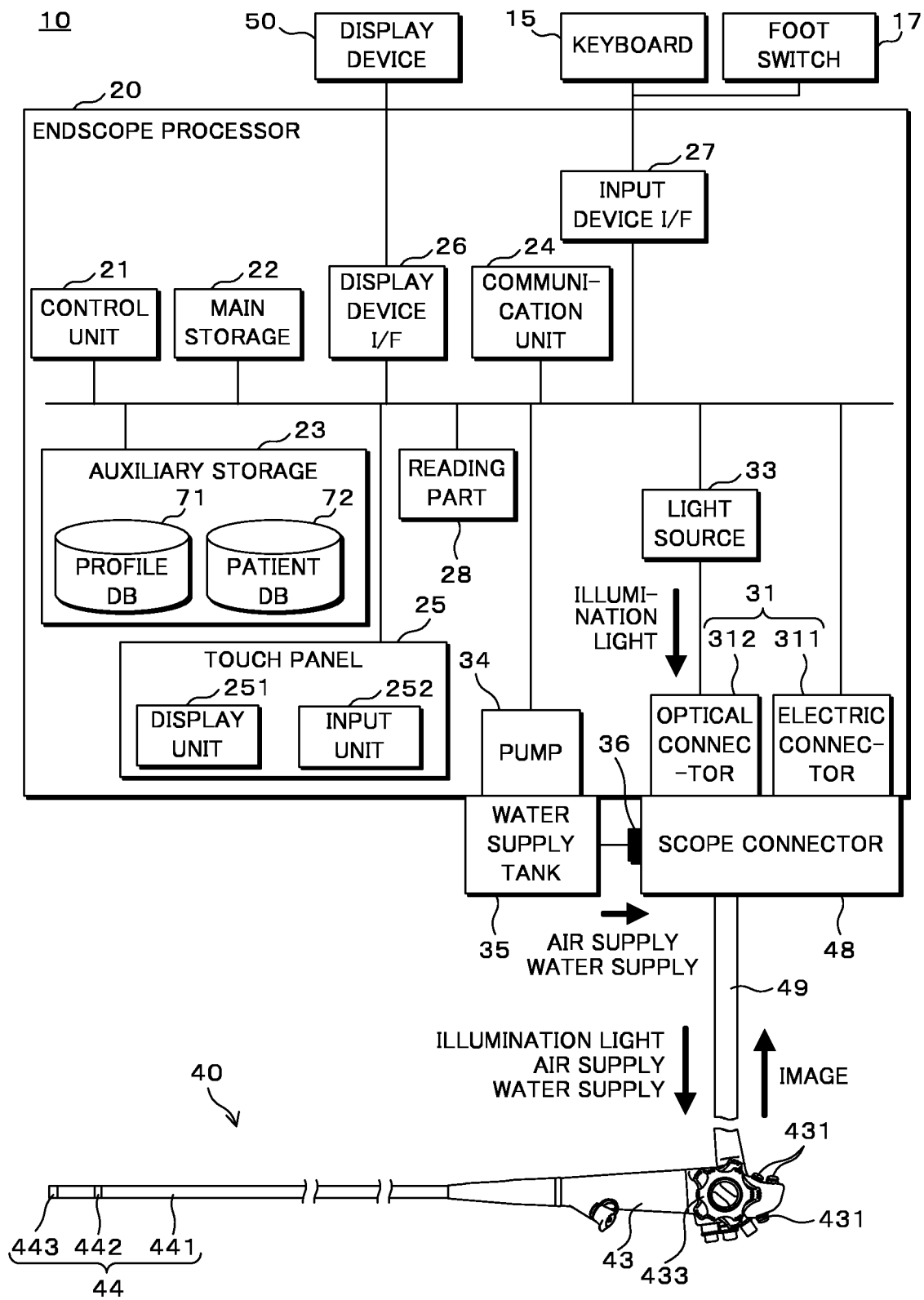
FIG. 2 illustrates the configuration of the endoscope system.

FIG. 2 illustrates the configuration of the endoscope system 10. As described above, the endoscope system 10 includes the endoscope processor 20, the endoscope 40 and the display device 50. The endoscope processor 20 is provided with a control unit 21, a main storage 22, an auxiliary storage 23, a communication unit 24, a display device interface (I/F) 26, an input device I/F 27, an endoscope connector 31, a light source 33, a pump 34 and buses in addition to the touch panel 25 and the reading part 28. The endoscope connector 31 includes an electric connector 311 and an optical connector 312.

The control unit 21 is an arithmetic control device that executes a program of the present embodiment. The control unit 21 employs one more central processing units (CPUs), a multi-core CPU or the like. The control unit 21 is connected to the hardware components forming of the endoscope processor 20 via the buses.

The main storage 22 is a storage such as a static random access memory (SRAM), a dynamic random access memory (DRAM), a flash memory or the like. The main storage 22 temporarily stores information needed in the course of the processing performed by the control unit 21 and a program that is being executed by the control unit 21.

The auxiliary storage 23 is a storage such as an SRAM, a flash memory, a hard disk or the like. The auxiliary storage 23 stores a profile database (DB) 71, a patient DB 72, a program to be executed by the control unit 21 and various data needed for execution of the program. It is noted that the profile DB 71 and the patient DB 72 may be stored in an external large-capacity storage device connected to the endoscope processor 20.

The communication unit 24 is an interface for performing data communication between the endoscope processor 20 and a network. The touch panel 25 includes a display unit 251 such as a liquid crystal display panel or the like and an input unit 252 overlaid on the display unit 251.

The display device I/F 26 is an interface to make connection between the endoscope processor 20 and the display device 50. The input device I/F 27 is an interface to make connection between the endoscope processor 20 and an input device such as the keyboard 15, the foot switch 17 or the like.

The light source 33 is a high-intensity white light source such as a xenon lamp, a light emitting diode (LED) or the like. The light source 33 is connected to the bus via a driver (not illustrated). The lighting or light-out and changes in brightness of the light source 33 are controlled by the control unit 21. The illumination light emitted from the light source 33 is incident on the optical connector 312. The optical connector 312 is engaged with the scope connector 48 to supply the endoscope 40 with illumination light.

The pump 34 generates pressures to be used for an air supply function and a water supply function of the endoscope 40. In the following description, the air supply function and the water supply function may sometimes collectively be described as an air/water supply function. The pump 34 is connected to the bus via a driver (not illustrated). The turning on or off and changes in pressure of the pump 34 are controlled by the control unit 21. The pump 34 is connected to the air/water supply port 36 attached to the scope connector 48 via a water supply tank 35.

The outline of the function of the endoscope 40 connected to the endoscope processor 20 is described. A fiber bundle, a cable bundle, an air supply tube, a water supply tube and the like are inserted inside the scope connector 48, the universal cord 49, the operation part 43 and the insertion part 44. The illumination light having been emitted from the light source 33 is emitted through the optical connector 312 and the fiber bundle from an illumination window provided at the head portion 443.

A range illuminated by the illumination light is captured by an imaging element provided at the head portion 443. A captured image is transmitted from the imaging element through the cable bundle and the electric connector 311 to the endoscope processor 20. The control unit 21 performs image processing on the captured image to generate an endoscopic image that allows the user to visually find a lesion. The control unit 21 outputs the endoscopic image to the display device 50.

Figure 3:
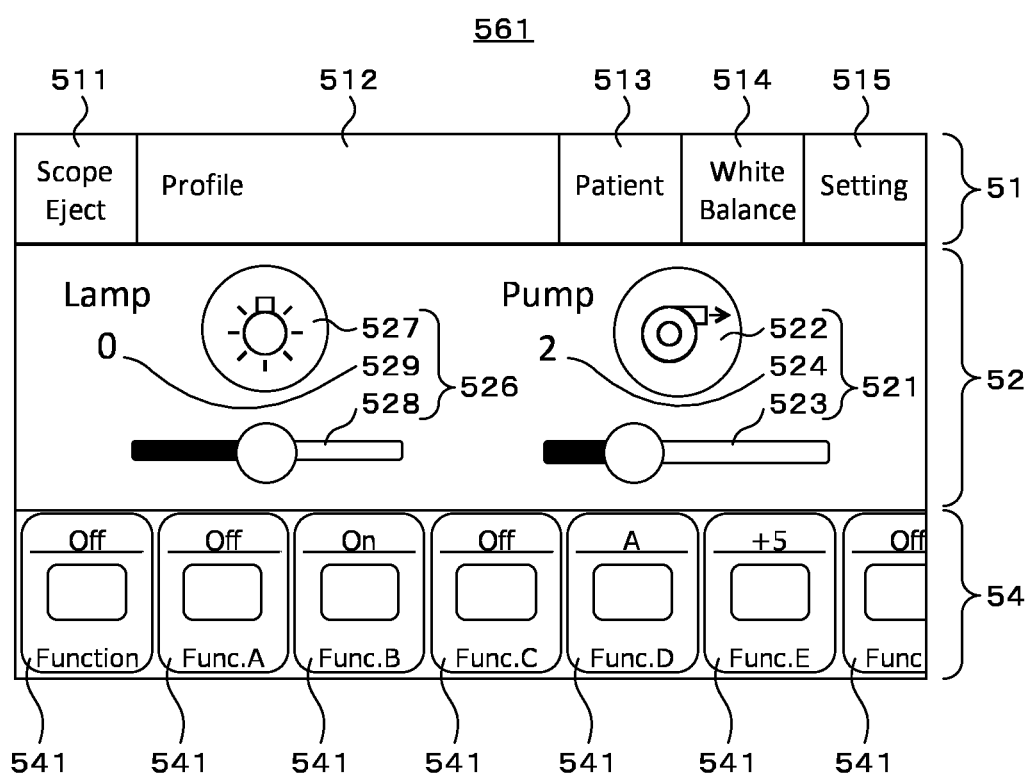
FIG. 3 is a display example of a top screen displayed on a touch panel.

FIG. 3 is an example of a top screen 561 to be displayed on the touch panel 25. During endoscopy, a user such as a doctor, a nurse or the like mainly uses the top screen 561. The top screen 561 includes a menu region 51, an operation region 52 and a custom button region 54. The top screen 561 is one example of an operation screen for accepting an operation by the user.

The control unit 21 functions as an operation screen display unit that displays an operation screen on the touch panel 25. According to the screen described with reference to FIG. 3, the control unit 21 further functions as a patient button display unit and a setting button display unit.

The menu region 51 is displayed at the upper part of the top screen 561. The menu region 51 includes a scope eject button 511, a profile button 512, a patient button 513, a white balance button 514 and a setting button 515. The operation region 52 includes a pump setting region 521 and a lamp setting region 526.

The custom button region 54 is located along the bottom side of the touch panel 25. In the custom button region 54, multiple custom buttons 541 are displayed in a row. If many custom buttons 541 are displayed at the custom button region 54, the user can horizontally scroll the custom button region 54 by a sliding operation of sliding the finger from side to side in the direction of alignment of the custom buttons 541 within the custom button region 54. The details of the custom buttons 541 and the custom button region 54 will be described later.

When ejecting the endoscope 40 from the endoscope processor 20, the user selects the scope eject button 511. The control unit 21 stops the operation of the light source 33 and the pump 34 as well as power supply to the imaging element to allow the endoscope 40 to be ready to be safely removable from the endoscope processor 20. The control unit 21 accepts a selection of the scope eject button 511 when the user performs a long-tap operation where the user continues to touch the scope eject button 511 for several seconds, for example.

The white balance button 514 is used when white balance is adjusted. Since the white balance adjustment has conventionally been conducted, description thereof is not repeated. The operation of the endoscope processor 20 when the profile button 512, the patient button 513 or the setting button 515 is selected as well as the operation region 52 will be described below.

Figure 4:
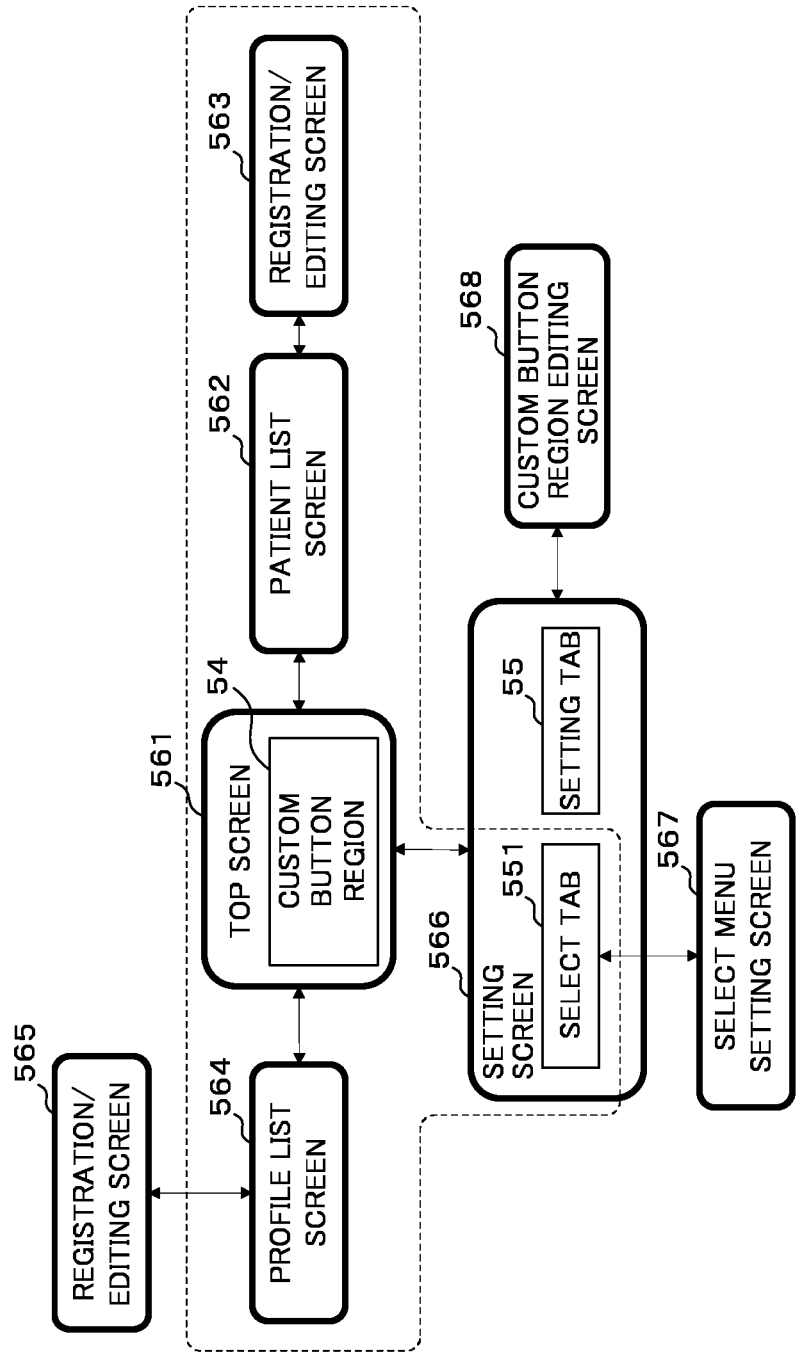
FIG. 4 illustrates a screen shift to be displayed on the touch panel.

FIG. 4 illustrates a screen shift of screens to be displayed on the touch panel 25. The top screen 561 described with reference to FIG. 3 includes the custom button region 54 as described above. If accepting a selection of the patient button 513, the control unit 21 shifts the screen to a patient list screen 562. As such, the control unit 21 functions as a patient list display unit and a custom button region display unit according to the present embodiment.

The control unit 21 shifts the screen from the patient list screen 562 to a patient list registering and editing screen 563 in response to an operation by the user. Examples of the patient list screen 562 and the registering and editing screen 563 will be described later.

If accepting a selection of the profile button 512, the control unit 21 shifts the screen to a profile list screen 564. The control unit 21 shifts the screen from the profile list screen 564 to a profile list registering and editing screen 565 in response to an operation by the user. Example of the profile list screen 564 and a profile list will be described later.

If accepting a selection of the setting button 515, the control unit 21 shifts the screen to a setting screen 566. The setting screen 566 includes a select tab 551 and a setting tab 55. The control unit 21 displays the setting screen 566 with the select tab 551 selected.

The control unit 21 switches settable items to be displayed on the setting screen 566 based on the tab selected by the user. The example of the setting screen 566 will be described later. The setting screen 566 with the select tab 551 selected may sometimes be described as a select menu screen in the description below.

If accepting a selection of a custom region setting button 542 (see FIG. 24) from the user during the display of the setting screen 566, the control unit 21 shifts the screen to a custom button region editing screen 568. An example of the custom button region editing screen 568 will be described later.

In response to the user performing a long-tap operation or the like during the display of the select menu screen, the control unit 21 switches the screen to the select menu setting screen 567. The user can change the setting of the select menu screen by using the select menu setting screen 567.

On the screens other than the top screen 561, a home button 555 (see FIG. 16) is arranged. If accepting a selection of the home button 555 by the user, the control unit 21 switches the screen to the top screen 561.

The screens to be used by the user during the preparation for endoscopy is mainly a part encircled by a broken line in FIG. 4. The screen to be used by the user during endoscopy is mainly the top screen 561. Note that the user suitably operates a screen other than the above-described screens as necessary.

By having appropriately set the custom button region 54 using the custom button region editing screen 568, the user can easily operate the endoscope processor 20 during endoscopy. By having appropriately set the settable items displayed on the select menu screen using the select menu setting screen 567, the user can easily operate the endoscope processor 20 during the preparation for endoscopy.

FIG. 5 illustrates the record layout of the profile DB 71. The profile DB 71 is a DB recording a user ID uniquely given to the user such as a doctor or the like, a user name, a profile related to a setting state of the endoscope processor 20 associated with one another. The profile includes the setting of the custom button region 54, the setting of the select tab 551, the setting of the initial state of the endoscope processor 20 and the like. The setting of the initial state of the endoscope processor 20 includes settings of, for example, a pressure of the pump 34, brightness of the light source 33 and an image quality adjustment function such as a contrast, and the like.

The profile DB 71 includes a user number (No.) field, a user name filed and a profile field. In the user number field, a user ID uniquely given to the user such as a doctor or the like is recorded. In the user name filed, a name of the user such as a doctor or the like is recorded. In the profile field, a profile including the setting states of the custom button region 54 and the select tab 551 as well as the initial setting state of the endoscope processor 20 is recorded.

The user selects a user name recorded in the user name filed of the profile DB 71 using the profile list screen 564 described later. The control unit 21 sets the custom button region 54 and the select tab 551 as well as the initial state of the endoscope processor 20 based on the profile read from the profile DB 71. The individual users can use the endoscope processor 20 in a user friendly setting.

The profile DB 71 may register records corresponding to multiple users for each department to which the users belong, for each type of occupation or the like. Multiple users can use the endoscope processor 20 under the common setting.

FIG. 6 illustrates the record layout of the profile DB 71 as a modification. The profile DB 71 shown in FIG. 6 includes a purpose number field, a purpose field and a profile field. In the purpose number field, a purpose number uniquely given for each intended purpose of the endoscope 40 is recorded.

In the purpose field, the purpose aimed by the technique performed using an endoscope is recorded such as "upper region observation," "upper region close examination," "endoscopic retrograde cholangiopancreatography" (ERCP) and "endoscopic mucosal resection (EMR)." In the profile field, the profile such as the setting states of the custom button region 54 and the select tab 551 as well as setting of the initial state of the endoscope processor 20 is recorded.

The user selects a purpose of endoscopy recorded in the purpose filed of the profile DB 71 using the profile list screen 564 described later. The control unit 21 sets the custom button region 54 and the select tab 551 as well as the initial state of the endoscope processor 20 based on the profile read from the profile DB 71. The user can use the endoscope processor 20 at settings suitable for the technique that is to be performed.

In the profile DB 71, records for each model of the endoscope 40, for example, may be recorded. In the profile DB 71, records for each region of the body that takes endoscopy may be recorded. The region of the body that undergoes endoscopy may be identified based on the model of the endoscope 40 connected to the endoscope processor 20. In the profile DB 71, a record corresponding to the combination between the intended purpose of the endoscope 40 and the user may have been recorded.

FIG. 7 illustrates the record layout of the patient DB 72. The patient DB 72 is a DB for recording information on patients who are scheduled to take endoscopy on that day. The patient DB 72 includes an order field, a patient ID field, a name field, an age field, a sex field, a note field and a complete field.

In the order field, the order in which endoscopy is scheduled to be performed is recorded. In the patient ID field, a patient ID uniquely given to the patient is recorded. In the name field, a name of the patient is recorded. In the age field, an age of the patient is recorded. In the sex field, a sex of the patient is recorded. In the sex field, "M" means a male and "F" means a female.

In the note field, a comment is recorded in text format. In the case where the user enters a special note such as an allergy or the like, the comment is recorded in the note field. In the complete field, whether or not endoscopy has already been finished is recorded. In the complete field, "Y" means that endoscopy has already been finished and "N" means that endoscopy has not been finished.

Note that instead of provision of the complete field in the patient DB 72, the control unit 21 may delete records associated with a patient who has already taken endoscopy and a patient who canceled endoscopy from the patient DB 72.

Figure 8:
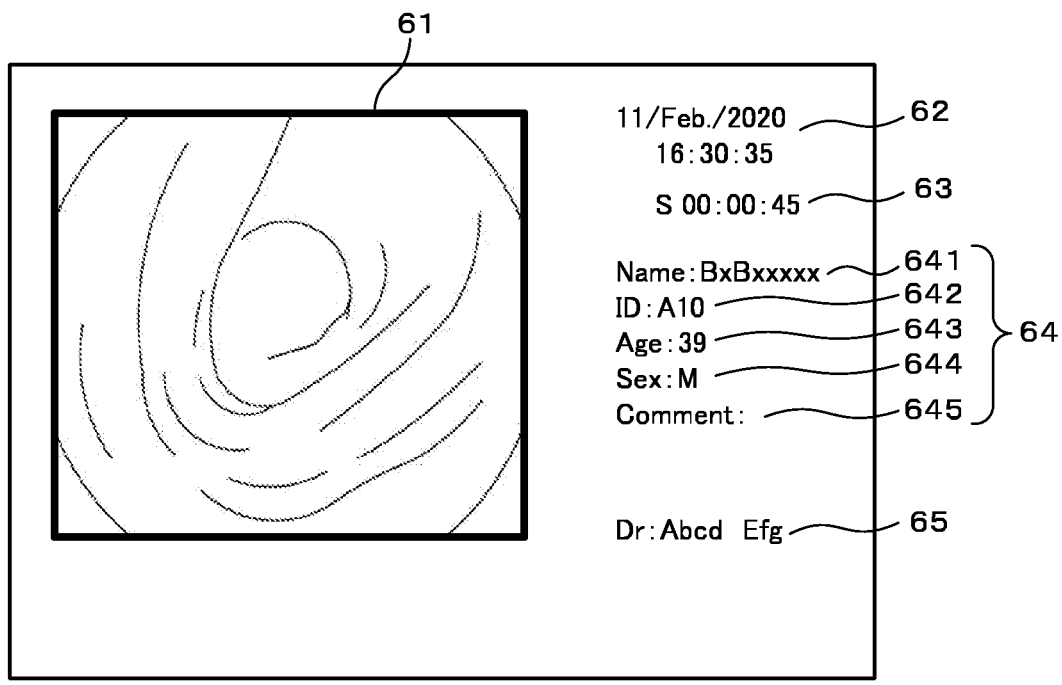
FIG. 8 is a screen example to be displayed during endoscopy.

FIG. 8 is an example of the screen to be displayed on the display device 50 during endoscopy. The screen shown in FIG. 8 includes an endoscopic image section 61, a date and time section 62, a stopwatch section 63, a patient section 64 and a doctor section 65. The patient section 64 includes a patient name section 641, a patient ID section 642, a patient age section 643, a patient sex section 644 and a comment section 645.

In the endoscopic image section 61, an endoscopic image captured using the endoscope 40 is displayed in real time. In the date and time section 62, a date and time is displayed. In the stopwatch section 63, a stopwatch is displayed on the basis of the operation by the user. The user can measure the time from when endoscopy is started using the stopwatch.

A patient name, a patient ID, a patient age and a patient sex are respectively displayed in the patient name section 641, the patient ID section 642, the patient age section and the patient sex section 644. The control unit 21 acquires the records associated with the patient who is taking endoscopy from the patient DB 72 and displays them at the respective sections of the patient section 64.

In the comment section 645, a comment input by a doctor using the keyboard 15 or a voice input during the endoscopy is displayed. The control unit 21 may display information recorded in the note field of the patient DB 72 or information acquired from an electronic medical record or the like at the comment section 645.

In the doctor section 65, a name of the doctor who is in charge of endoscopy is recorded. If the profile DB 71 described with reference to FIG. 5 is used, the control unit 21 displays at the doctor section 65 the user name corresponding to the profile that is in use. Names of the doctors who are in charge of respective patients may have been recorded in the patient DB 72. The control unit 21 may display the name of a doctor read from the ID card worn by the doctor, for example, at the doctor section 65.

Figure 9A:
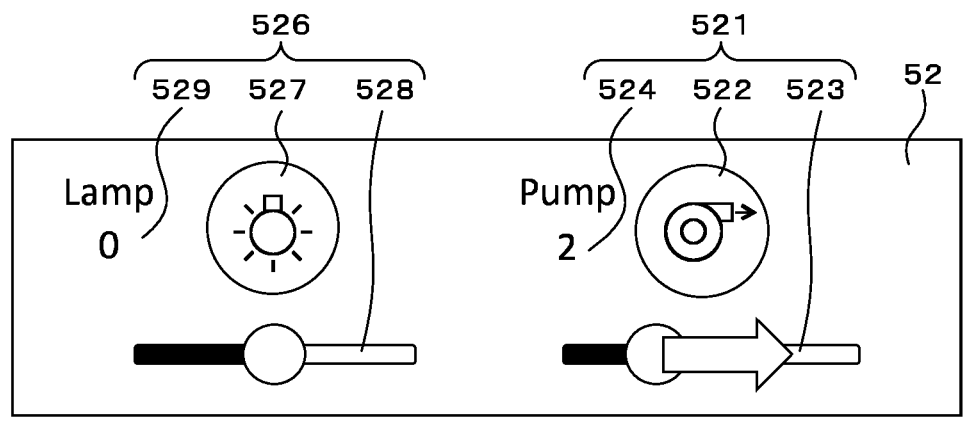
FIG. 9A illustrates the operation of an operation region.
Figure 9B:
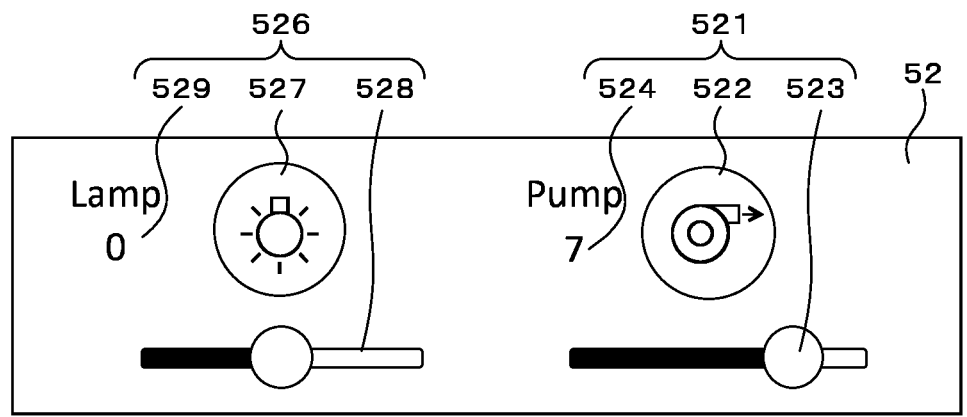
FIG. 9B illustrates the operation of the operation region.

FIGS. 9A and 9B illustrate the operation of the operation region 52. As described above, the operation region 52 includes the pump setting region 521 and the lamp setting region 526. The pump setting region 521 includes a pump switch 522, a pump adjustment switch 523 and a pump level section 524. The lamp setting region 526 includes a lamp switch 527, a lamp adjustment switch 528 and a lamp level section 529.

The pump switch 522 is an example of an on-off switch to be used when the user performs a switching operation between on and off states of the pump 34. The control unit 21 displays the pump switch 522 brightly if the pump 34 is in the on state and displays the pump switch 522 darkly if the pump 34 is in the off state.

The pump adjustment switch 523 is an example of an adjustment switch to be used when the user performs an output adjustment operation of the pump 34. The pump adjustment switch 523 includes a combination of a range display portion in a bold line that horizontally extends and a circular slider portion. The slider portion is movable from side to side along the range display portion. The range display portion shows an adjustable range concerning the output of the pump 34. The color of the range display portion is different on both sides of the slider portion.

The pump adjustment switch 523 is a slide switch that is operable by moving the slider portion along the range display portion from side to side. Note that the shape of the slider portion is not limited to be a circle. A slider portion having any shape such as a rectangle, for example, may be used.

In response to acceptance of an operation performed on the pump switch 522 by the user, the control unit 21 performs control of the switching between the on and off states. In response to acceptance of an operation performed on the pump adjustment switch 523 by the user, the control unit 21 performs output control of adjusting the output of the pump.

As such, the control unit 21 functions as a setting region display unit that displays the pump setting region 521 on the touch panel 25, as an operation acceptance unit that accepts an operation of the pump switch 522 and the pump adjustment switch 523, and as a change control unit that changes the operating state of the pump function. In place of the control unit 21, a driver circuit or the like for control of the pump connected to the bus may control the pump 34 in cooperation with the control unit 21.

The control unit 21 displays the output level of the pump 34 controlled based on the operation of the pump adjustment switch 523 at the pump level section 524 in text format. The output level of the pump 34 here means the pressure or the level of a flow rate delivered from the pump 34.

The lamp switch 527 is an example of an on-off switch to be used when the user performs a switching operation between the on and off states of the light source 33. The control unit 21 displays the lamp switch 527 brightly if the light source 33 is in the on state and displays the lamp switch 527 darkly if the light source 33 is in the off state.

The lamp adjustment switch 528 is an example of an adjustment switch to be used when the user performs an output adjustment operation of the light source 33. The lamp adjustment switch 528 includes a combination of a range display portion in a bold line that horizontally extends and a circular slider portion. The slider portion is movable from side to side along the range display portion. The range display portion shows an adjustable range concerning the output of the light source 33. The color of the range display portion is different on both sides of the slider portion.

The lamp adjustment switch 528 is a slide switch that is operable by moving the slider portion from side to side. Note that the shape of the slider portion is not limited to be a circle. A slider portion having any shape such as a rectangle, for example, may be used.

In response to acceptance of an operation performed on the lamp switch 527 by the user, the control unit 21 performs control of the switching between the on and off states of the light source 33. In response to acceptance of an operation performed on the lamp switch 527 by the user, the control unit 21 performs output control of adjusting the output of the light source 33.

As such, the control unit 21 functions as a setting region display unit that displays the lamp setting region 526 on the touch panel 25, as an operation acceptance unit that accepts an operation of the lamp switch 527 and the lamp adjustment switch 528, and as a change control unit that changes the operating state of the illumination function.

In place of the control unit 21, a driver circuit or the like for control of the light source connected to the bus may control the light source 33 in cooperation with the control unit 21.

The control unit 21 displays the output level of the light source 33 controlled based on the operation of the lamp adjustment switch 528 at the lamp level section 529 in text format. The output level of the light source 33 here means the brightness level of the light emitted from the light source 33.

Though description is made taking a procedure executed when an output adjustment operation of the pump 34 is performed as an example, the output operation of the light source 33 is also performed according to a similar procedure.

The user operates the pump adjustment switch 523 by performing a sliding operation of sliding a finger placed on the slider portion displayed on the touch panel 25 as shown in the hollow arrow illustrated in FIG. 9A. FIG. 9B shows a state in which the user completes the sliding operation and then releases the finger. The control unit 21 successively adjusts the output of the pump 34 in correspondence with the position of the slider portion that is being operated by the user. By this operation, the user can swiftly adjust the output of the pump 34. It is noted that the control unit 21 may adjust the output of the pump 34 after the user releases the finger from the slider portion.

Figure 10A:
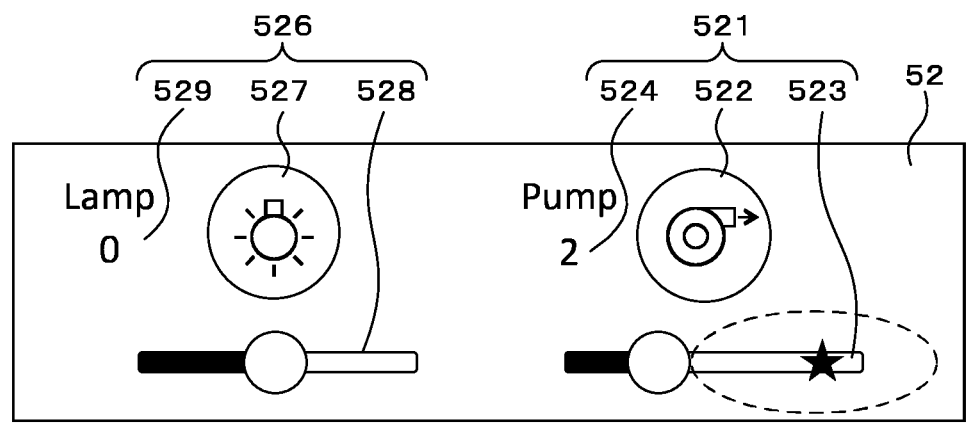
FIG. 10A illustrates the operation of the operation region.
Figure 10B:
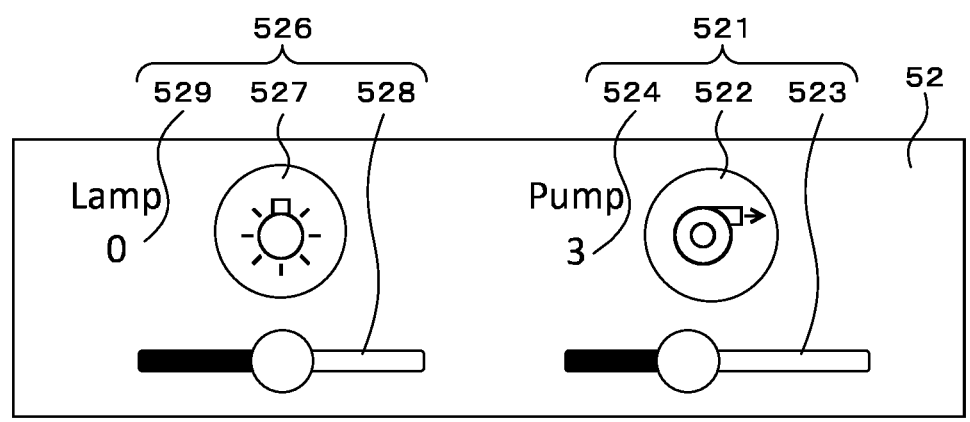
FIG. 10B illustrates the operation of the operation region.

FIGS. 10A and 10B show a case where the user adjusts the pump adjustment switch 523 by performing a tap operation. In the case where the user taps on one end of the pump adjustment switch 523 as shown by the filled-in star in FIG. 10A, the control unit 21 moves the slider to the right by a predetermined amount and increments the output level of the pump 34 by one. Likely, in the case where the user taps on the left side of the round slider portion, the control unit 21 moves the slider to the left by a predetermined amount and decrements the output level of the pump 34 by one.

The predetermined amount by which the slider portion is moved corresponds to the variation of the output level of the pump. In the case where the output level of the pump is variable from level 0 to level 10, for example, the predetermined amount is one-tenth of the length of the range display portion.

As such, in response to a tap operation by the user, the control unit 21 changes the output level of the pump 34 one by one. This makes it possible to prevent an operational error such as a sudden change in output of the pump 34.

Even if the user taps on a position around the range display portion as well as the precise position of the range display portion, the control unit 21 accepts the tap operation and moves the slider by a predetermined amount. In the case where the user taps on an area shown by the broke line in FIG. 10A, that is, an area including in and around the range display portion in any direction from the slider along the range display portion, for example, the control unit 21 accepts an operation of incrementing the output level of the pump 34 by one and moves the slider by a predetermined amount. The predetermined amount is a constant amount independent of the distance between the slider and the position on which the user taps. This eliminates the need for strictly adjusting the position where the user performs a top operation.

Even if the pump 34 or the light source 33 is set to the off state, the control unit 21 accepts an operation performed on the pump adjustment switch 523 or the lamp adjustment switch 528 to change the position of the slider. If the pump 34 or the light source 33 is turned to the on state, the control unit 21 controls the pump 34 or the light source 33 in correspondence with the position of the slider of the pump adjustment switch 523 or the lamp adjustment switch 528.

If the pump 34 and the light source 33 are adjustable at sufficiently finely levels, the control unit 21 may perform adjustment of five levels or ten levels with a single tap operation. In other words, the predetermined amount by which the control unit 21 moves the slider with a single tap operation is not limited to one level.

The control unit 21 stores the adjusting states of the pump setting region 521 and the lamp setting region 526 in a nonvolatile memory such as the auxiliary storage 23 or the like at any time and reads them at startup of the endoscope processor 20. This makes it possible to provide the endoscope processor 20 that starts up in user friendly settings even if aging of the pump 34 and the light source 33 occurs, for example.

If the use of the pump setting region 521 or the lamp setting region 526 at a setting larger than a predetermined threshold is stored, the control unit 21 may start up the endoscope processor 20 at a setting lower than the stored state. This makes it possible to provide the endoscope processor 20 that can be safely used without making the output of the pump 34 and the brightness of the light source 33 at startup get too large.

The control unit 21 may record the adjusting states of the pump setting region 521 and the lamp setting region 526 in the profile DB 71. This makes it possible to provide the endoscope processor 20 that is started up depending on the use of each of the users.

Figure 11:
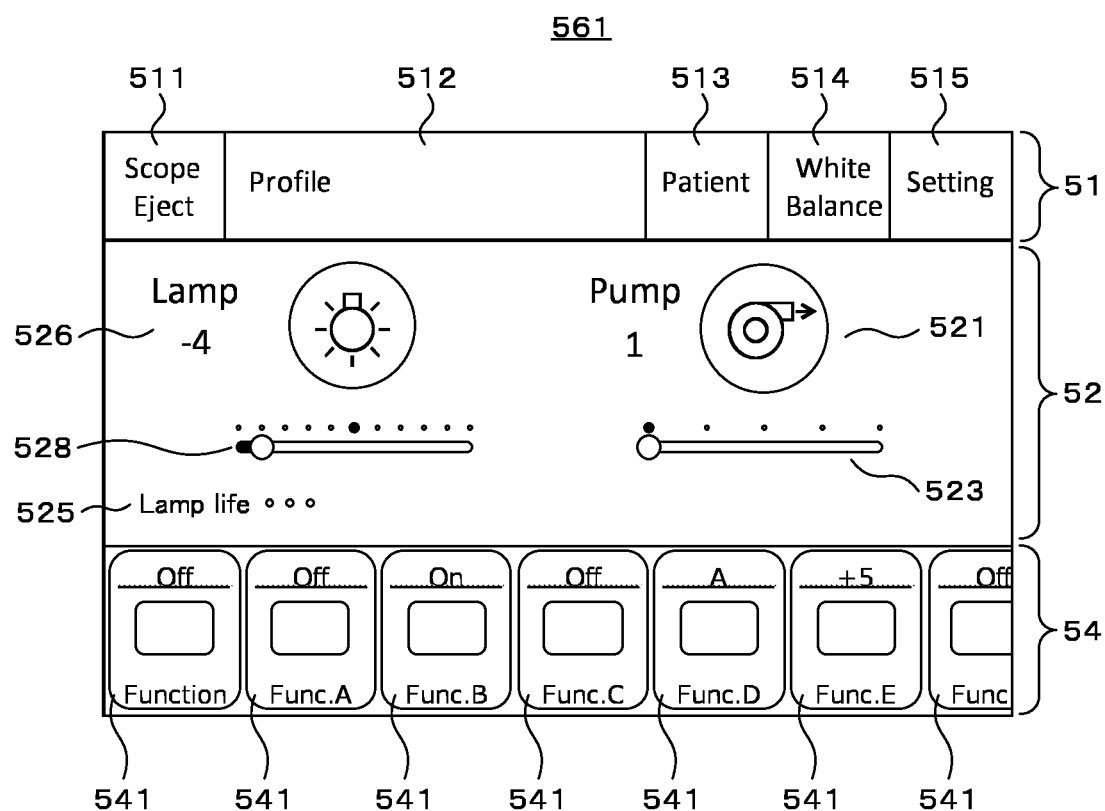
FIG. 11 is a modification of the top screen displayed on the touch panel.

FIG. 11 is a modification of the top screen 56 displayed on the touch panel 25. A lamp life section 525 is displayed between the lamp setting region 526 and the custom button region 54. The control unit 21 displays life expectancy of the light source 33 calculated based on the cumulative operating time of the light source 33 at the lamp life section 525.

For example, the control unit 21 decreases the number of dots displayed at the lamp life section 525 if the life expectancy becomes short. The user can grasp the maintenance period such as replacing of the light source 33 or the like based on the number of dots displayed at the lamp life section 525.

The control unit 21 displays a memory formed of dots above the lamp adjustment switch 528. The large dot at the center means standard brightness. In FIG. 11, the user can adjust the brightness in five levels on the bright side and in five levels on the dark side with reference to the standard brightness.

The control unit 21 displays a memory formed of dots above the pump adjustment switch 523. In FIG. 11, the user can adjust the pressure of the pump in five stages. The large dot at the leftmost position means that the pressure of the pump is the weakest of the five stages.

Note that the control unit 21 may accept an operation performed on the pump setting region 521 and the lamp setting region 526 by a voice input. For example, the user can set the lamp switch 527 to the on state by saying "LAMP ON." Likely, the user can operate the lamp adjustment switch 528 by saying "LAMP UP" or "LAMP DOWN."

By the voice input, the user can operate the pump setting region 521 and the lamp setting region 526 without separating the hand from the endoscope 40. The screen in FIG. 11 allows the user to visually confirm the state of the endoscope processor 20 and the effect of the operation thereof.

Figure 12:
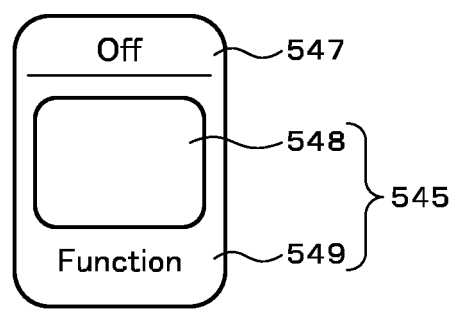
FIG. 12 illustrates the configuration of a custom button.

FIG. 12 illustrates the configuration of the custom button 541. The custom button 541 is a button used when the user adjusts various functions of the endoscope processor 20.

The custom button 541 includes a state section 547 and a function description section 545. The function description section 545 includes an icon section 548 and a name section 549. In the icon section 548, an icon for describing the function of each of the custom buttons 541 is displayed. In the name section 549, the name of each of the custom buttons 541 is displayed in text format. In the state section 547, the setting state of each of the custom buttons 541 is displayed in text format. It is noted that the user may display one of the icon section 548 and the name section 549 for the function the user can identify without misunderstanding.

Figure 13:
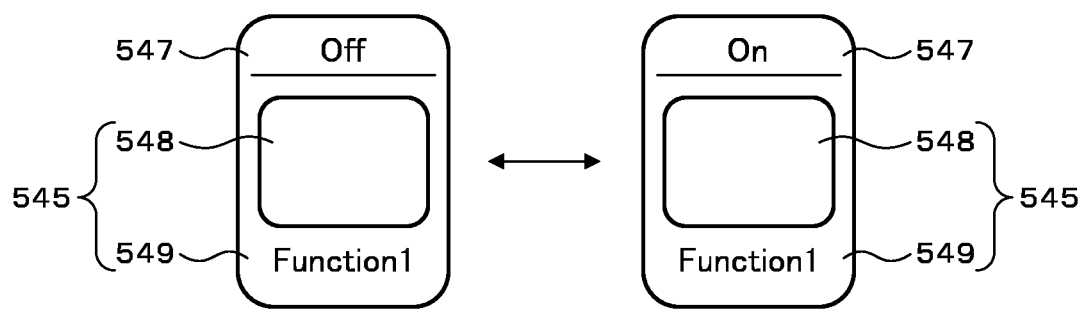
FIG. 13 illustrates the operation of the custom button.
Figure 14:
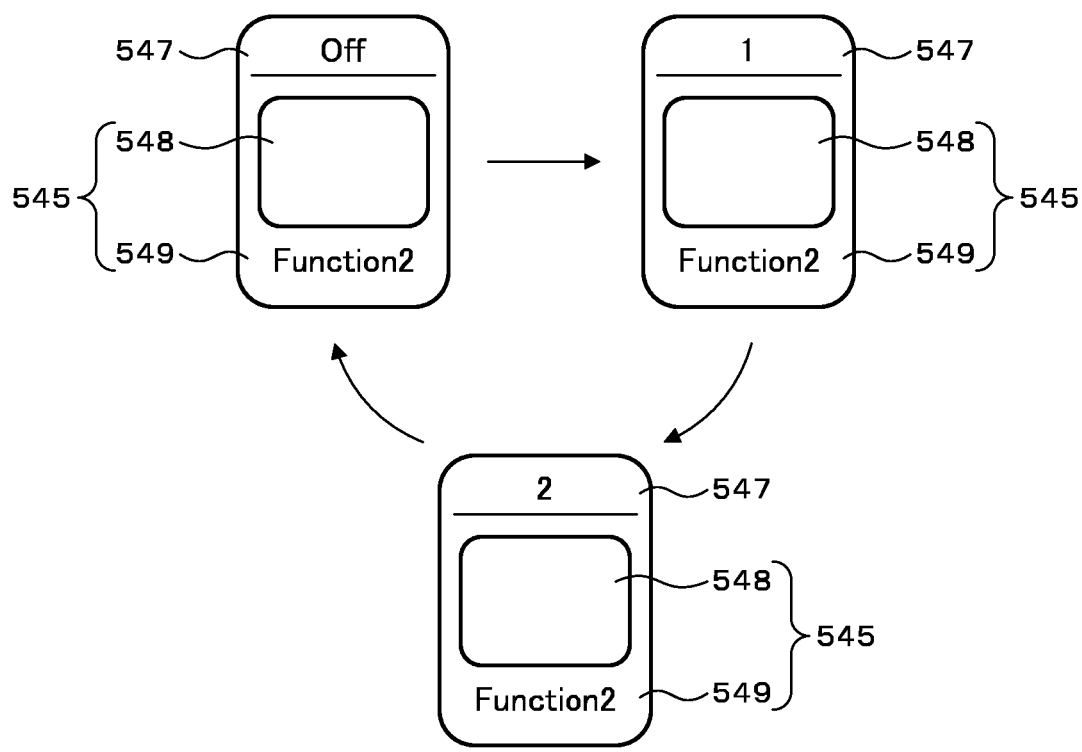
FIG. 14 illustrates the operation of the custom button.
Figure 15:
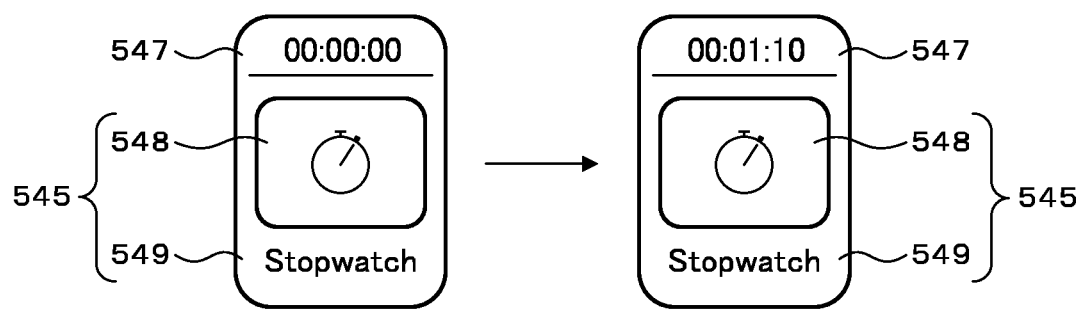
FIG. 15 illustrates the operation of the custom button.

FIGS. 13 to 15 illustrate the operation of the custom buttons 541. FIG. 13 illustrates an example of the custom button 541 for adjusting the function switchable between the on and off states. The button shown in FIG. 13 is used for switching between the on and off states of a specific image processing function, for example.

If the user taps on the custom button 541, the control unit 21 switches, between the on and off states, the function corresponding to the custom button 541 out of the functions of the endoscope processor 20.

FIG. 14 illustrates an example of the custom button 541 switchable among three states. If the user taps on the custom button 541, the control unit 21 displays the states of the function corresponding to the custom button 541 out of the functions of the endoscope processor 20 at the state section 547 in a sequentially switchable manner. By the user tapping on the custom button 541 three times, the state of the custom button 541 circles back and returns to the initial state.

If the custom button 541 is switchable among four states, for example, by the user tapping on the custom button 541 four times, the state of the custom button 541 circles back and returns to the initial state. The custom button 541 switchable in three states or more is used for switching a digital zoom magnification, for example.

As such, the control unit 21 functions as an operation acceptance unit that accepts an operation performed on the custom button 541 by the user and a change control unit that changes the operating state of the function corresponding to the custom button 541 an operation of which is accepted out of the functions of the endoscope processor 20. The control unit 21 displays the setting state of the custom button 541 in the state section 547.

FIG. 15 is an example of the custom button 541 concerning a stopwatch function. If the user taps on the custom button 541, the control unit 21 starts up the function of the stopwatch and displays an elapsed time in the state section 547. The control unit 21 also displays the elapsed time at the stopwatch section 63 described with reference to FIG. 8.

If the user taps on the custom button 541 during the measuring, the control unit 21 repeats stopping and restarting of the measurement of the elapsed time. If the user performs a press and hold operation on the custom button 541 during the measurement, the control unit 21 resets the stopwatch.

By the use of the custom button 541, the user can easily change the settings of the endoscope processor 20 even in the course of the endoscopy. It is noted that the control unit 21 may accept the operation of the custom button 541 by voice input. By saying "STOPWATCH," for example, the user can perform the same operation occurring when tapping on the custom button 541 for the stopwatch function. By the use of the voice input, the user can operate the custom button 541 without separating the hand from the endoscope 40.

Since the state section 547 is located above the custom button 541, the state section 547 is difficult to hide behind the hand or the finger of the user when the user operates the custom button 541. Accordingly, the endoscope processor 20 can be provided that has the custom buttons 541 easily operable.

Since both of the icon section 548 and the name section 549 are provided, the endoscope processor 20 can be provided that allows the user to surely operate the custom button 541 without misunderstanding.

Since the custom buttons 541 have the same size, the endoscope processor 20 can be provided that allows the user to arrange the custom buttons 541 in any order. Since the custom buttons 541 are aligned in the custom button region 54, the user can promptly find a necessary custom button 541 by performing a scrolling operation from side to side.

Thus, the endoscope processor 20 can be provided that can be easily used in the case where the doctor who is manipulating the endoscope 40 verbally instructs a nurse or a medical technician about the operation of the custom button 541.

Figure 16:
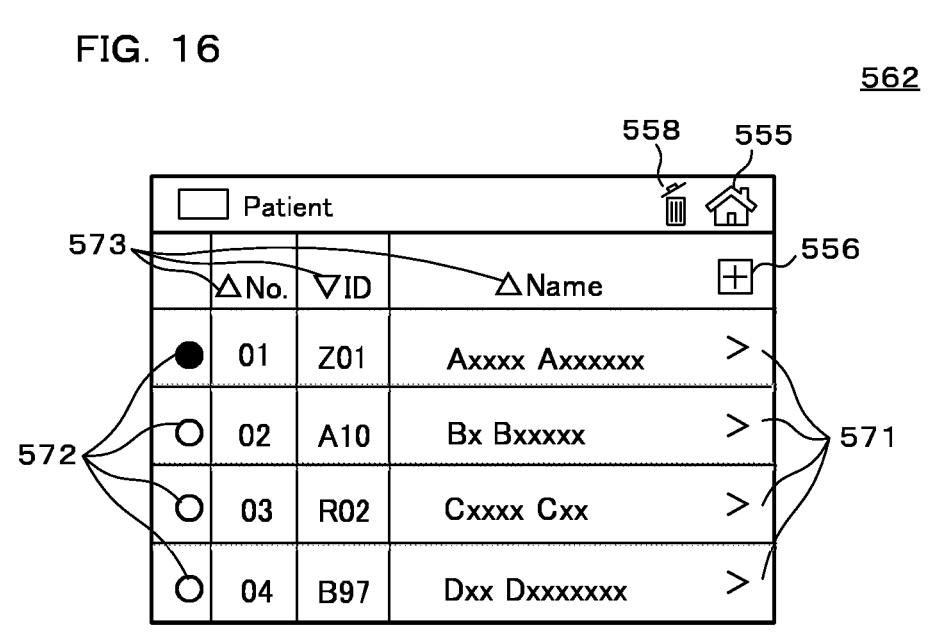

FIG. 16 illustrates the patient list screen 562. As described above, if accepting a selection of the patient button 513 on the top screen 561, the control unit 21 shifts the screen to the patient list screen 562. The patient list screen 562 displays the order, the ID and the name of the patients for whom "N" are recorded in the complete field out of the patients recorded in the patient DB 72 described with reference to FIG. 7 in tabular form containing one patient per one row. In other words, the patient list screen 562 shown in FIG. 16 displays a list of the patients who are scheduled to undergo endoscopy.

The table shown in FIG. 16 includes an option button column, a number column, an ID column and a name column from the left. In the option button column, option buttons 572 are displayed. FIG. 16 is a state in which the patient with No. 01 with the filled-in circle is being selected. At the right end of the name column, an advanced button 571 is displayed.

For each item in a column heading above the table, an inverted-triangle sort button 573 is displayed. At the right end of the column heading, an add button 556 is displayed. In a title bar at the top of the patient list screen 562, a delete button 558 and a home button 555 are displayed.

The shapes of the various kinds of buttons shown on the screen examples including FIG. 16 are mere examples and not limited to the illustrated or described modes. The option button 572, for example, is not limited to be circular. The option button 572 may be any shape such as elliptical, polygonal, star shape or the like. The selection status of the option button 572 may be displayed depending on variation in shape in place of variation in color. The selection status of the option button 572 may be displayed depending on the presence or absence of the display of the option button 572 itself. The selection status of the option button 572 itself may be displayed in characters.

The control unit 21 sets the option button 572 corresponding to the first patient in the list displayed on the patient list screen 562 as being selecting. If the order of endoscopy is changed, the user operates the option button 572 to select the next patient in the list for endoscopy. The option button 572 is one example of a patient acceptance unit that accepts a selection of the patient who will undergo endoscopy next.

The control unit 21 extracts the information related to the selected patient from the patient DB 72 and displays it in the patient section 64 of the screen described with reference to FIG. 8. After confirming that the next patient in the list for the endoscopy is displayed at the patient section 64, the user selects the home button 555. The control unit 21 returns the display of the touch panel 25 to the top screen 561.

In the case where the endoscopy is canceled, the user selects the delete button 558 with the option button 572 corresponding to a target patient selected. The control unit 21 deletes the corresponding patient from the patient DB 72 or records the cancellation at the complete field of the patient DB 72.

Figure 17:
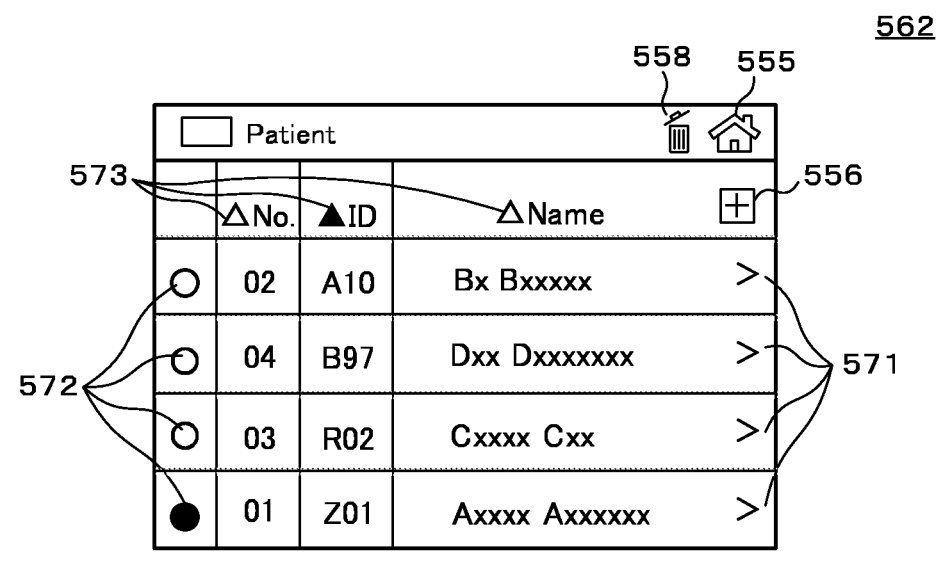
Figure 18:
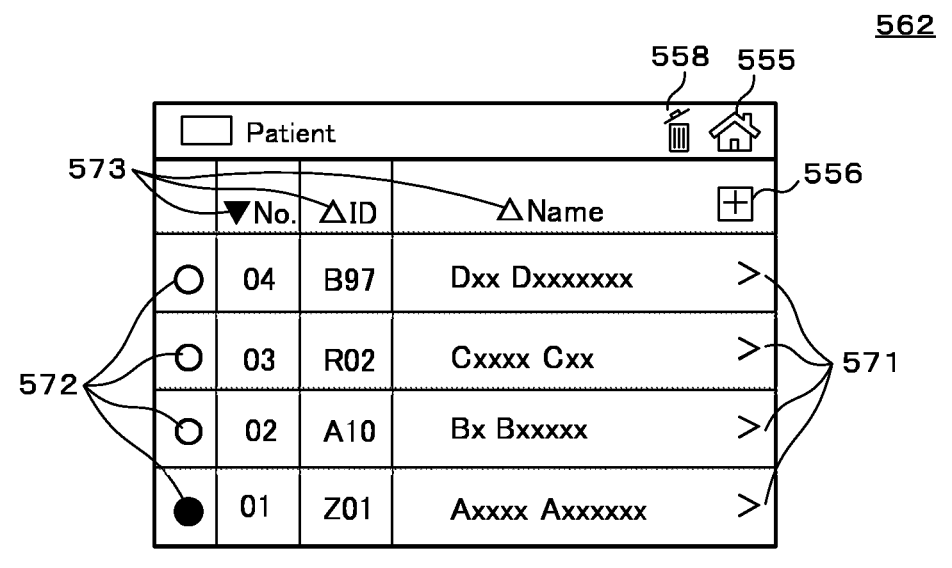

FIGS. 17 and 18 illustrate sorting of the patient list. FIG. 17 shows a state in which the user is selecting the sort button 573 in the ID column. The control unit 21 displays the selected sort button 573 by the filled-in triangle to thereby show that sorting is being made in ascending order of the patient ID. In the case where the user reselects the same sort button 573, the control unit 21 displays the selected sort button 573 by the filled-in inverted triangle to thereby show that sorting is being made in descending order of the patient ID.

As described above, the shapes of the various kinds of the buttons shown on the screen examples are all mere examples and not limited to the illustrated or described modes. The sort button 573 may have a shape other than a triangular shape such as an arrow shape, for example. The selection status of the sort button 573 may be displayed by variation in shape in place of variation in color. The selection status of the sort button 573 itself may be displayed in characters such as "descending order," "ascending order" and the like.

FIG. 18 shows a state in which the user is selecting the sort button 573 in the number column. The control unit 21 displays the selected sort button by the filled-in inverted triangle to thereby show that sorting is being made in descending order. If the user reselects the same sort button 573, the control unit 21 displays the selected sort button by the filled-in triangle to thereby show that sorting is being made in ascending order of the examination order.

In the case where the order of the endoscopy is changed or in the case where the endoscopy is canceled, the user suitably operate the sort button 573 to search for a target patient and selects the option button 572 of the patient. Then, the user selects the home button 555 or the delete button 558.

If the home button 555 is selected, the control unit 21 shifts the screen to the top screen 561 and stores the setting state of the sort button in the nonvolatile memory such as the auxiliary storage 23 or the like. When displaying the patient list screen 562 at the next time, the control unit 21 displays the patient list in a sorted state the same as that in the previous time.

The control unit 21 may display the patient list screen 562 in a default sorted state every time without storing the setting state of the sort button. In either case, the control unit 21 displays only the patients who have not yet taken the endoscopy on the patient list screen 562 to thereby allow the user to easily find a desired patient and select the option button 572 of the patient.

The control unit 21 may display both of the patients who have already taken the endoscopy and the patients who have not yet taken the endoscopy on the patient list screen 562. In such cases, it is desirable that the patients are displayed with flags to discriminate one from the other.

Even after selecting the option button 572 on the patient list screen 562 and preparing for endoscopy, there may be a case where, for example, the endoscopy cannot actually be performed due to situations such as an emergency examination required for another patient. There is also another case that endoscopy is interrupted halfway due to poor physical condition or the like of a patient. Even for such patients, "Y" is recorded in the complete field of the patient DB 72.

By displaying the patients who have already taken the endoscopy on the patient list screen 562, endoscopy of such patients can be conducted promptly. The control unit 21 may switch between display and non-display of the patients who have already taken endoscopy in response to a triple tap operation or the like during display of the patient list screen 562.

Figure 19:
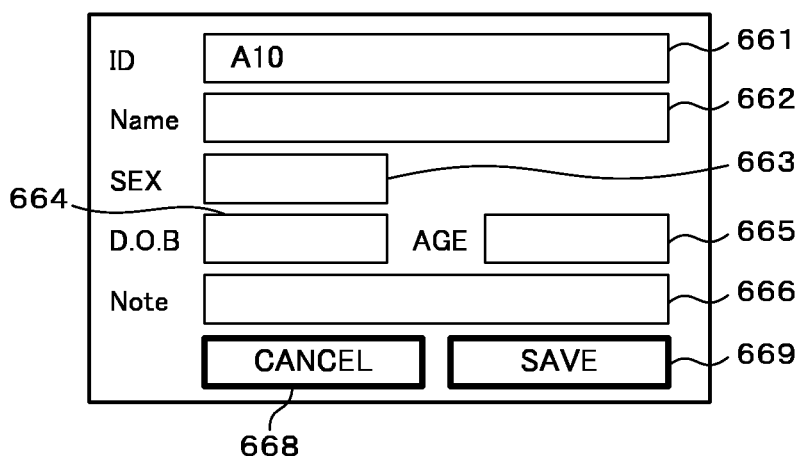
FIG. 19 is an example of a screen to perform registration and editing on the patient list.

FIG. 19 is an example of a screen to perform registration and editing on the patient list. The screen illustrated in FIG. 19 includes a patient ID entry section 661, a patient name entry section 662, a patient sex entry section 663, a patient birthday (D.O.B: date of birth) entry section 664, a patient age section 665, a note section 666, a cancel button 668 and a save button 669.

If accepting a selection of the add button 556 on the patient list screen 562 described with reference to FIGS. 16 to 18, the control unit 21 displays a registration/editing screen 563 illustrated in FIG. 19 with all the fields left blank. If accepting a selection of the advance button 571, the control unit 21 displays the registration/editing screen 563 illustrated in FIG. 19 with the items recorded in the patient DB 72 displayed in all the respective fields.

For example, the user such as a doctor, a nurse or a medical technician or the like has input information on the patients who will take endoscopy using the registration/editing screen 568 before conducting the endoscopy at that day. Here, the user sequentially inputs the information on the patients in order in which the endoscopy is scheduled. If the user selects the save button 669, the control unit 21 registers the information in the patient DB 72 in the order of acceptance of the input.

The control unit 21 may accept an input to the patient ID entry section 661 and automatically input to the sections other than the patient ID entry section 661 the information extracted from the electronic medical record or the like using the patient ID as a key. The control unit 21 may calculate an age of the patient based on the birthday of the patient input in the patient birthday entry section 664 and automatically input the age to the patient age section 665.

The control unit 21 may accept an input such as a patient ID or the like by voice input. The control unit 21 may display a software keyboard for an editing operation on the touch panel 25 and accept an operation by the user via the keyboard.

The control unit 21 may acquire a patient list previously created from a hospital information system (HIS).

The patient list is displayed in the order of registration, so that the patient list can automatically be displayed according to the order of the endoscopy without a special operation by the user.

Sorting based on the patient ID or the like allows the user to promptly find a target patient even if the order of the patient who takes endoscopy is changed due to another examination or the like to be taken by the patient.

Figure 20:
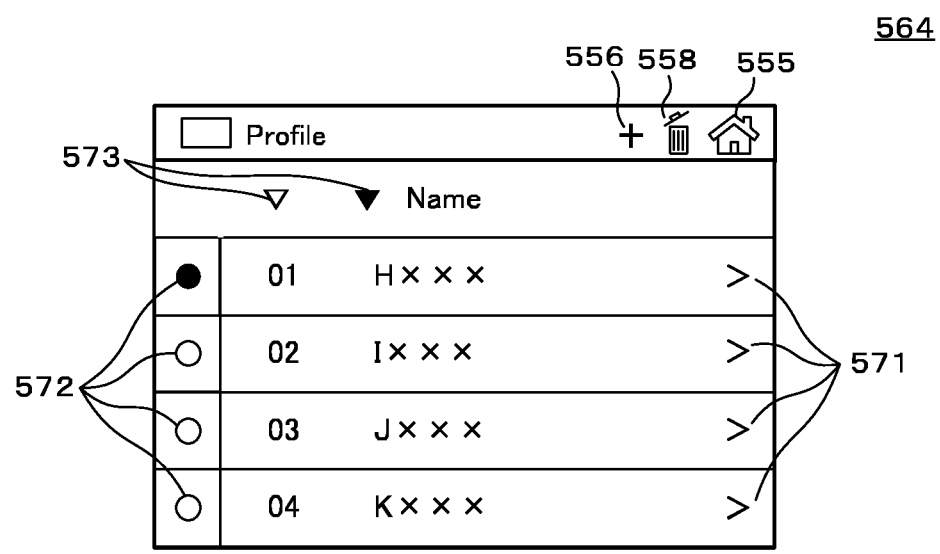
FIG. 20 illustrates a profile list screen.

FIG. 20 illustrates the profile list screen 564. If accepting a selection of the profile button 512 on the top screen 561 as described above, the control unit 21 shifts the screen to the profile list screen 564. On the profile list screen 564, the user number and the user name that are recorded in the profile DB 71 described with reference to FIG. 5 are displayed in tabular form.

The table shown in FIG. 20 contains an option button column, a number column and a name column from the left. In the option button column, the option buttons 572 are displayed. FIG. illustrates a state in which the profile with No. 01 indicated by the filled circle is being selected. At the right end of the name column, the advance button 571 is displayed.

For each item in a column heading above the table, the inverted-triangle sort button 573 is displayed. In the title bar at the top of the profile list screen 564, the add button 556, the delete button 558 and the home button 555 are displayed.

If the user selects the add button 556 or the advance button 571, the control unit 21 shifts the screen to the registration/editing screen 565 to accept addition or editing of the records in the profile DB 71. The concrete example of the registration/editing screen 565 is not described.

The user operates the option button 572 to select a profile to be used in the next endoscopy. If accepting a selection of the home button 555, the control unit 21 extracts the information on the selected profile from the profile DB 71 to change the settings of the endoscope processor 20. The control unit 21 shifts the screen to the top screen 561.

It is noted that the name of a doctor who is in charge of a patient or the purpose of endoscopy may be recorded in the patient DB 72. The control unit 21 searches the profile DB 71 for a corresponding profile and selects the profile to change the settings of the endoscope processor 20.

Figure 21:
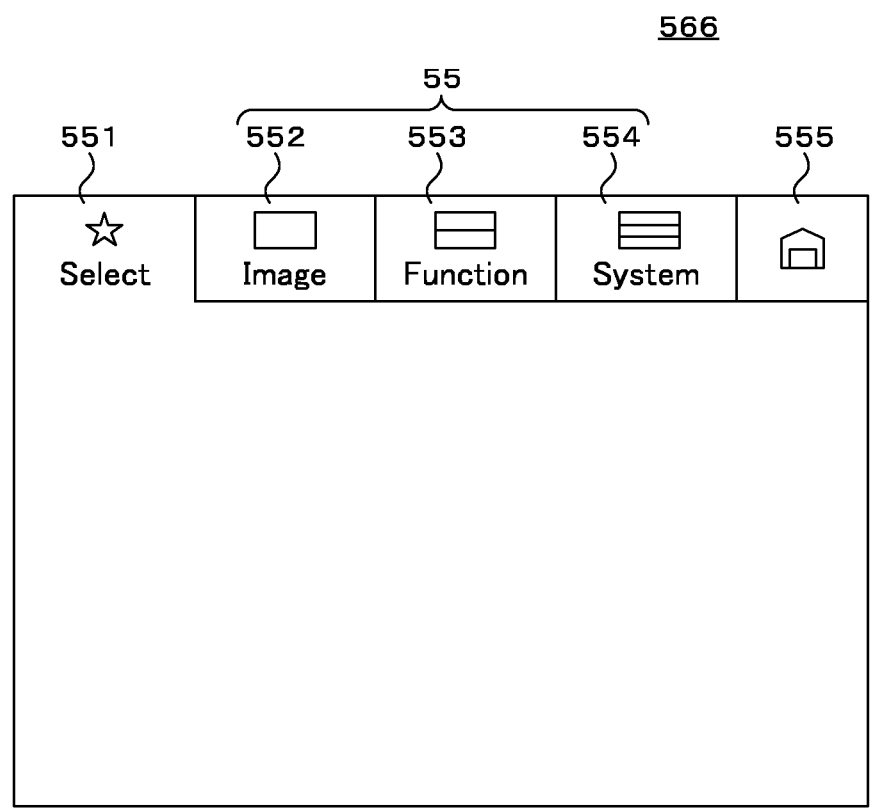
FIG. 21 illustrates a select menu screen.

FIG. 21 illustrates the select menu screen. At the top of the select menu screen, the select tab 551, the setting tab 55 and the home button 555 are displayed. The setting tab 55 includes an image tab 552, a function tab 553 and a system tab 554. FIG. 21 shows a default state in which no settable item that is to be displayed on the select menu screen is selected.

The number of tabs and the kinds of the tabs shown in FIG. 21 are mere examples. The setting tab 55 may include two or less tabs or four or more tabs. The setting tab 55 is an example of a second tab and a second button that are for displaying settable items with the option buttons 559 (see FIG. 22). Multiple select tabs 551 may be displayed. The select tab 551 is an example of a first tab and a first button that are for displaying settable items for which one of the option buttons 559 is being selected. By displaying the select tab 551 and the setting tab 55, the control unit 21 functions as a button display unit according to the present embodiment.

The endoscope processor 20 includes a lot of settable items that are suitably set by the user. The settable items are classified into multiple groups based on the functions or the like. In the present embodiment, a case where the settable items are classified into three groups respectively corresponding to the image tab 552, the function tab 553 and the system tab 554 will be described. Note that one settable item may be included in multiple groups.

Figure 22:
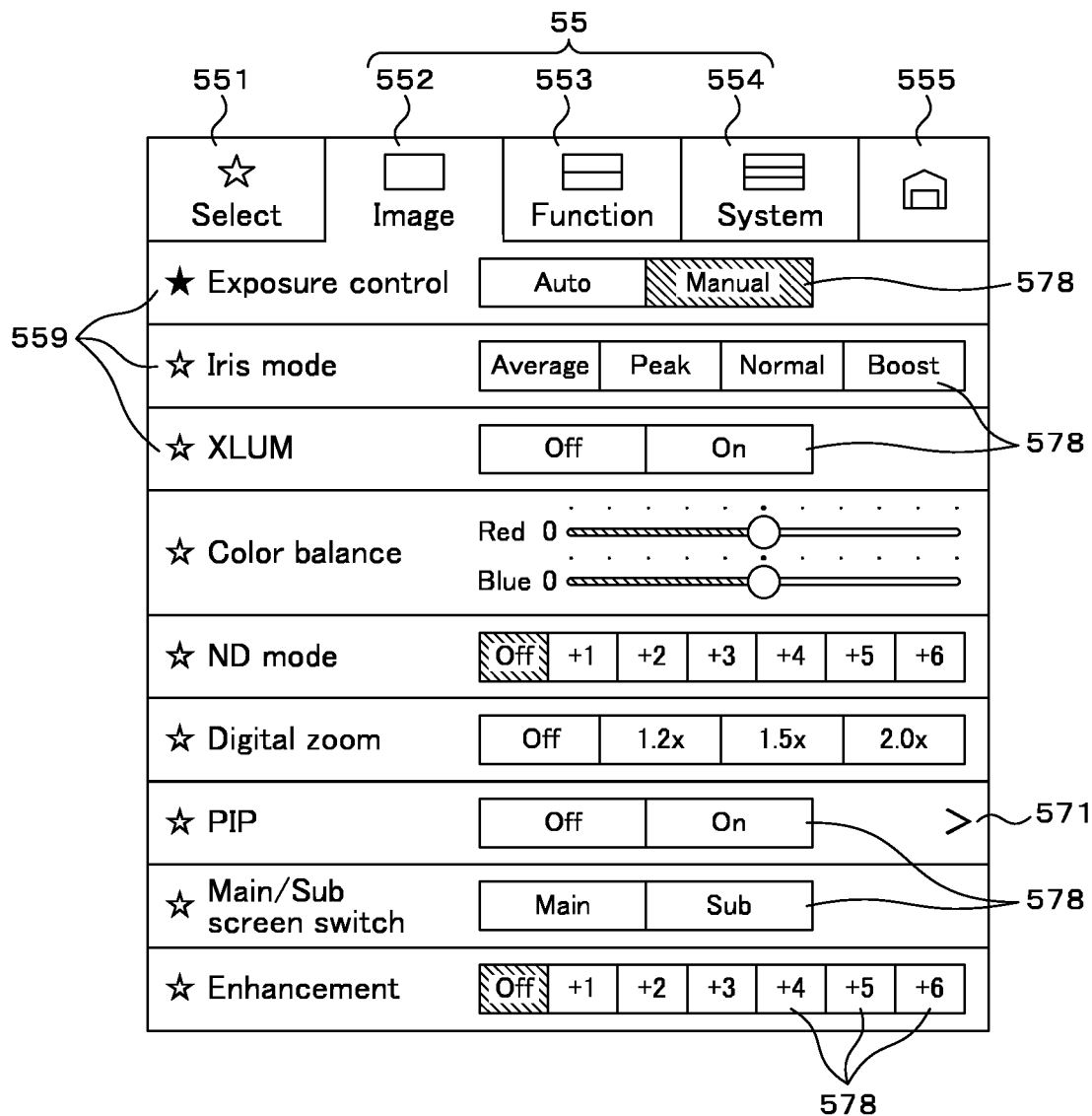
FIG. 22 illustrates a setting screen with an image tab selected.
Figure 23:
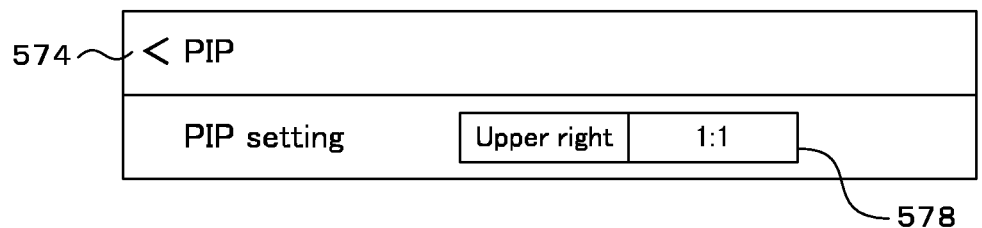
FIG. 23 illustrates a setting screen with the image tab selected.

FIGS. 22 and 23 illustrate the setting screen 566 with the image tab 522 selected. Settable items related to settings of an image to be displayed by the endoscope processor 20 are displayed in list form. At the left end of each of the settable items, the option button 559 is displayed. The settable items shown in FIG. 22 are a part of the settable items displayed when the image tab 552 is selected. The user searches for a desired settable item while vertically scrolling the screen.

Settable items illustrated in and after FIG. 22 are mere examples. By displaying the setting screen 566 with the second tab such as an image tab or the like selected, the control unit 21 functions as a second settable item display unit according to the present embodiment.

The user selects the option button 559 displayed at the left end of the settable item that the user desires to frequently use. In FIG. 22, the option button 559 for the uppermost settable item "Exposure control" is being selected. By storing the option button 559 for which a selection by the user has been accepted, the control unit 21 functions as a selection storage unit according to the present embodiment.

For the settable item of "Exposure control," for example, two setting option buttons 578 of "Auto" and "Manual" are displayed. For the lowermost settable item of "Enhancement," a total of seven setting option buttons 578 including "Off" and "+1" to "+6" are displayed. The control unit 21 accepts a selection of the setting option button 578 on which the user taps to adjust the level of image enhancement processing.

It is noted that display of the setting screen 566 is not limited to tab form in which tabs for switching are arranged at the top of the screen. The control unit 21 may display in a switchable manner a selection screen in which buttons respectively corresponding to the select tab 551, the image tab 552, the function tab 553 and the system tab 554 are aligned, and a settable item screen in which a list of settable items is displayed if any one of the buttons is selected.

The control unit 21 may display a list of the settable items corresponding to the select tab 551 at a default setting. Meanwhile, the control unit 21 displays the select tab 551, the image tab 552, the function tab 553 and the system tab 554 when the endoscope is used by a specific user who gets familiarized with operation of the endoscope processor 20. The control unit 21 may display the select tab 551, the image tab 552, the function tab 553 and the system tab 554 based on an instruction from the user. This makes it possible to provide the endoscope processor 20 that is operable without the unfamiliar user being puzzled over a lot of settable items.

For a settable item capable of setting the details, the advance button 571 is displayed at the right end. If accepting a selection of the advance button 571, the control unit 21 displays detailed items concerning this settable item. The concrete example thereof will be described below.

FIG. 23 shows an example of a screen to be displayed on the touch panel 25 by the control unit 21 if the advance button 571 for the settable item of "Picture in Picture" (PIP) in the third row from the bottom is selected. At the left end of the "PIP" row on the screen in FIG. 23, a close button 574 is displayed. It is noted that the margin of the screen is not illustrated here.

The user sets "PIP Setting" to a desirable state and then selects the close button 574. The control unit 21 accepts the setting to "PIP setting" and shifts the display to the screen described with reference to FIG. 22.

Figure 24:
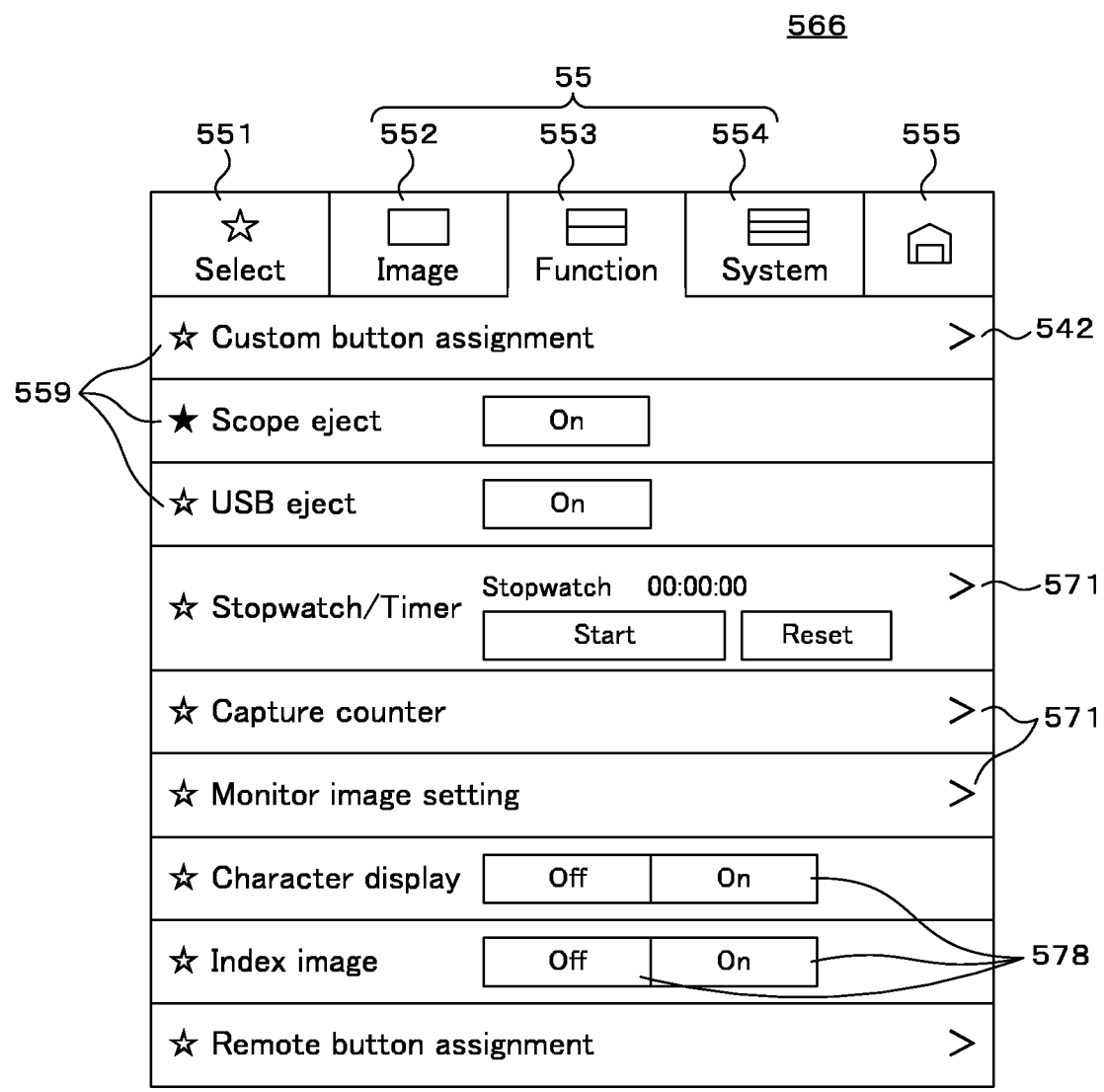
FIG. 24 illustrates a setting screen with a function tab selected.

FIG. 24 illustrates the setting screen 566 with the function tab 553 selected. Settable items related to various functions possessed by the endoscope processor 20 are displayed in list form. The option button 559 is displayed at the left end of each of the settable items. The settable items shown in FIG. 24 are a part of the settable items displayed when the function tab 553 is selected. The user searches for a desired settable item while vertically scrolling the screen.

A settable item of "Custom button assignment" is displayed in the uppermost row on the screen shown in FIG. 24. At the right end of this row, a custom region setting button 542 is arranged. The details of the custom region setting button 542 is described below.

In FIG. 24, the option button 559 for the settable item of "Scope eject" in the second row from the top is being selected. Out of the settable items shown in FIG. 24, the control unit 21 accepts an operation on the "ON" button if the user taps on and holds these items, concerning the settable item of "Scope eject" to eject the endoscope 40 from the endoscope processor 20 and the settable item of "USB eject" to eject the USB memory from the reading part 28. This makes it possible to prevent the endoscope 40 and the USB memory from being ejected from the endoscope processor 20 due to a wrong operation.

Figure 25:
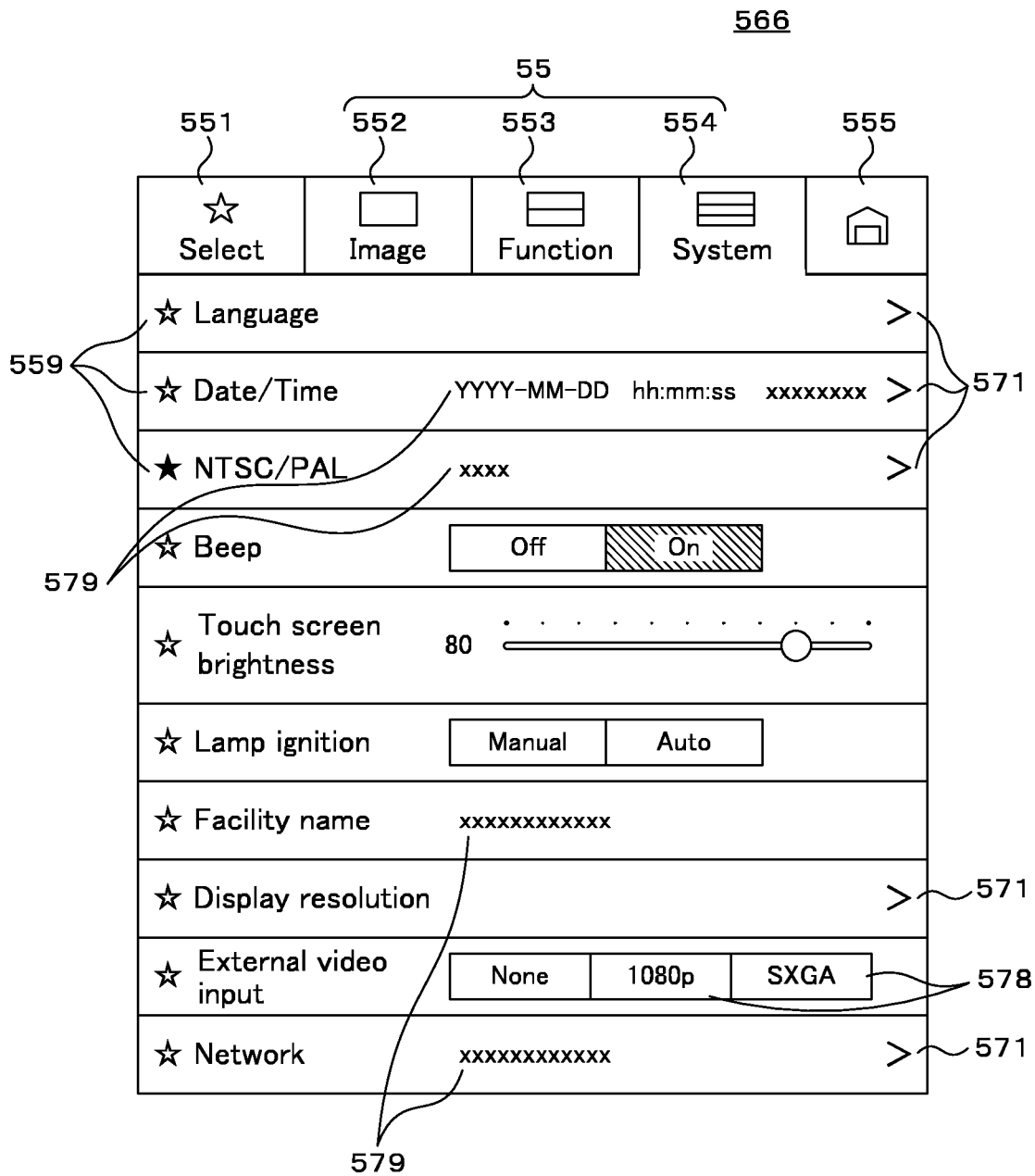
FIG. 25 illustrates a setting screen with a system tab selected.

FIG. 25 illustrates the setting screen 566 with the system tab 554 selected. Settable items related to system settings of the endoscope processor 20 are displayed in list form. The settable items shown in FIG. 25 are a part of the settable items displayed when the system tab 554 is selected. The user searches for a desired settable item while vertically scrolling the screen.

In FIG. 25, the option button 559 for the settable item of "National Television System Committee/Phase Alternating Line (NTSC/PAL)" in the third row from the top is being selected. For the settable items of "Date/TIME," "NTSC/PAL," "Facility Name" and "Network," setting display sections 579 for displaying the current setting state in text format are displayed.

Figure 26:
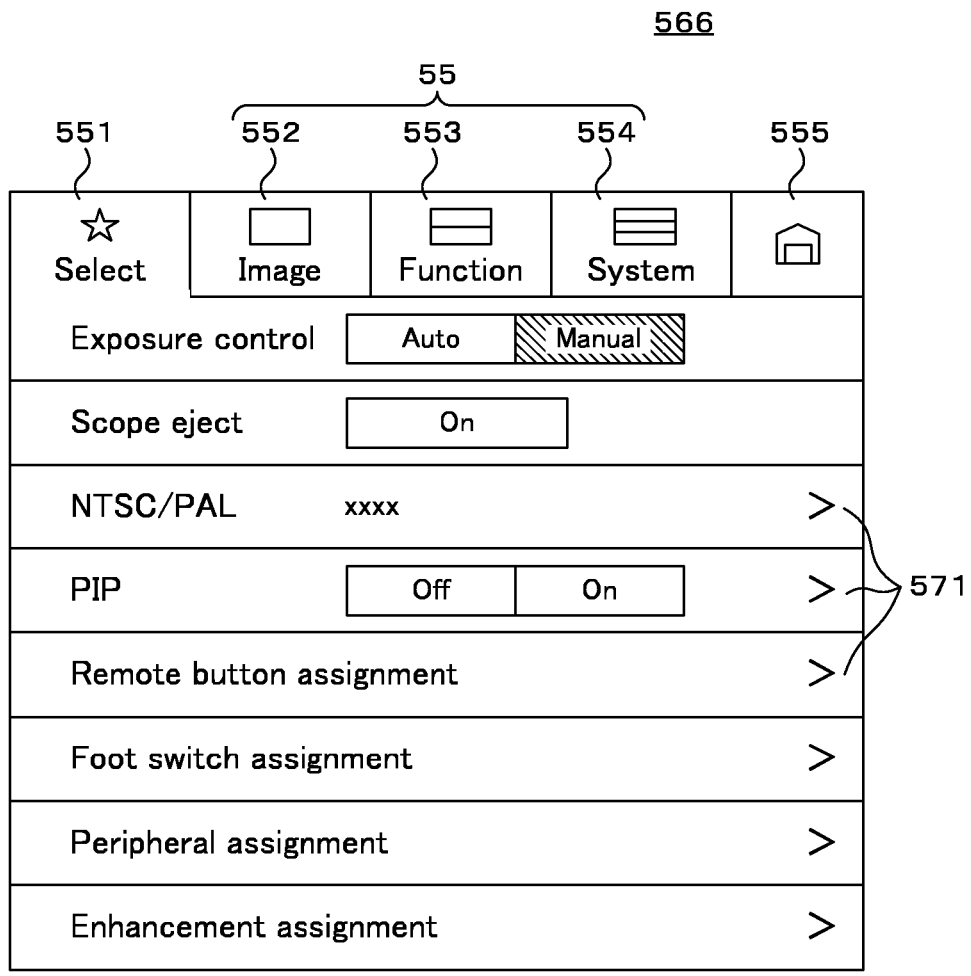
FIG. 26 illustrates the select menu screen.
Figure 27:
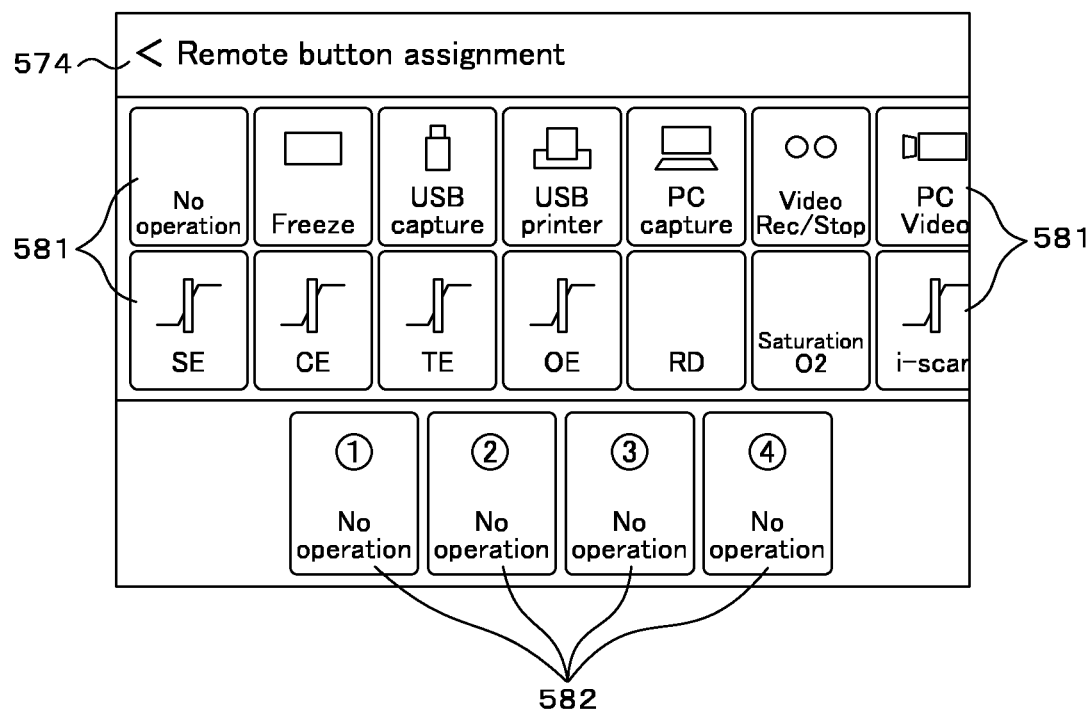
FIG. 27 illustrates the select menu screen.
Figure 28:
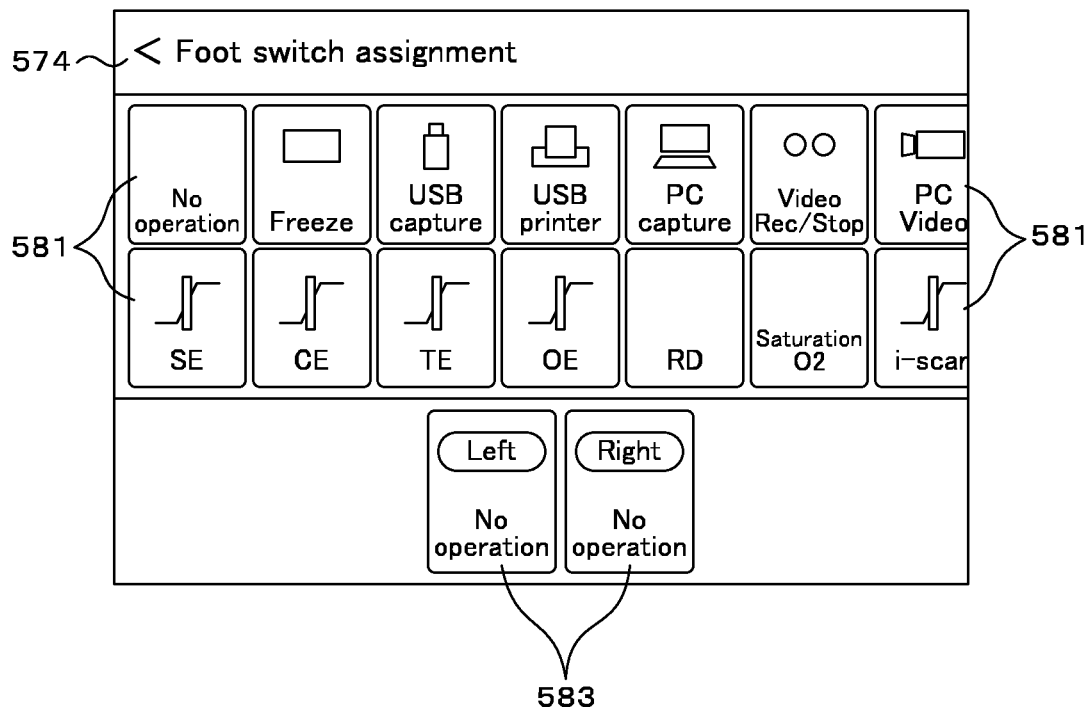
FIG. 28 illustrates the select menu screen.

FIGS. 26 to 28 illustrate the select menu screen. On the screen described with reference to FIG. 21, the settable items obtained when the option buttons 559 have been selected are additionally displayed. By selecting the option buttons 559, the user can collect the settable items the user wants to frequently use on the screen displayed by the select tab 551. By displaying the setting screen 566 with the select tab 551 selected, the control unit 21 functions as a first settable item display unit according to the present embodiment.

FIG. 27 is a screen example to be displayed on the touch panel 25 by the control unit 21 when the advance button 571 of the settable item of "Remote button assignment" is selected. Below the settable item of "Remote button assignment," a menu is displayed for setting the function of the control buttons 431 provided in the operation part 43 of the endoscope 40.

In the lowermost row, control button icons 582 representing the four control buttons 431 are arranged. FIG. 27 displays a state of "No operation" indicating that a setting of the control buttons 431 has not yet been set. In the second and third rows from the bottom, function icons 581 representing the functions that can be set to the control buttons 431 are arranged. The number of function icons 581 is more than that can be arranged within the width of the screen of the touch panel 25. The user can scroll the row in which the function icons 581 are arranged from side to side.

The user drags and drops the desired function icon 581 to the control button icon 582. The control unit 21 displays the dragged and dropped function icon 581 in place of the control button icon 582. The control unit 21 assigns the function corresponding to the dragged and dropped function icon 581 to the control button 431.

The user can use the function assigned to the control button 431 without separating the hand from the endoscope 40 during endoscopy. In other words, if the user operates the control button 431, the control unit 21 executes the function assigned to the control button 431.

FIG. 28 is a screen to be displayed on the touch panel 25 by the control unit 21 when the advance button 571 for the settable item of "Foot switch assignment" is selected. Below the settable item of "Foot switch assignment," a menu for setting the functions of the foot switch 17 is displayed.

In the lowermost row, two foot switch icons 583 respectively representing right and left buttons of the foot switch 17 are arranged. In FIG. 28, no function of the buttons of the foot switch 17 is set. It is noted that the control unit 21 displays three foot switch icons 583 if the foot switch 17 formed of three buttons is connected to the endoscope processor 20, for example.

In the second and third rows from the bottom, function icons 581 representing the functions that can be set to the foot switch 17 are arranged. The user drags and drops the desired function icon 581 to the foot switch icon 583. The control unit 21 displays the dragged and dropped function icon 581 in place of the foot switch icon 583. The control unit 21 assigns the function corresponding to the dragged and dropped function icon 581 to the buttons for the foot switch 17.

The user can use the function assigned to the foot switch 17 without separating the hand from the endoscope 40 during endoscopy. In other words, if the user operates the foot switch 17, the control unit 21 executes the function assigned to the foot switch 17.

FIGS. 29 to 33 illustrate the select menu setting screen 567. In FIGS. 29 to 33, the name of each settable item is abstractly represented by a character string such as "BBB," "XXZ" or the like.

Figure 29:
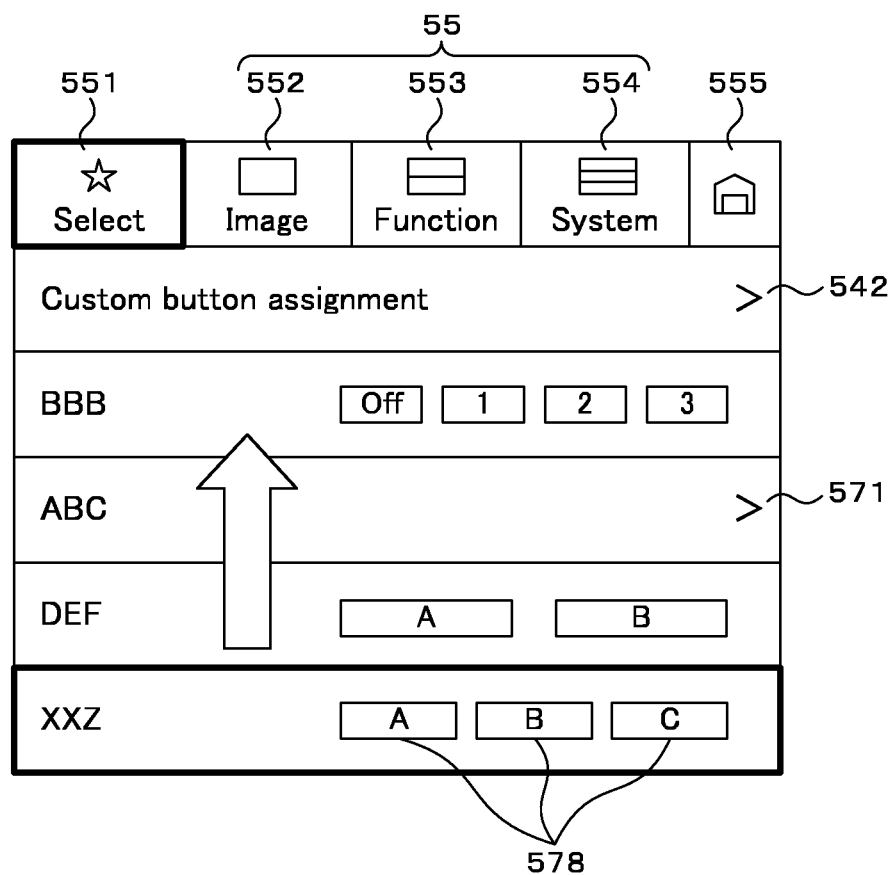
FIG. 29 illustrates a select menu setting screen.

As described above, in response to the user performing a long-tap operation or the like during the display of the select menu screen, the control unit 21 switches the screen to the select menu setting screen 567. In FIG. 29, in response to a selection of the settable item of "XXZ" at the lowermost row with a long tap operation, the screen is switched to the select menu setting screen 567. In FIG. 29, the settable item of "XXZ" that is being selected is represented by a bold frame.

Figure 30:
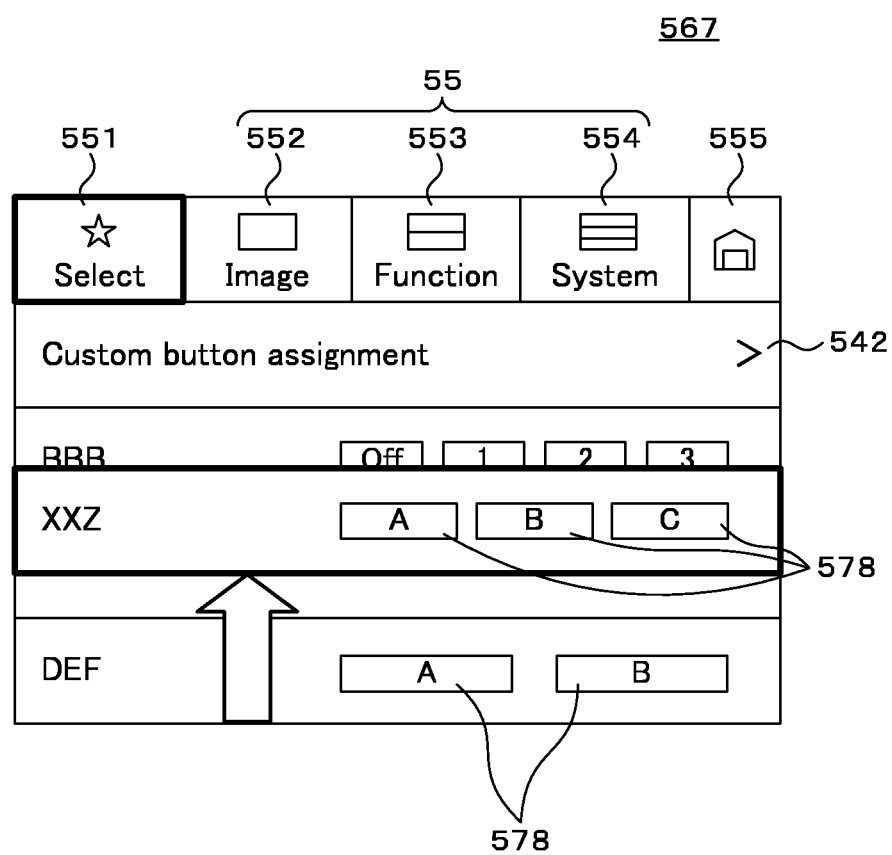
FIG. 30 illustrates the select menu setting screen.
Figure 31:
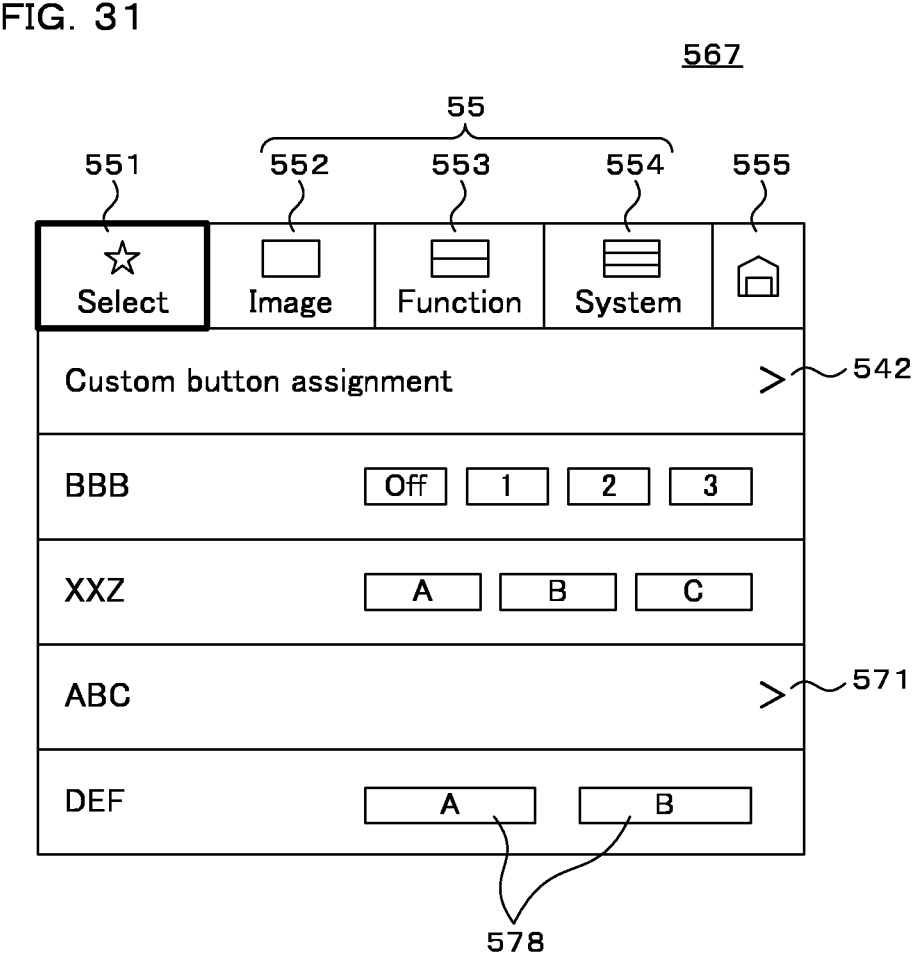
FIG. 31 illustrates the select menu setting screen.
Figure 32:
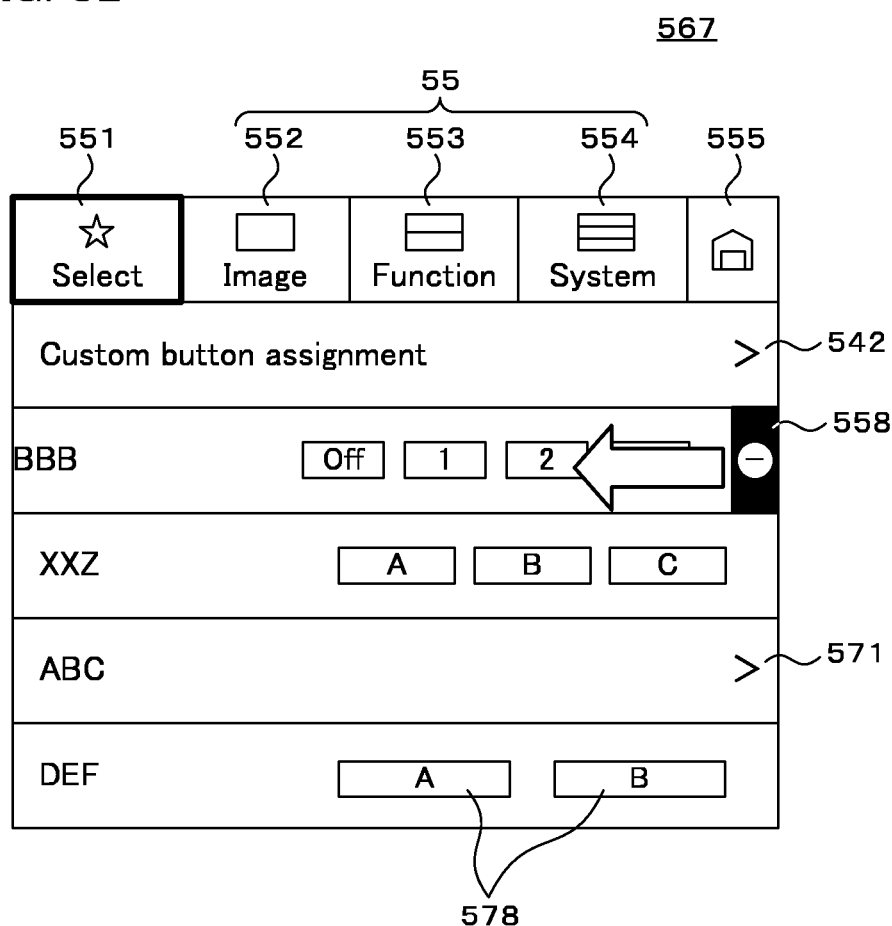
FIG. 32 illustrates the select menu setting screen.

As shown by the hollow arrow in FIG. 29, the user slides a finger with the settable item of "XXZ" selected. The control unit 21 moves the selected settable item of "XXZ" to follow the finger movements of the user as shown in FIG. 30. The user releases the finger at a desirable position where the settable item is to be arranged. The control unit 21 inserts the settable item of "XXZ" between the "BBB" and the "ABC." As such, the control unit 21 functions as a change acceptance unit that accepts change in an arrangement position of the settable item within the select menu screen.

Figure 33:
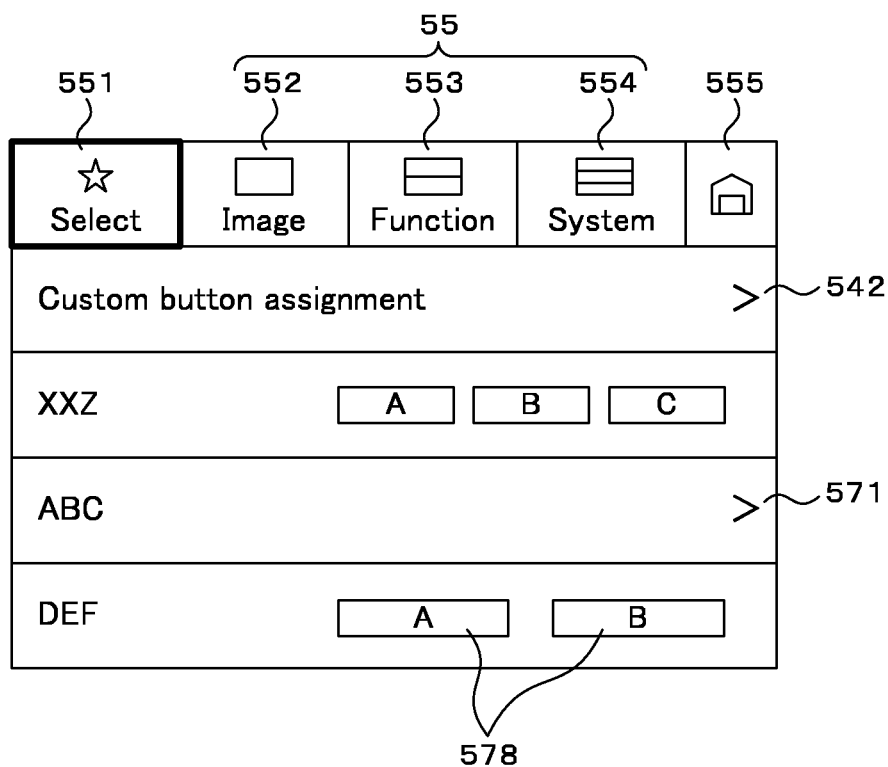
FIG. 33 illustrates the select menu setting screen.
Figure 34:
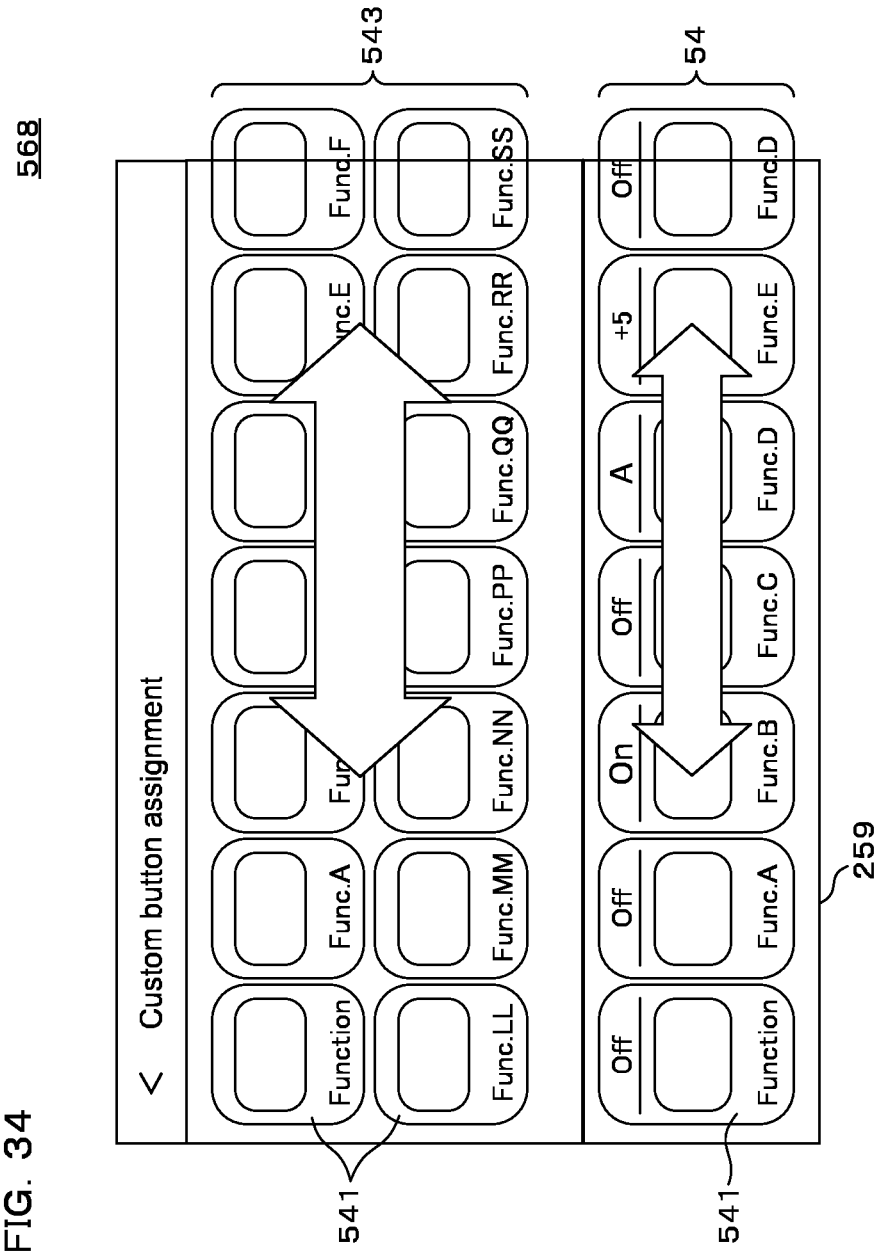
FIG. 34 illustrates a custom button region editing screen.

If any settable item is deleted from the select menu screen, the user performs a sliding operation leftward on the settable item to be deleted. The control unit 21 displays the delete button 558 at the right end of the settable item having accepted the sliding operation. If the settable item is to be deleted, the user performs a tap operation on the delete button 558. If accepting the tap operation performed on the delete button 558 by the user, the control unit 21 deletes this settable item from the select menu screen as shown in FIG. 33. The control unit 21 sets the option button 559 for the settable item having accepted the delete instruction as being unselected. As such, the control unit 21 functions as a delete acceptance unit according to the present embodiment.

It is noted that the user cancels the selection of the option button 559 on the setting screen 566 described with reference to FIGS. 22 to 25 to thereby delete the settable item from the select menu screen.

By the operation described above, the user can make the setting such that the frequently-used settable item is displayed at the upper part of the select menu screen. By using the select menu screen having been set, the user can promptly operate the endoscope processor 20.

FIGS. 34 to 41 illustrate the custom button region editing screen 568. The user can edit the kind and the order of the custom buttons 541 displayed in the custom button region 54 using the custom button region editing screen 568. If accepting a selection of the custom region setting button 542 described with reference to FIG. 24, the control unit 21 shifts the screen to the custom button region editing screen 568. The control unit 21 functions as a custom button selection acceptance unit and an arrangement order change acceptance unit of the present embodiment via the custom button region editing screen 568.

The control unit 21 may display the region shown in FIGS. 34 to 41 below the settable item of "Custom button assignment" as in the screen described with reference to FIGS. 27 and 28.

The custom button region editing screen 568 includes a candidate button region 543 and the custom button region 54. In the candidate button region 543, the custom buttons 541 that can be arranged in the candidate button region 543 are displayed in list form. As such, the control unit 21 functions as a custom button region display unit and a candidate button region display unit. It is noted that for each of the custom buttons 541 within the candidate button region 543, the state section 547 described with reference to FIG. 12 is left blank.

In FIGS. 34 to 41, an area displayable on the touch panel 25 is represented by a display area frame 259. As shown by the hollow arrow in FIG. 34, the user can horizontally scroll the candidate button region 543 and the custom button region 54 independently.

Figure 35:
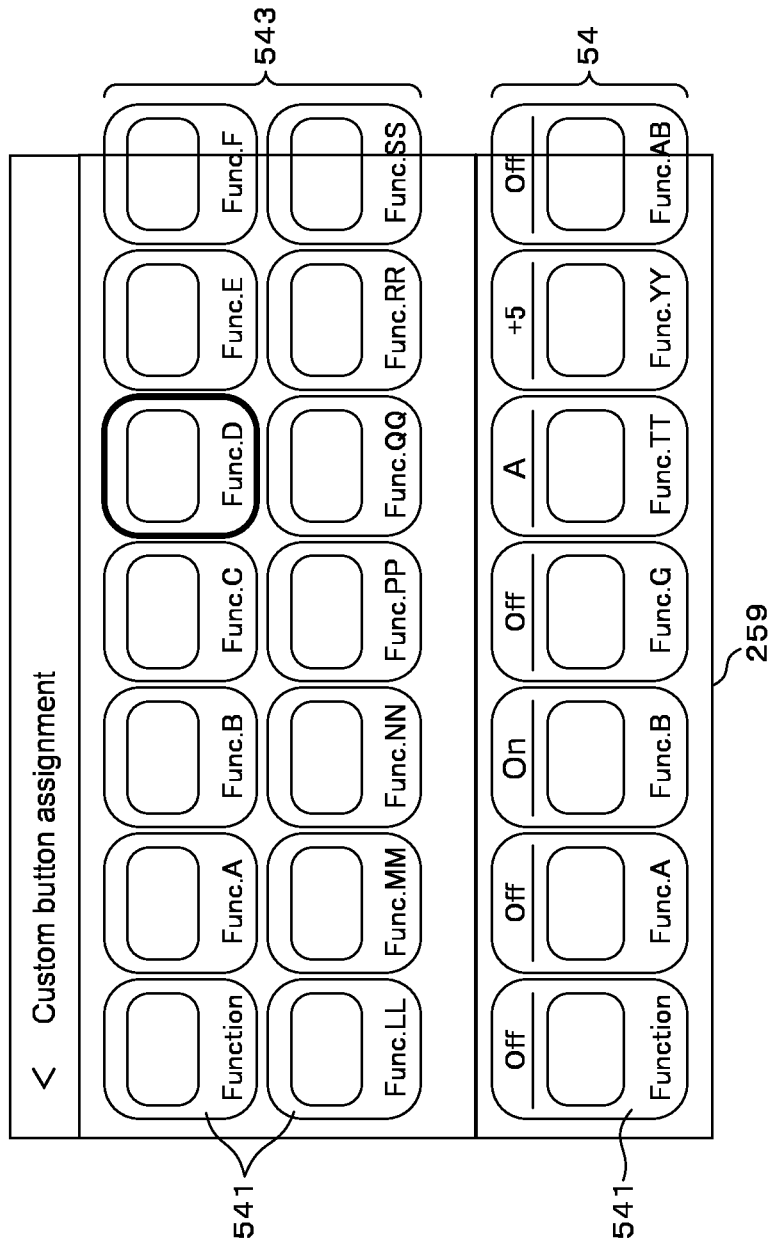
FIG. 35 illustrates the custom button region editing screen.

If the user performs a press and hold operation, such as a touch for a predetermined time period, on any one of the custom buttons 541 within the candidate button region 543, the control unit 21 accepts selection of the custom button 541. In FIG. 35, the custom button 541 of "Func. D," selection of which has been accepted by the control unit 21, is represented by the bold frame.

Figure 36:
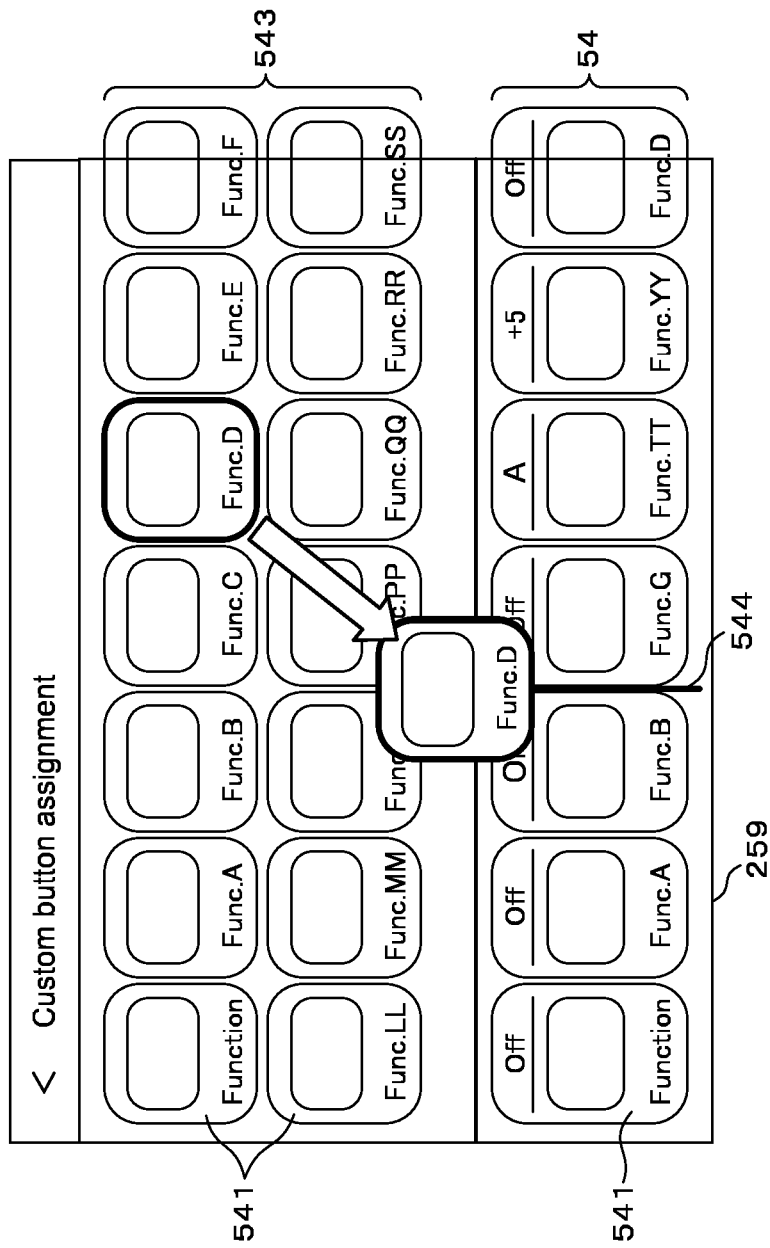
FIG. 36 illustrates the custom button region editing screen.

As shown by the hollow arrow in FIG. 36, the user slides a finger with the custom button 541 selected. The control unit 21 moves the selected custom button 541 to follow the finger movement of the user as shown in FIG. 22. If the custom button 541 is moved into the custom button region 54, the control unit 21 displays a bold-line-like insertion marker 544. The control unit 21 changes the position of the insertion marker 544 horizontally depending on the position of the custom button 541 that is being selected.

Figure 37:
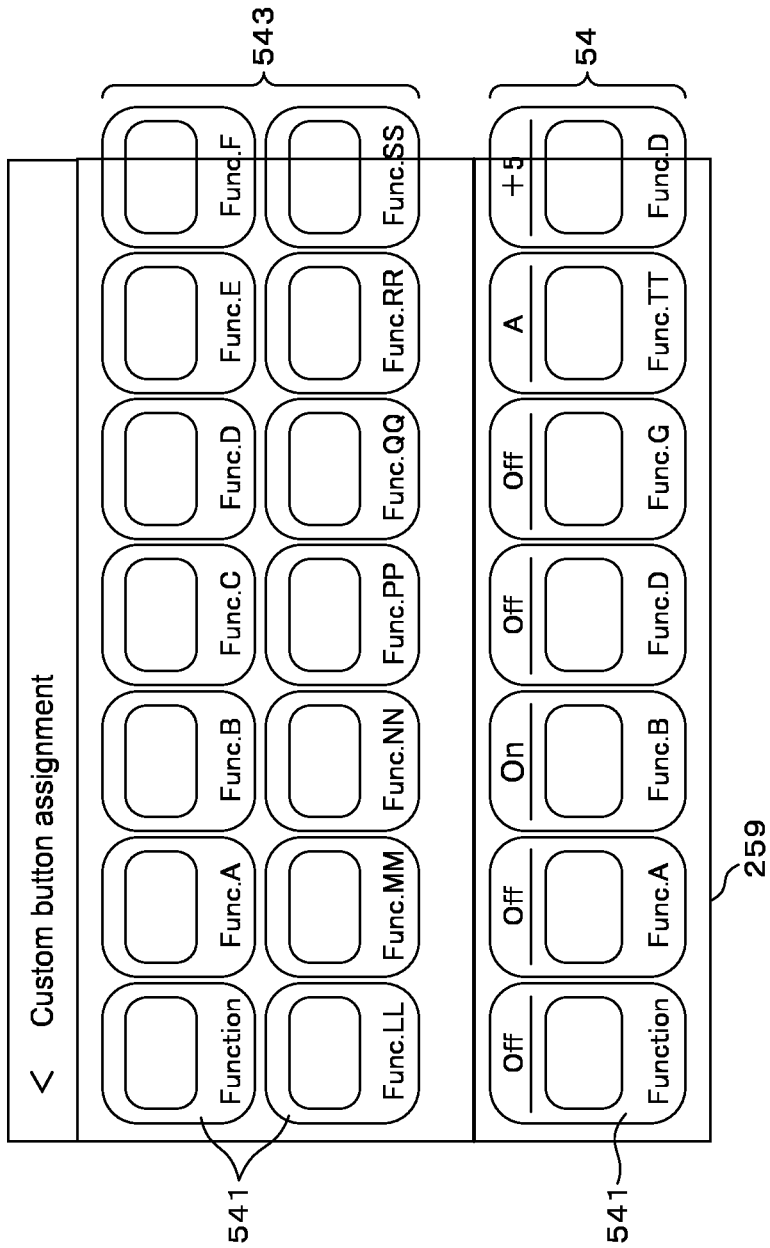
FIG. 37 illustrates the custom button region editing screen.

The user releases the finger from the touch panel 25 at a desired position and cancels the selection of the custom button 541. As shown in FIG. 37, the control unit 21 inserts the custom button 541 of "Func. D" having been selected to the position of the insertion marker 544. As such, the user can change the arrangement order of the custom buttons 541 to a desired order. Hence, the control unit 21 functions as a custom button selection acceptance unit and an arrangement order change acceptance unit.

Figure 38:
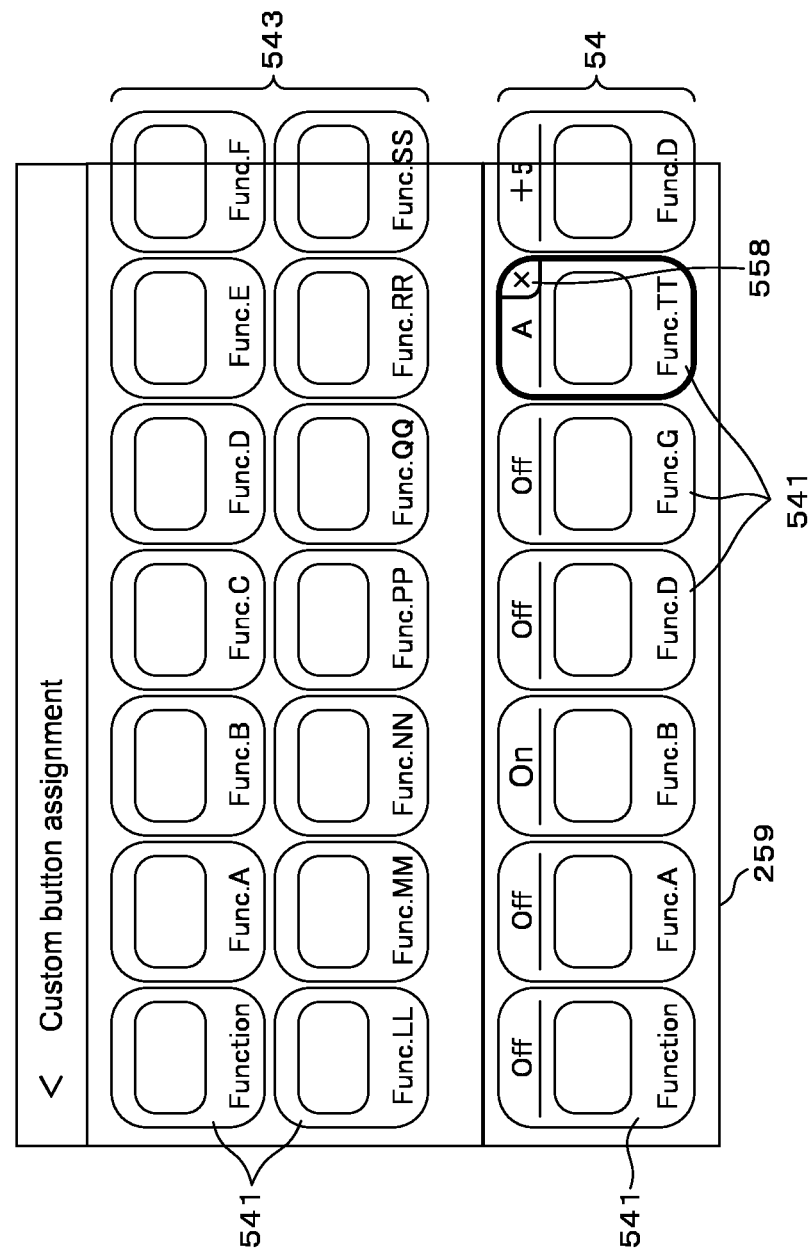
FIG. 38 illustrates the custom button region editing screen.

If the user presses and holds any of the custom buttons 541 within the custom button region 54, the control unit 21 accepts a selection of the custom button 541. In FIG. 38, the control unit 21 represents the custom button 541 of "Func. TT" of which the control unit 21 has accepted a selection by the bold mark.

Figure 39:
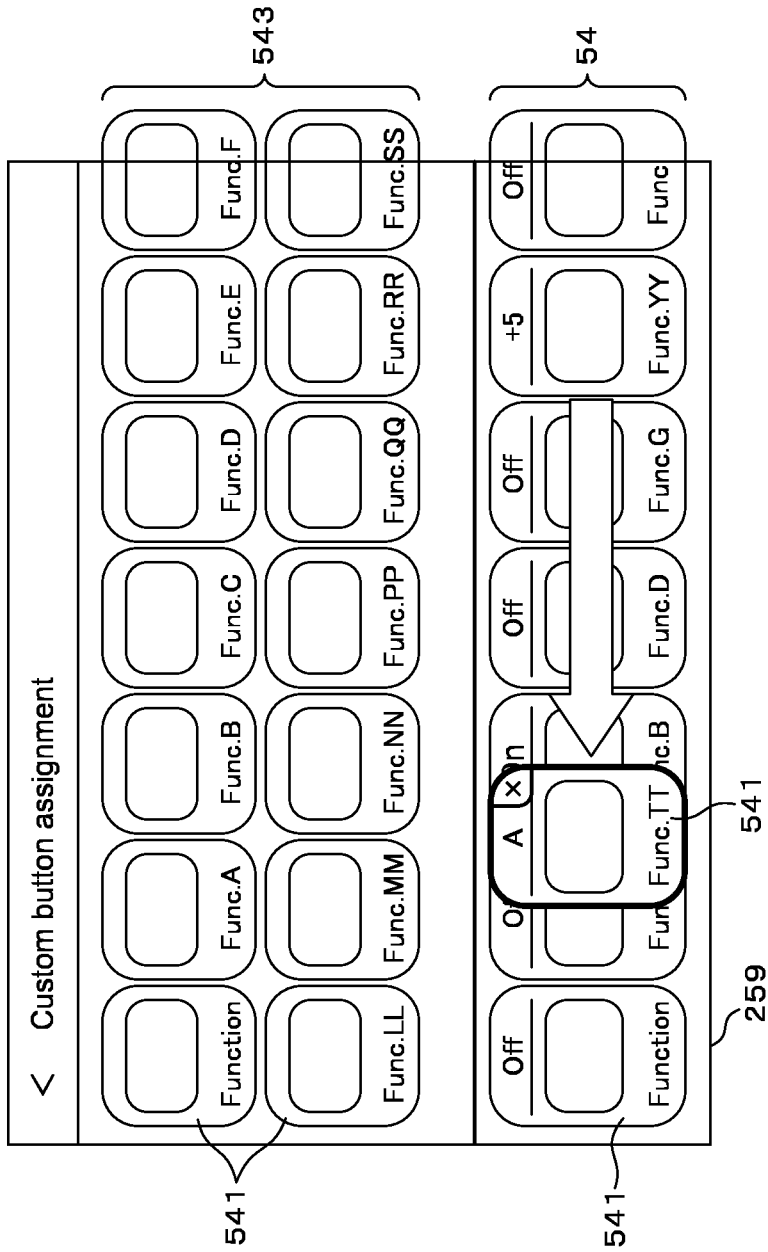
FIG. 39 illustrates the custom button region editing screen.

As shown by the hollow arrow in FIG. 39, the user slides a finger with the custom button 541 selected. The control unit 21 moves the selected custom button 541 to follow the finger movement of the user as shown in FIG. 39.

Figure 40:
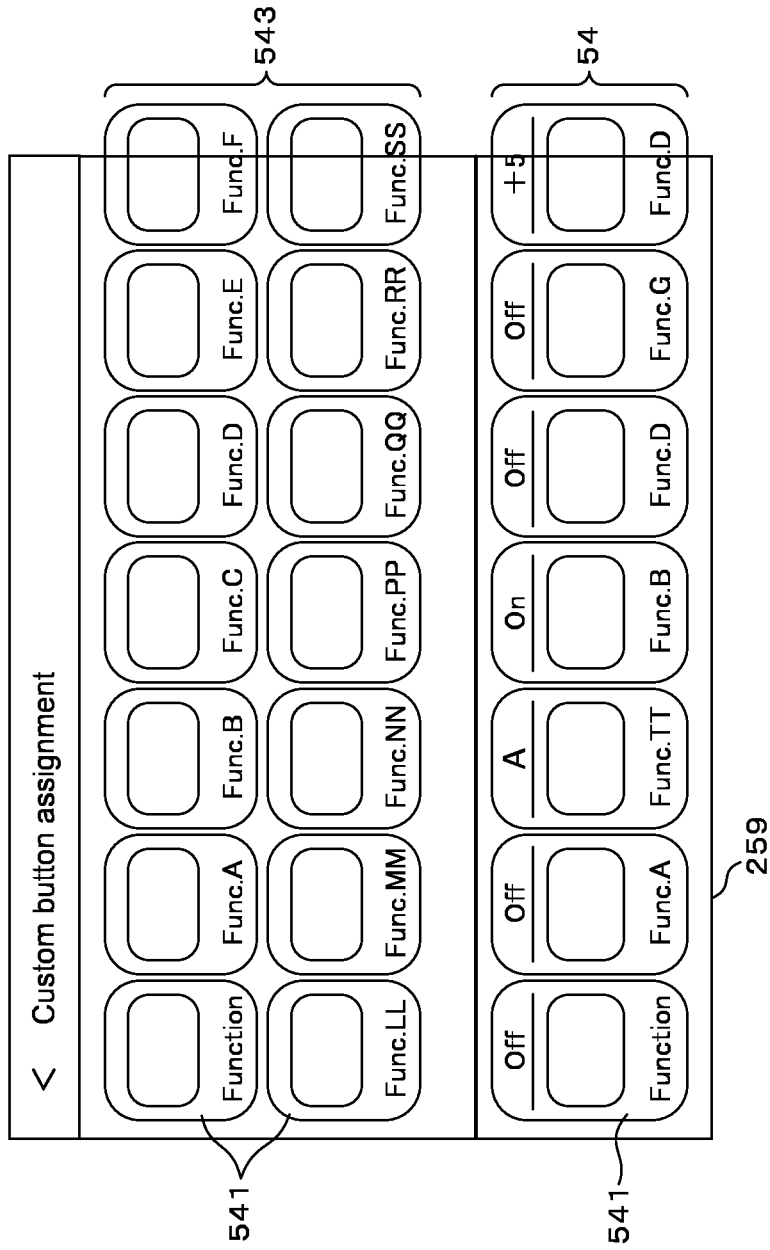
FIG. 40 illustrates the custom button region editing screen.

The user releases the finger from the touch panel 25 at a desired position and cancels the selection of the custom button 541. As shown in FIG. 40, the control unit 21 inserts the custom button 541 of "Func. Tt" having been selected to the position between the custom button 541 of "Func. A" and the custom button 541 of "Func. B."

Figure 41:
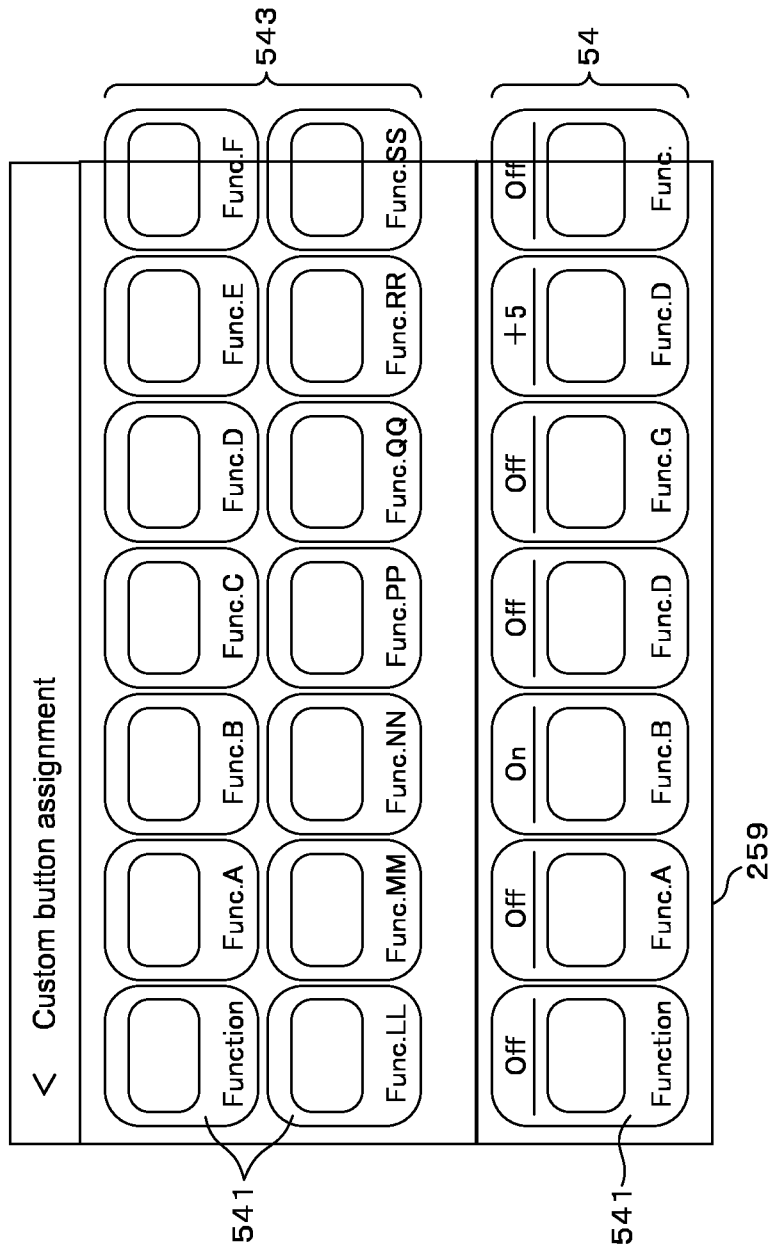
FIG. 41 illustrates the custom button region editing screen.
Figure 42:
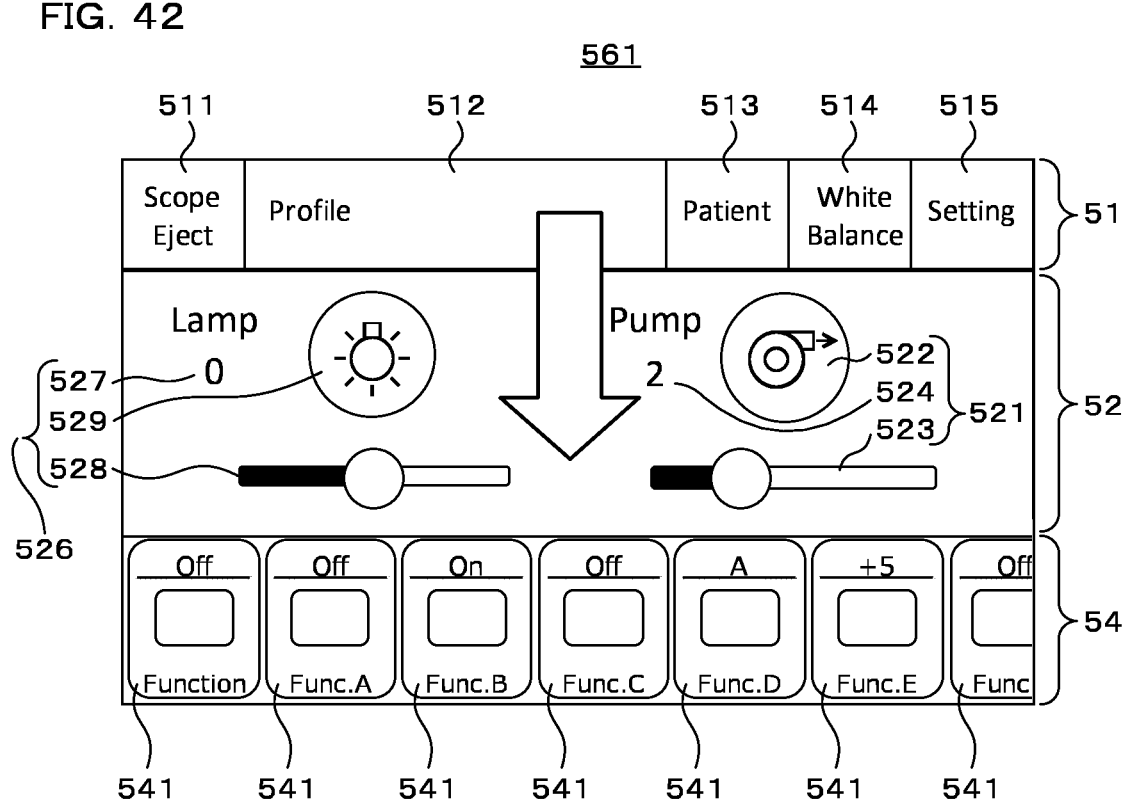
FIG. 42 illustrates a screen locking operation.

Returning to FIG. 38, if accepting a selection of any custom button 541 within the custom button region 54, the control unit 21 displays the delete button 558 at the upper right of the custom button 541 as shown in FIG. 38. If the user selects the delete button 558, the control unit 21 deletes this custom button 541 from the custom button region 54. FIG. 41 shows a state in which the custom button 541 of "Func. TT" is deleted.

The control unit 21 updates the profile field of the profile DB 71 described with reference to FIG. 5 or 6 such that it reflects the setting or the like accepted via the select menu setting screen 567 and the custom button region editing screen 568. If the same user performs endoscopy or if endoscopy is performed for the same purpose, the user can use the endoscope processor 20 at an operable setting depending on the situation by reading the settings from the profile DB 71.

The profile DB 71 having been stored in a file server connected to the HIS may be referred to through a network every time the profile list screen 564 is displayed or every time a selection of the profile by the user is accepted. For example, in a medical institution possessing multiple endoscope processors 20 of the same model, the user can use any endoscope processor 20 in the same procedure.

The profile DB 71 may be stored in an external file server. The user who performs endoscopy in multiple medical institutions can use the endoscope processor 20 in the same procedure even in any medical institution.

Returning to FIG. 23, the custom button 541 corresponding to the function with the advance button 571 like the "PIP" function may have been prepared.

If such a custom button 541 is selected, the control unit 21 displays a menu on which buttons or the like required for operating the function are arranged in the custom button region 54 on the top screen 561. If the custom button 541 corresponding to "PIP" function is selected, for example, the control unit 21 arranges in the custom button region 54 a total of four buttons respectively corresponding to "Off" and "On" buttons in FIG. 22 and "upper right" and"1:1" buttons. The buttons here may be a pull-down menu format, for example. This makes it possible to present a number of options to the user in a relatively small space.

As such, the control unit 21 functions as a menu display unit according to the present embodiment that displays a menu when accepting a control of the custom button.

FIGS. 42 to 45 illustrate a screen locking operation. The screen locking operation is an operation of setting the touch panel to a locked state, that is, a state incapable of accepting a user operation.

Figure 43:
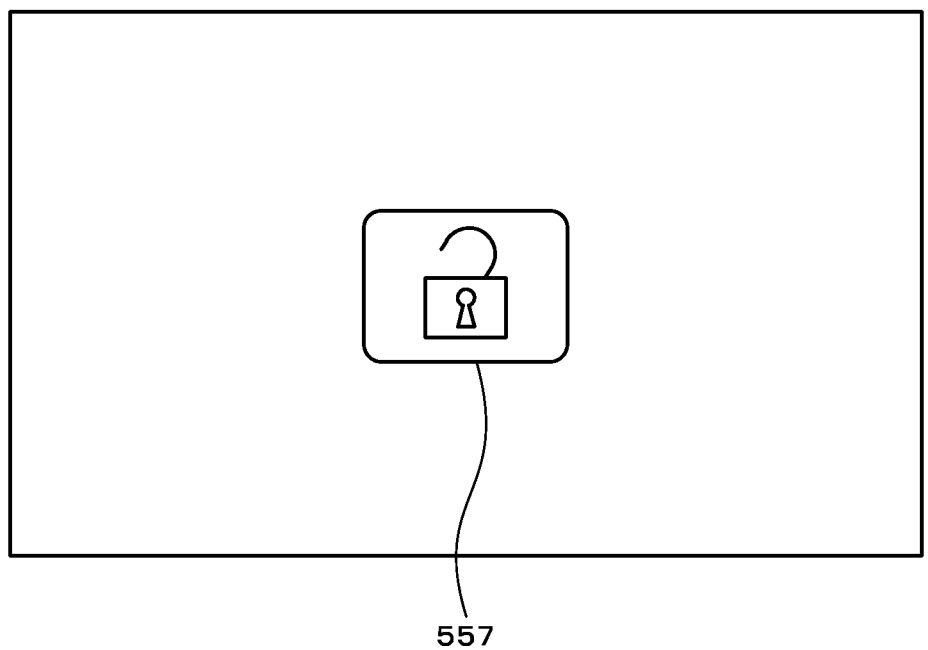
FIG. 43 illustrates the screen locking operation.

A screen shift from an unlocked state is described. If the user performs a swipe operation on the top screen 561 from top to bottom as represented by the hollow arrow in FIG. 42, the control unit 21 largely displays a lock button 557 in an unlocked state at the center of the touch panel 25 as shown in FIG. 43.

Figure 44:
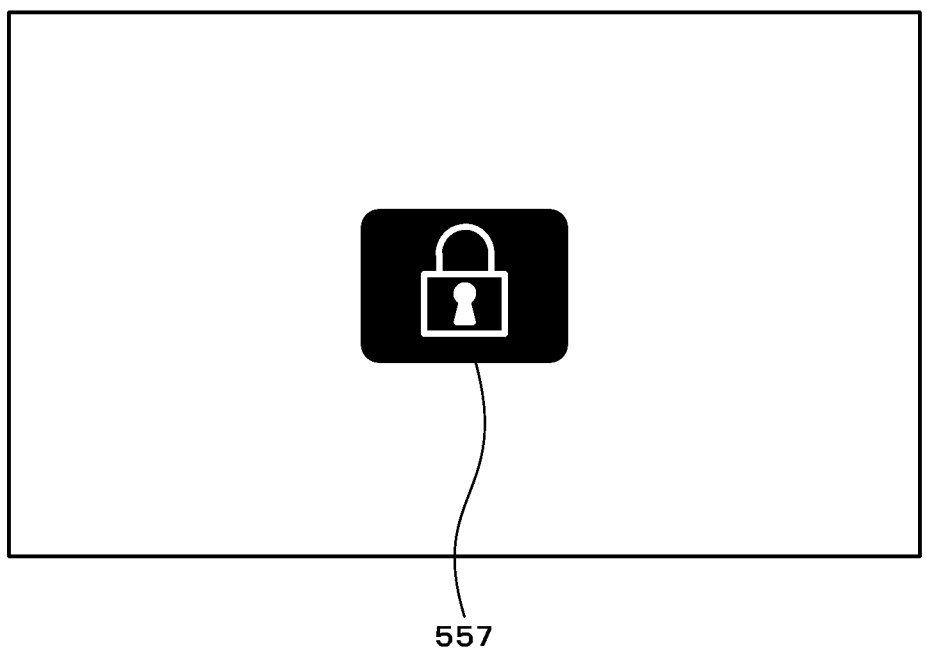
FIG. 44 illustrates the screen locking operation.
Figure 45:
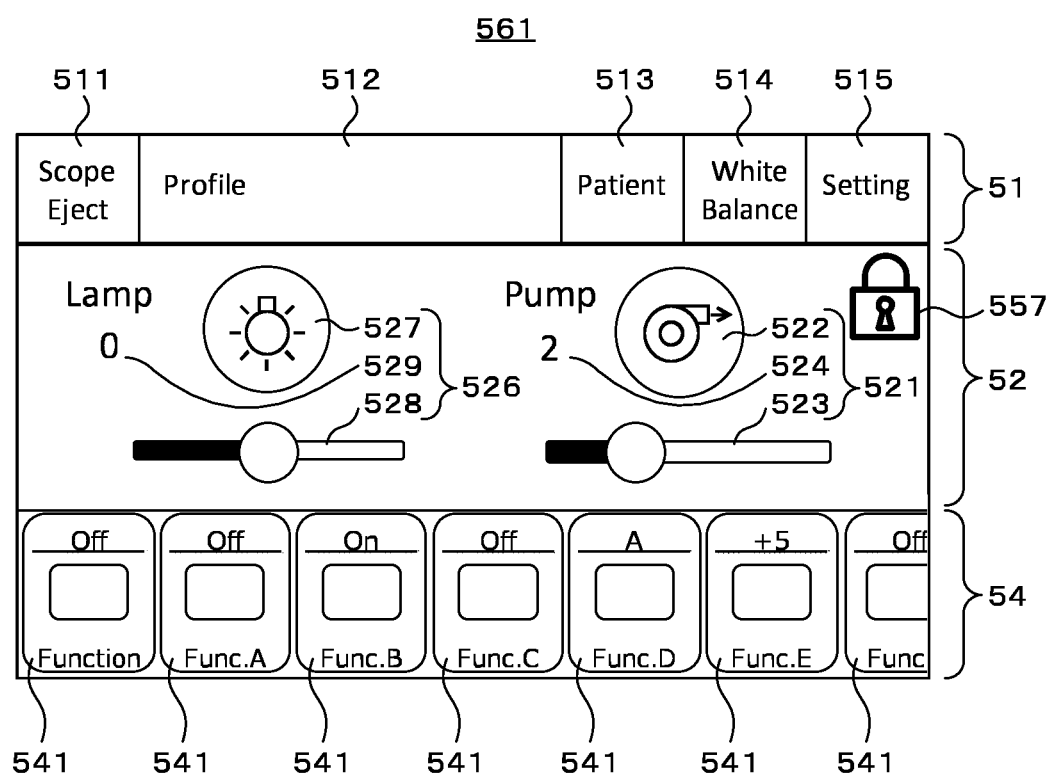
FIG. 45 illustrates the screen locking operation.

If the user presses and holds the lock button 557, the control unit 21 changes the state of the lock button 557 in a locked state as shown in FIG. 44. Then, the control unit 21 shifts the screen to a state in which the lock button 557 is displayed at the peripheral edge portion of the top screen 561 as shown in FIG. 45. In the following description, the state in which the lock button 557 is displayed at the peripheral edge of the top screen 561 is described as a locked state.

The screen shift will be described. In the locked state, the control unit 21 does not accept any operation on the touch panel 25 other than a tap operation performed on the lock button 557. By the screen shift to the lock state, the control unit 21 functions as an acceptance stop unit that stops accepting an operation.

If the user taps on the lock button 557, the control unit 21 displays the screen described with reference to FIG. 44 on the touch panel 25 for several seconds. If the user presses and holds the lock button 557 during this several seconds, the control unit 21 displays the screen described with reference to FIG. 43 on the touch panel 25. Then, the control unit 21 displays the top screen not including the lock button 557 to restart an acceptance of an operation via the touch panel 25. As such, the control unit 21 functions as an acceptance restart unit that cancels the locked state and restarts an acceptance of an operation.

If several seconds have elapsed without pressing and holding the lock button 557 on the screen described with reference to FIGS. 43 and 44, the control unit 21 displays the top screen in the initial locked state.

The user can perform endoscopy even if the touch panel 25 is in the locked state. This makes it possible to prevent changes in the settings of the endoscope processor 20 occurring due to an accidental response of the touch panel 25 such as a case where the universal cord 49 makes contact with the touch panel 25 during the endoscopy, for example.

Even if the touch panel 25 is in the locked state, the user can operate the endoscope processor 20 using the control buttons 431 and the foot switch 17. If the foot switch 17 is assigned the lamp adjustment switch 528, for example, the user can control the output level of the light source 33 by using the foot switch 17. The control unit 21 displays the output level of the light source 33 operated via the foot switch 17 at the lamp adjustment switch 528 of the touch panel 25.

As such, the control unit 21 reflects a result obtained by operating the endoscope processor 20 using the foot switch 17 or the like on the display of the touch panel 25 even if the touch panel 25 is in the locked state.

Since a swipe operation from up to bottom is used for shifting the touch panel 25 to the locked state, the touch panel 25 is prevented from being accidentally set to the locked state due to, for example, a contact by the universal cord 49 or a nearby medical staff or the like.

If accepting a swipe operation on the screen other than the top screen 561 such as the setting screen 566, the select menu setting screen 567 or the like, the control unit 21 may shift the touch panel 25 to the lock screen or neglect the swipe operation. The operation may be set using the setting screen 566.

Figure 46:
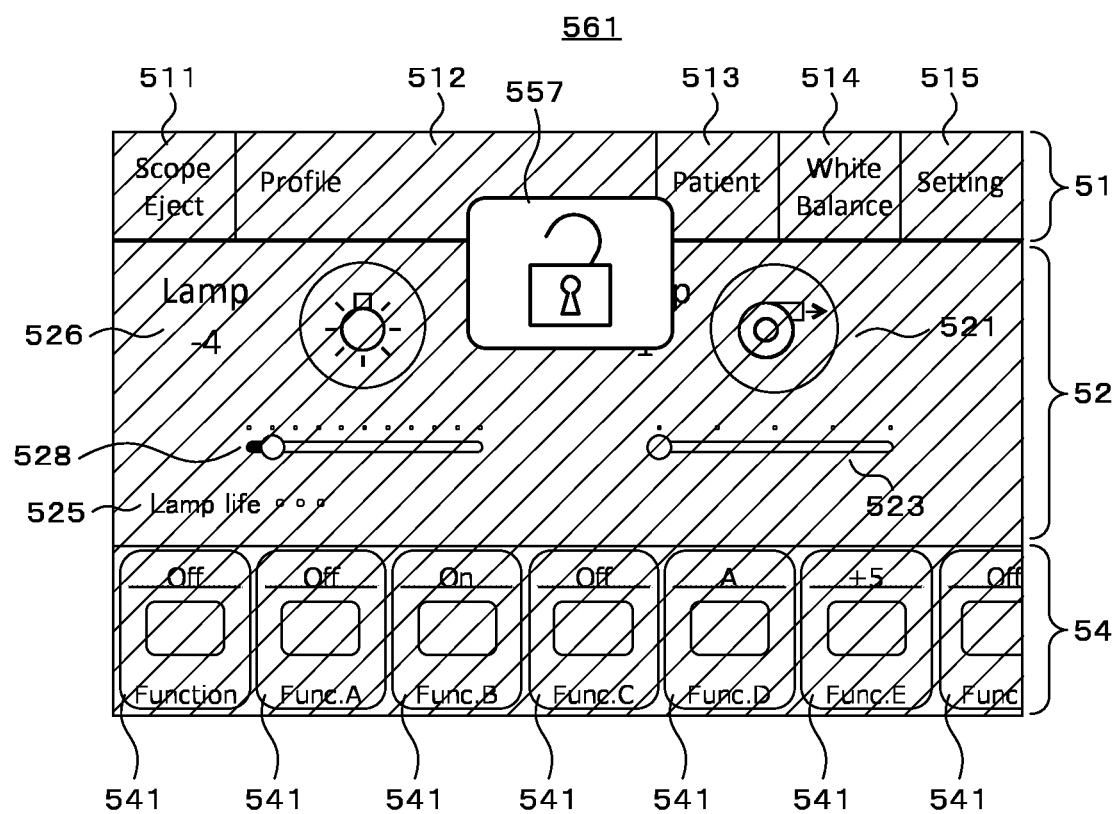
FIG. 46 illustrates a modification of the screen locking operation.
Figure 47:
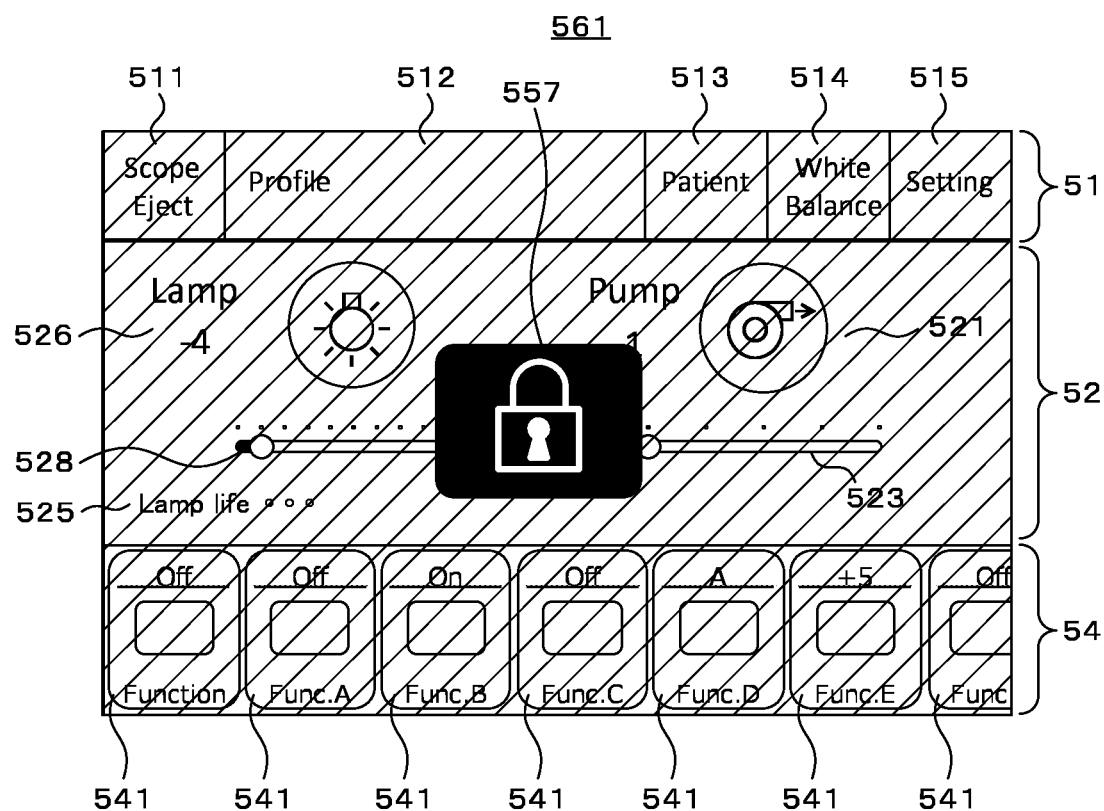
FIG. 47 illustrates a modification of the screen locking operation.
Figure 48:
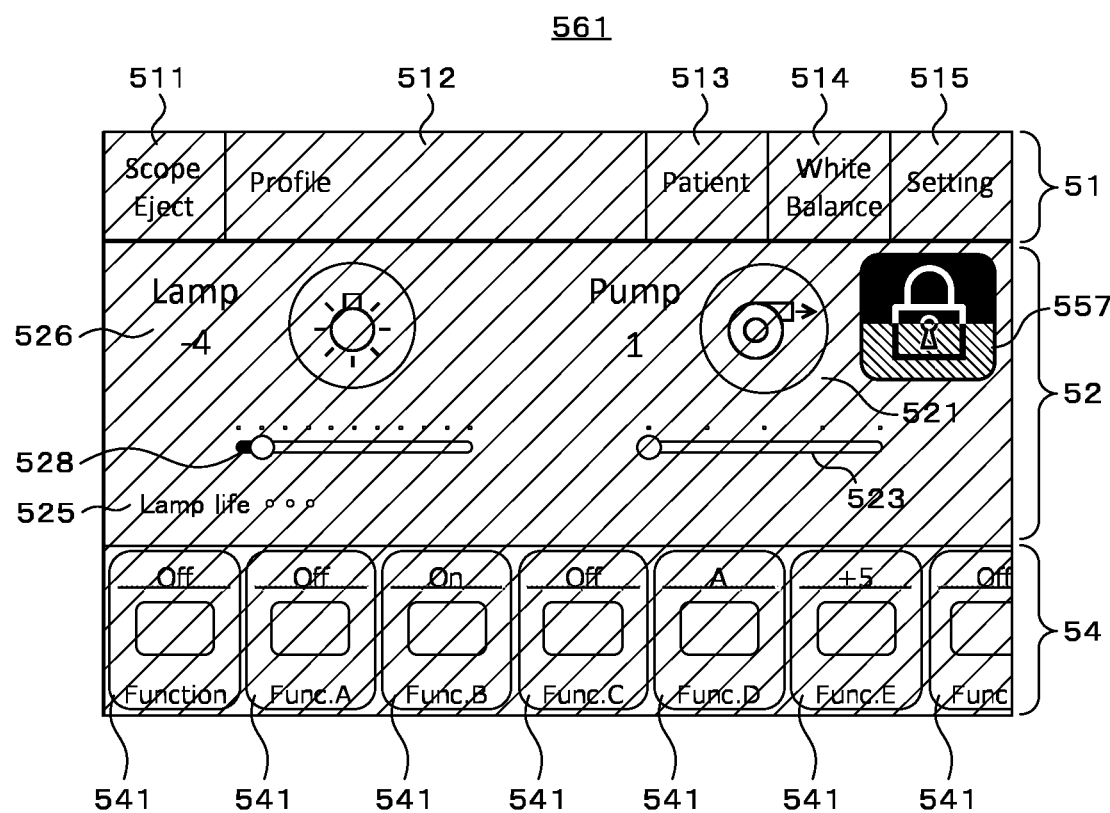
FIG. 48 illustrates a modification of the screen locking operation.

FIGS. 46 to 48 illustrate a modification of the screen locking operation. FIG. 46 is a modification of a screen obtained when a swipe operation is being made as described with reference to FIG. 42. If detecting the start of a swipe operation, the control unit 21 displays the lock button 557 in an unlocked state at a position slightly above the portion touched by the user's finger on the touch panel 25. The control unit 21 moves the lock button 557 to follow the movement of the user's finger.

Moreover, the control unit 21 displays the part other than the lock button 557 at low brightness when displaying the lock button 557. The hatching shows the low-brightness part in FIG. 46. This allows the user to more easily recognize the start of a screen locking operation.

The lock button 557 is displayed during a swiping operation, so that the user can easily find the start of a screen locking operation. The user quickly releases the finger from the touch panel 25 if not intending to perform a screen locking operation. If the user releases the finger from the screen before completion of a swipe operation of a predetermined length, the control unit 21 stops the screen locking operation and returns the screen to the original brightness.

The user can confirm the start of the screen locking operation while performing a swipe operation, so that the control unit 21 may set the touch panel 25 as being in the locked state immediately after the completion of the swipe operation without performing acceptance of a press and hold operation of the lock button 557 described with reference to FIG. 43. If acceptance of a press and hold operation is not performed, the lock button 557 functions as a lock icon visually showing the locked state.

FIG. 47 is a modification of the screen at a completion of the swipe operation described with reference to FIG. 44. If detecting the start of a swipe operation, the control unit 21 displays the lock button 557 in a locked state in the center portion of the top screen 561. The lock button 557 displayed during a swipe operation functions as a lock icon that visually shows that a shift operation to the locked state is in progress. The control unit 21 functions as a lock icon display unit that displays the lock icon.

The control unit 21 may continuously display the screen shown in FIG. 47 even after completion of the swipe operation and shifting to the locked state. In other words, the control unit 21 may display the lock button 557 in the center of the touch panel 25 during the locked state. Thus, the endoscope processor 20 can be provided that allows the user to easily find the locked state and perform an unlocking operation.

With reference to FIG. 48, a modification of a screen unlocking operation is described. In the locked state in the present modification, the control unit 21 does not accept an operation on the touch panel 25 other than a press and hold operation performed on the lock button 557.

If the user presses and holds the lock button 557, the control unit 21 changes the color of the lock button 557 gradually from bottom to top. The control unit 21 entirely changes the color of the lock button 557 and deletes the lock button 557 to thereby cancel the screen locking. Then, the control unit 21 restarts acceptance of an operation via the touch panel 25. In the description below, releasing the screen locking is described as unlocking.

The user can confirm the progress of unlocking by change of the lock button 557. For example, if the user stops pressing and holding the lock button 557 before the color of the lock button 557 is entirely changed, the control unit 21 interrupts the unlocking processing.

The operations of locking and unlocking of the screen as described with reference to FIGS. 42 to 48 are mere examples. For example, the control unit 21 may accept a screen locking operation by any operation such as a predetermined number of tap operations, a predetermined number of flip operations in a predetermined direction or the like in place of a swipe operation.

The control unit 21 may accept a screen locking operation and a screen unlocking operation by voice recognition. The control unit functions as a voice stop instruction acceptance unit and a voice start instruction acceptance unit. The control unit 21 may accept detailed settings concerning a screen locking operation and a screen unlocking operation via the setting screen 566.

Figure 49:
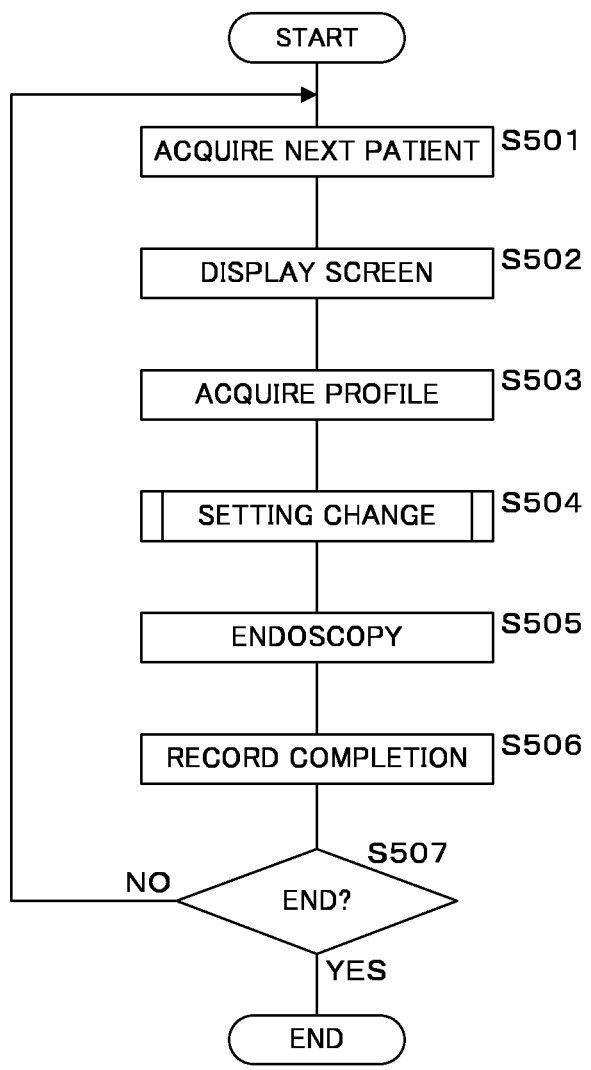
FIG. 49 is a flowchart showing a flow of the processing of a program.

FIG. 49 is a flowchart showing a flow of the processing of a program. The control unit 21 acquires a record associated with a patient who is scheduled to take endoscopy next from the patient DB 72 (step S501). More specifically, the control unit 21 acquires the record having the smallest numerical value in the order field out of the records containing "N" in the complete field.

The control unit 21 displays the information such as a patient name or the like recorded in the record acquired at step S501 at the patient section 64 of the screen displayed on the display device 50 described with reference to FIG. 8 (step S502). The user confirms that the patient that is being displayed at the patient section 64 matches the patient who is scheduled to actually take endoscopy next. If they do not match, the user selects the patient button 513 to display the patient list screen 562 described with reference to FIG. 16. The user selects a correct patient on the patient list screen 562.

The control unit 21 acquires a profile to be used in the next endoscopy from the profile DB 71 (step S503). More specifically, the control unit 21 waits for the user selecting the profile button 512 to display the profile list screen 564 and for selecting a profile. If the user does not select a profile, the control unit 21 uses the profile used in the previous endoscopy.

If the patient DB 72 contains a field to record information related to a profile such as the name of a doctor who is in charge of endoscopy, the purpose of the endoscopy or the like, the control unit 21 searches the profile DB 71 using the field as a key and acquires the profile.

The control unit 21 starts a subroutine for setting changes (step S504). The subroutine for setting changes is a subroutine for changing the settings of the endoscope processor 20 based on the acquired profile. The flow of processing of the subroutine for setting changes will be described later.

The user performs endoscopy using the endoscope 40. During the endoscopy, the control unit 21 executes processing such as control of the imaging element provided at the head portion 443 of the control unit 21, generation of an endoscopic image and display of the image on the display device 50 and the like (Step S505). The processing performed by the control unit 21 during the endoscopy is similar to the conventional processing, and thus the detailed description is not repeated.

After completion of the endoscopy, the control unit 21 records "Y" indicating the completion of the endoscopy in the complete filed of the record associated with the patient who has taken endoscopy in the patient DB 72 (step S506). The control portion 21 determines whether or not endoscopy of the patients recorded in the patient DB 72 has been finished (step S507). More specifically, if there remains any record containing "N" in the complete field, the control unit 21 determines that the endoscopy has not yet been finished.

If determining that the endoscopy has not yet been finished (NO at step S507), the control portion 21 returns the process to step S501. If determining that the endoscopy has been finished (YES at step S507), the control portion 21 ends the processing.

Figure 50:
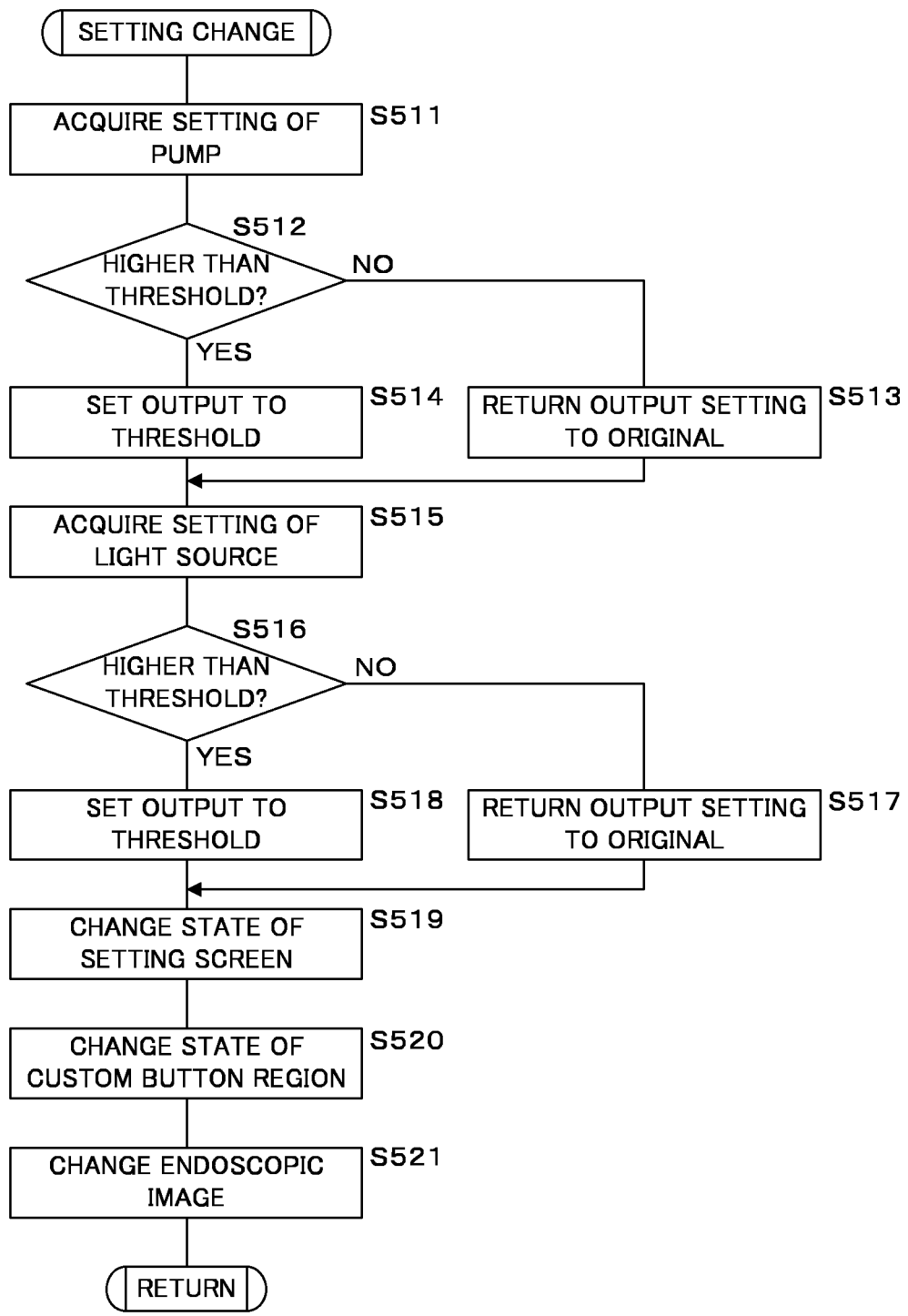
FIG. 50 is a flowchart showing a flow of the subroutine for setting changes.

FIG. 50 is a flowchart showing a flow of the subroutine for setting changes. The subroutine for setting changes is a subroutine for changing the settings of the endoscope processor 20 based on the acquired profile.

The control unit 21 acquires the setting of the pump setting region 521 at the completion of the previous use that has been stored in the nonvolatile memory (step S511). It is noted that if the setting of the pump setting region 521 has been recorded in the profile, the control unit 21 acquires the setting of the pump setting region 521 from the profile.

The control unit 21 determines whether or not the acquired setting of the pump adjustment switch 523 is higher than a predetermined threshold (step S512). If determining that the setting is not higher than the threshold (NO at step S512), the control unit 21 returns the setting of the pump adjustment switch 523 to the state acquired at step S511 (step S513). If determining that the setting is higher than the threshold (YES at step S512), the control unit 21 sets the pump adjustment switch 523 to the threshold (step S514).

After completion of the step S513 or S514, the control unit 21 acquires the setting of the lamp setting region 526 at the completion of the previous use that has been stored in the nonvolatile memory (step S515). It is noted that if the setting of the lamp setting region 526 has been recorded in the profile, the control unit 21 acquires the setting of the lamp setting region 526 from the profile.

The control unit 21 determines whether or not the acquired setting of the lamp adjustment switch 528 is higher than a predetermined threshold (step S516). If determining that the setting is not higher than the threshold (NO at step S516), the control unit 21 returns the setting of the lamp adjustment switch 528 to the state acquired at step S515 (step S517). If determining that the setting is higher than the threshold (YES at step S516), the control unit 21 sets the lamp adjustment switch 528 to the threshold (step S518).

After completion of the step S517 or S518, the control unit 21 changes the state of the setting screen 566 based on the profile (step S519). The control unit 21 changes the custom buttons 541 to be displayed on the custom button region 54 on the top screen 561 based on the profile (step S520). By the step S520, the control unit 21 functions as a custom button display unit according to the present embodiment.

The control unit 21 changes the settings for the image processing of the endoscopic image based on the profile (S521). Thereafter, the control portion 21 ends the processing.

As such, the endoscope processor 20 can be provided that starts with the setting modified to the predetermined threshold in the case where the output of the pump 34 or the light source 33 is set to a maximum at the completion of the previous use.

It is noted that the subroutine for setting changes is not limited to the subroutine described with reference to FIG. 50. For example, the control unit 21 may acquire the setting of the pump setting region 521 at the completion of the previous use at step S511 and then automatically return the setting of the pump adjustment switch 523 without performing the determination at step S512.

Likely, the control unit 21 may acquire the setting of the lamp setting region 526 at the completion of the previous use at step S515 and then automatically return the setting of the lamp adjustment switch 528 without performing the determination at step S516. As such, the endoscope processor 20 can be provided that starts at the settings the same as those at the completion of the previous use.

According to the present embodiment, the endoscope processor 20 can be provided that allows the user to promptly adjust the function by using the touch panel 25.

According to the present embodiment, the endoscope processor 20 can be provided that allows the user to easily adjust the pressure of the pump 34 and the brightness of the light source 33. The user can intuitively operate the pressure of the pump 34 and the brightness of the light source 33 by a sliding operation described with reference to FIG. 9. The user can adjust the pressure of the pump 34 and the brightness of the light source 33 little by little by a tap operation without tapping on the precise position described with reference to FIG. 10.

According to the present embodiment, since text is displayed at the pump level section 524 and the lamp level section 529, the doctor who is using the endoscope 40 can provide a nurse or a medical technician with explicit instruction in the case where the doctor verbally instructs them about the operation.

According to the present embodiment, the endoscope processor 20 can be provided that allows the user to promptly grasp the function and the state of the function and to easily operate by using the custom button 541. By tapping on the custom button 541 multiple times, the user can set each of the functions to a desired state According to the present embodiment, since the custom buttons 541 have the same size, the custom buttons 541 can be aligned along the periphery of the touch panel 25. Since the custom buttons 541 are aligned, the endoscope processor 20 can be provided that allows the user to easily find a target custom button 541 and operate the button.

According to the present embodiment, the endoscope processor 20 can be provided to which the name or the like of a patient who takes endoscopy next is easily settable.

According to the present embodiment, the endoscope processor 20 can be provided that allows the user to promptly perform an operation for a setting change by collecting the frequently-used settable items to the select menu screen. The endoscope processor 20 can be provided that allows the user to easily select the settable items displayed on the select menu screen using the option button 559.

According to the present embodiment, the endoscope processor 20 can be provided that prevents setting changes unintentionally performed by the user or the like from occurring by locking the touch panel 25.

Embodiment 2

The present embodiment relates to a portable endoscope processor 20. Components overlapping those of Embodiment 1 are not described here.

Figure 51:
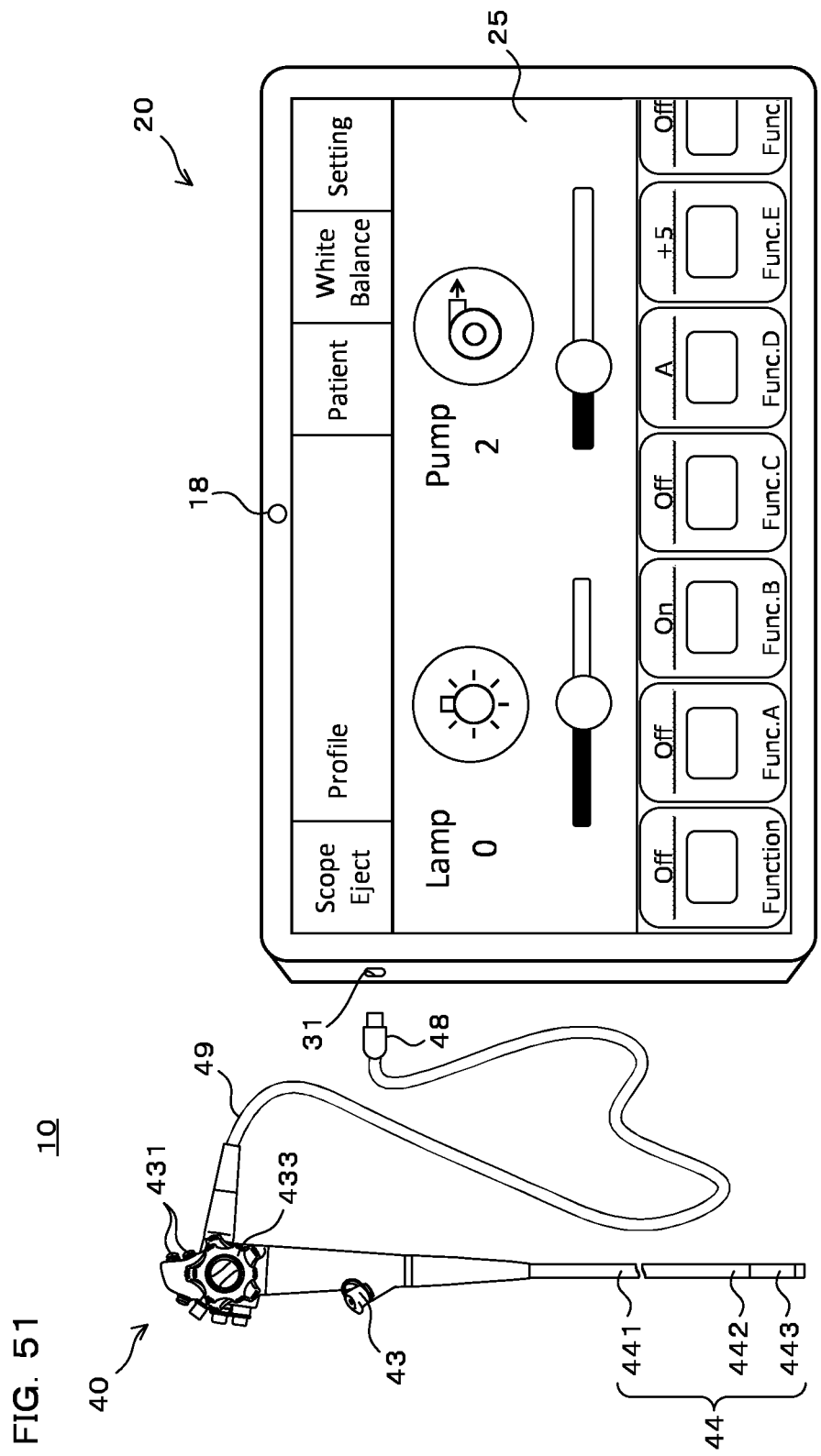
FIG. 51 illustrates an external appearance of an endoscope system according to Embodiment 2.

FIG. 51 illustrates an external appearance of an endoscope system 10 according to Embodiment 2. The endoscope processor 20 according to the present embodiment is tablet-typed. The endoscope processor 20 is approximately entirely covered with the touch panel 25 on its surface. In addition to the top screen 561 and the like, the endoscopic image described with reference to FIG. 8 is also displayed on the touch panel 25.

An endoscope connector 31 is disposed at a side surface of the endoscope processor 20. At the periphery of the touch panel 25, a camera 18 is disposed. The camera 18 is used for face recognition of the user, for example. The face recognition has conventionally been employed, and thus the detailed description is not made here.

The endoscope 40 according to the present embodiment is an endoscope for the respiratory organs without provision of an air/water supply function. The scope connector 48 may be a general-purpose connector such as a USB connector, for example.

Figure 52:
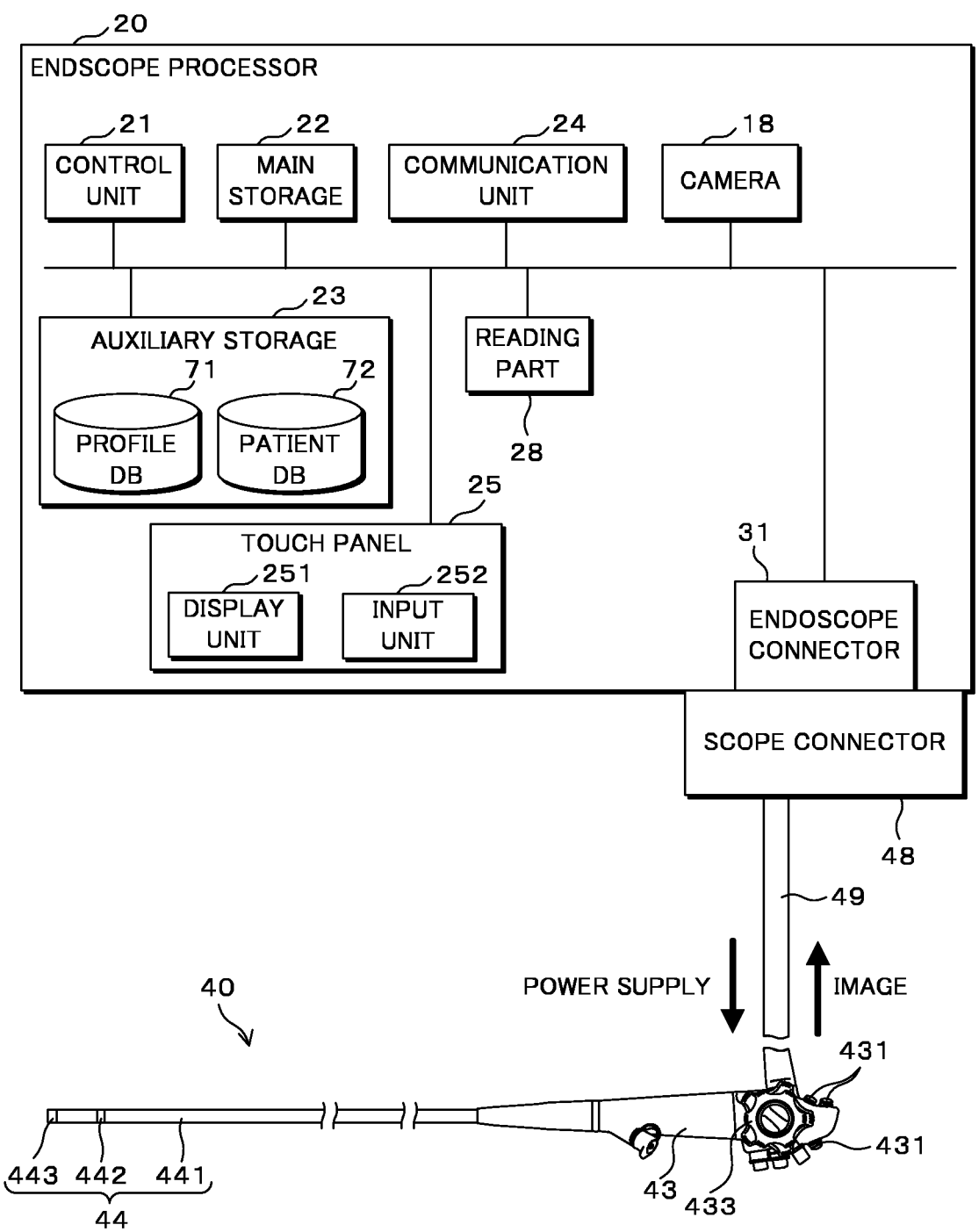
FIG. 52 illustrates the configuration of the endoscope system according to Embodiment 2.

FIG. 52 illustrates the configuration of the endoscope system according to Embodiment 2. The endoscope system 10 includes the endoscope processor 20 and the endoscope 40. The endoscope processor 20 is provided with the camera 18, the control unit 21, the main storage 22, the auxiliary storage 23, the communication unit 24, the touch panel 25, the reading part 28, the endoscope connector 31 and the buses. The respective components are similar to those of Embodiment 1, and thus the description thereof is not made here. It is noted that the endoscope connector 31 may also serve as the reading part 28.

At the head portion 443 of the endoscope 40, the LED for illumination and the imaging element are disposed. In other words, the endoscope 40 receives power supply from the endoscope processor 20 to thereby emit illumination light from the LED and provides the endoscope processor 20 with an image signal captured by the imaging element.

It is noted that the endoscope processor 20 may have the pump 34. With the use of the scope connector 48 that can be connected to an air/water supply tube as well as a contact point for electric connection, the endoscope processor 20 can be provided that is usable in combination with the endoscope 40 having an air/water supply function.

The endoscope processor 20 may control an externally attached pump 34 while the endoscope 40 may have a connector that is connectable to the externally attached pump 34 as well as the scope connector 48 to be connected to the endoscope processor 20.

The control unit 21 switches the screen to be displayed on the touch panel 25 based on the operation by the user. For example, the user can instruct the screen to be displayed on the touch panel 25 by a double tap operation or a voice operation by the user.

According to the present embodiment, a small and portable endoscope system 10 can be provided that is usable in a visiting medical examination and a bedside examination in an inpatients' ward, for example.

Embodiment 3

Figure 53:
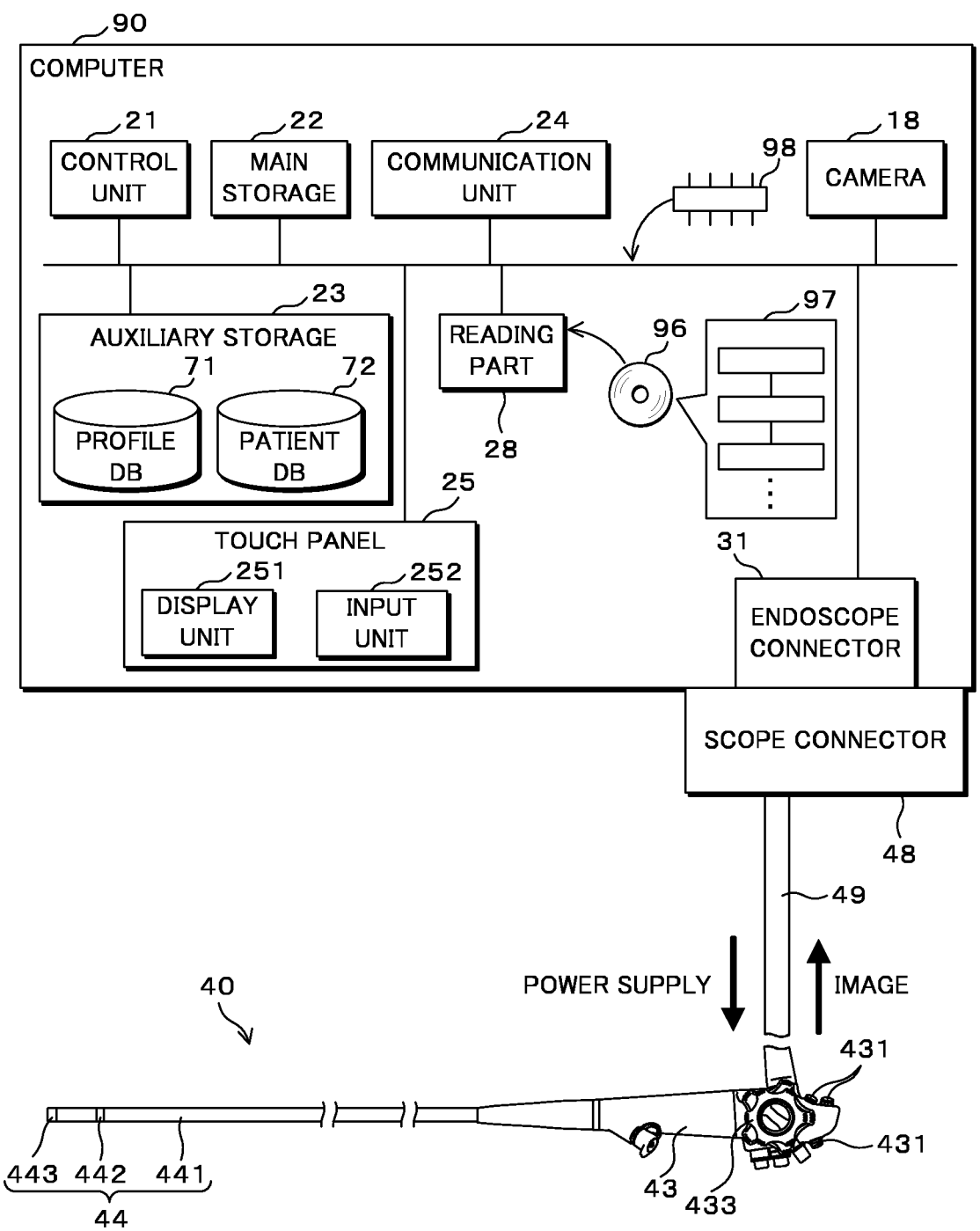
FIG. 53 illustrates the configuration of an endoscope system according to Embodiment 3.

FIG. 53 illustrates the configuration of an endoscope system according to Embodiment 3. The present embodiment relates to a mode achieving an endoscope system 10 according to the present embodiment by generating a general-purpose computer 90 and a program 97 in combination. Components overlapping those of Embodiment 2 are not described here.

The endoscope system 10 according to the present embodiment includes the computer 90 and the endoscope 40. The computer 90 is provided with the camera 18, the control unit 21, the main storage 22, the auxiliary storage 23, the communication unit 24, the touch panel 25, the reading part 28 and the buses. The computer 90 is an information appliance such as a general-purpose personal computer, a tablet, a smart phone or the like.

The program 97 is recorded in a movable recording medium 96. The control unit 21 reads the program 97 via the reading part 28 and stores the same in the auxiliary storage 23. Alternatively, the control unit 21 may read the program 97 stored in a semiconductor memory 98 such as a flash memory or the like mounted on the computer 90. Alternatively, the control unit 21 may download the program 97 from another server computer (not illustrated) connected via the communication unit 24 and a network (not illustrated) and store the same in the auxiliary storage 23.

The program 97 is installed as a control program of the computer 90, and loaded into the main storage 22 and executed. Thus, the computer 90 functions as the above-described endoscope processor 20 while the computer 90 and the endoscope 40 function as the above-described endoscope system 10.

Embodiment 4

Figure 54:
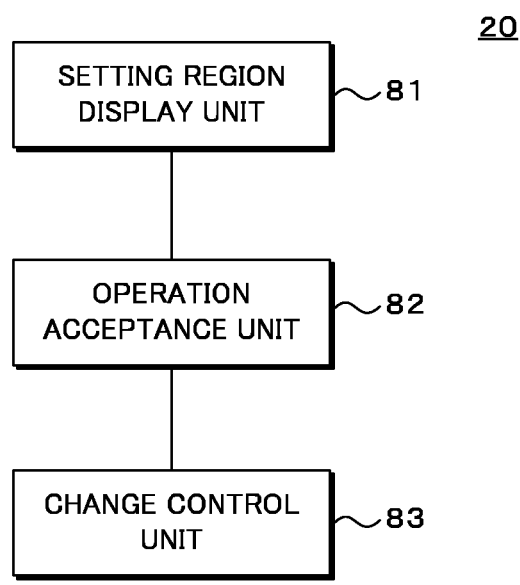
FIG. 54 is a functional block diagram of an endoscope processor according to Embodiment 4.

FIG. 54 is a functional block diagram of an endoscope processor 20 according to Embodiment 4. The endoscope processor is provided with a setting region display unit 81, an operation acceptance unit 82 and a change control unit 83. The setting region display unit 81 displays on the touch panel 25 the setting regions 521 and 526 including the on-off switches 522 and 527 for accepting switching between on and off states of the functions of the endoscope 40 and the adjustment switches 523 and 528 for accepting level adjustments of the functions.

The operation acceptance unit 82 accepts operations of the on-off switches 522 and 527 and the adjustment switches 523 and 528 that are displayed. The change control unit 83 changes the operating state of the function based on the accepted operation.

The technical features (elements) described in the embodiments can be combined with each other and can form a new technical feature by the combination.

It is to be understood that the embodiments disclosed here are illustrative in all respects and not restrictive. The scope of the present invention is defined by the appended claims, not by the above-mentioned meaning, and all changes that fall within the meanings and the bounds of the claims, or equivalence of such meanings and bounds are intended to be embraced by the claims.

A1. An endoscope processor comprising:
   a patient selection button display unit that displays a patient selection button on a touch panel; and
   a patient list display unit that displays a patient list on the touch panel if an operation performed on the patient selection button displayed is accepted.

A2. The endoscope processor according to clause A1, wherein
   the patient list is a table form in which an order of performing endoscopy, a patient ID and a patient name are associated with one another and includes a sort button that sorts the patient list based on each item of an order of performing endoscopy, a patient ID and a patient name.

A3. The endoscope processor according to clause A1 or A2, further comprising:
   a patient acceptance unit that accepts a selection of a patient from the patient list; and
   a display unit that displays information on a patient accepted by the patient acceptance unit together with an endoscopic image on a display device.

A4. The endoscope processor according to clause A3, wherein the display device is the touch panel.

A5. The endoscope processor according to clause A3, wherein the display device is a device separate from the endoscope processor that is externally connected to the endoscope processor.

A6. The endoscope processor according to any one of clauses A3 to A5, wherein
   display of the patient list is stopped if the patient acceptance unit accepts a selection of a patient, and the patient list in a state immediately before the display is stopped is redisplayed if an operation of the patient selection button is accepted again.

A7. The endoscope processor according to clause A6, wherein the patient list is redisplayed in a state where a patient a selection of which has been accepted by the patient acceptance unit is attached with a flag.

A8. The endoscope processor according to any one of clauses A3 to A5, wherein
   display of the patient list is stopped if the patient acceptance unit accepts a selection of a patient, and
   a patient list is displayed in a state where the patient a selection of which has been accepted is deleted from the patient list immediately before the display of the patient list is stopped if an operation of the patient selection button is accepted again.

A9. The endoscope processor according to any one of clauses A6 to A8, wherein the patient list is redisplayed in a state where a patient who takes endoscopy next to the patient a selection of which has been accepted by the patient acceptance unit.

A10. The endoscope processor according to any one of clauses A1 to A9, further comprising:
   a setting region display unit that displays on the touch panel a setting region where an on-off switch accepting switching between an on state and an off state of a function of an endoscope is combined with an adjustment switch accepting adjustment of a level of the function together with the patient selection button, an operation acceptance unit that accepts operations performed on the on-off switch and the adjustment switch, and a change control unit that changes an operating state of the function based on an accepted operation.

A11. A program causing a computer to execute the processing of displaying a patient selection button on a touch panel; and displaying a patient list on the touch panel if an operation performed on the patient selection button displayed is accepted.

A12. An information processing method causing the computer to execute the processing of:

displaying a patient selection button on a touch panel; and displaying a patient list on the touch panel if an operation performed on the patient selection button displayed is accepted.

B1. An endoscope processor comprising:

a setting button display unit that displays a setting button on a touch panel;

a button display unit that displays a first button and a second button on the touch panel if an operation of the setting button is accepted;

a second settable item display unit that displays on the touch panel a plurality of settable items respectively associated with option buttons on the touch panel if a selection of the second button is accepted;

a selection storage unit that accepts and stores a selection of one of the option buttons; and a first settable item display unit that displays a settable item having been selected by the option button on the touch panel if a selection of the first button is accepted.

B2. The endoscope processor according to clause B1, wherein a settable item corresponding to a button being selected is displayed on the touch panel in addition to the first button and the second button if an operation of the setting button is accepted.

B3. The endoscope processor according to clause B2, wherein the first button and the second button are displayed in tab form so as to be located at a periphery of the displayed settable item.

B4. The endoscope processor according to any one of clauses B1 to B3, wherein a plurality of the second buttons are displayed that are respectively associated with groups of settable items that are different from one another, and some of the settable items included in the group corresponding to a second button a selection of which is accepted are displayed so as to be respectively associated with the option buttons.

B5. The endoscope processor according to any one of clauses B1 to B4, further comprising a change acceptance unit that accepts an arrangement change of the displayed settable items if a selection of the first button is accepted.

B6. The endoscope processor according to any one of clauses B1 to B5, further comprising a delete acceptance unit that accepts deletion of the displayed settable items if a selection of the first button is accepted.

B7. The endoscope processor according to any one of clauses B1 to B6, wherein a setting option button accepting a setting change of each of the settable items is displayed.

B8. The endoscope processor according to any one of clauses B1 to B7, wherein a setting display section displaying a setting state of each of the settable items and an advance button accepting an instruction of displaying a detailed item concerning the settable item are displayed.

B9. The endoscope processor according to any one of clauses B1 to B8, comprising:

a setting region display unit that displays on the touch panel a setting region where an on-off switch accepting switching between an on state and an off state of a function of an endoscope is combined with an adjustment switch accepting adjustment of a level of the function together with the setting button;

an operation acceptance unit that accepts operations performed on the on-off switch and the adjustment switch; and a change control unit that changes an operating state of the function based on an accepted operation.

B10. An information processing method causing a computer to execute the processing of:

displaying a setting button on a touch panel;

displaying a first button and a second button on the touch panel if an operation of the setting button is accepted;

displaying on the touch panel a plurality of settable items respectively associated with option buttons on the touch panel if a selection of the second button is accepted;

accepting and storing a selection of one of the option buttons; and;

displaying a settable item having been selected by the option button on the touch panel if a selection of the first button is accepted.

B11. An information processing method causing a computer to execute the processing of:

displaying a setting button on a touch panel;

displaying a first button and a second button on the touch panel if an operation of the setting button is accepted;

displaying on the touch panel a plurality of settable items respectively associated with option buttons on the touch panel if a selection of the second button is accepted;

accepting and storing a selection of one of the option buttons; and;

displaying a settable item having been selected by the option button on the touch panel if a selection of the first button is accepted.

C1. An endoscope processor comprising a custom button region display unit that displays on a touch panel a custom button region where a plurality of custom buttons respectively associated with functions operable by a user are aligned.

C2. The endoscope processor according to clause C1, wherein the plurality of custom buttons have an equal size.

C3. The endoscope processor according to clause C1 or C2, further comprising a custom button selection acceptance unit that accepts a selection of any one of the custom buttons arranged in the custom button region.

C4. The endoscope processor according to clause C3, further comprising a candidate button region display unit that displays a candidate button region where the plurality of custom buttons are arranged in an array, wherein one of the plurality of custom buttons having been dragged and dropped from the candidate button region to the custom button region is arranged in the custom button region.

C5. The endoscope processor according to any one of clauses C1 to C4, further comprising an arrangement order change acceptance unit that accepts a change of an arrangement order of the custom buttons displayed in the custom button region.

C6. The endoscope processor according to any one of clauses C1 to C5, wherein the custom buttons within the custom button region are aligned along a side of the touch panel.

C7. The endoscope processor according to any one of clauses C1 to C6, wherein the custom buttons within the custom button region are scrolled if a sliding operation is accepted in an alignment direction of the custom buttons in the custom button region.

C8. The endoscope processor according to any one of clauses C1 to C7, wherein each of the custom buttons has a function description section describing a function operable by a user and a state section indicating a state of the function.

C9. The endoscope processor according to any one of clauses C1 to C8, further comprising:
an operation acceptance unit that accepts an operation performed on any one of the custom buttons; and
a change control unit that changes an operating state of the function based on an operation accepted by the operation acceptance unit.

C10. The endoscope processor according to any one of clauses C1 to C9, further comprising:
a setting region display unit that displays on the touch panel a setting region where an on-off switch accepting switching between an on state and an off state of a function of an endoscope is combined with an adjustment switch accepting adjustment of a level of the function together with the custom button region;
a second operation acceptance unit that accepts operations performed on the on-off switch and the adjustment switch; and
a second change control unit that changes an operating state of the function based on an accepted operation.

C11. A program causing a computer to execute the processing of displaying on a touch panel a custom button region where a plurality of custom buttons respectively associated with functions operable by a user are aligned.

C12. An information processing method causing a computer to execute the processing of displaying on a touch panel a custom button region where a plurality of custom buttons respectively associated with functions operable by a user are aligned.

D1. An endoscope processor comprising:
an operation screen display unit that displays an operation screen accepting an operation by a user on a touch panel;
an acceptance stop unit that stops acceptance of an operation via the operation screen if the touch panel accepts a swipe operation; and
an acceptance restart unit that restarts acceptance of an operation via the operation screen.

D2. The endoscope processor according to clause D1, wherein display of the operation screen is changed while the touch panel accepts a swipe operation.

D3. The endoscope processor according to clause D1 or D2, further comprising a lock icon display unit that displays on the touch panel a lock icon indicating that acceptance of an operation is being stopped.

D4. The endoscope processor according to clause D3, wherein the lock icon is arranged at a peripheral edge of the operation screen.

D5. The endoscope processor according to clause D1, further comprising:
a lock icon display unit that changes display of the operation screen while the touch panel accepts the swipe operation and displays an icon to follow a portion on which the swipe operation is performed, and displays a lock icon indicating that acceptance of an operation is being stopped at a central portion of the operation screen if acceptance of the swipe operation is completed.

D6. The endoscope processor according to clause D5, wherein the icon is the lock icon.

D7. The endoscope processor according to any one of clauses D3 to D6, wherein
acceptance of an operation is restarted if a selection of the lock icon is accepted for a consecutive predetermined time period.

D8. The endoscope processor according to any one of clauses D3 to D7, wherein display of the lock icon is changed while selection of the lock icon is consecutively accepted.

D9. The endoscope processor according to any one of clauses D3 to D8, wherein acceptance of an operation is stopped if a swipe operation from up to bottom of the touch panel is accepted.

D10. The endoscope processor according to any one of clauses D1 to D9, further comprising a voice stop instruction acceptance unit that accepts an instruction of stopping acceptance of an operation via the operation screen by voice.

D11. The endoscope processor according to any one of clauses D1 to D10, further comprising a voice restart instruction acceptance unit that accepts an instruction of restarting acceptance of an operation via the operation screen by voice.

D12. A program causing a computer to execute the processing of:
displaying an operation screen accepting an operation by a user on a touch panel;
stopping acceptance of an operation via the operation screen displayed if the touch panel accepts a swipe operation; and
restarting acceptance of an operation via the operation screen if a predetermined operation is accepted.

D13. An information processing method causing a computer to execute the processing of:
displaying an operation screen accepting an operation by a user on a touch panel;
stopping acceptance of an operation via the operation screen displayed if the touch panel accepts a swipe operation; and
restarting acceptance of an operation via the operation screen if a predetermined operation is accepted.

10 endoscope system
15 keyboard
16 storage rack
17 foot switch
18 camera
20 endoscope processor
21 control unit
22 main storage
23 auxiliary storage
24 communication unit
25 touch panel
251 display unit
252 input unit
259 display area frame 26 display device I/F
27 input device I/F
28 reading part
31 endoscope connector
311 electric connector
312 optical connector
33 light source
34 pump
35 water supply tank
36 air/water supply port
40 endoscope
43 operation part
431 control button
433 bending knob
44 insertion part
441 flexible portion
442 bending portion
443 head portion
45 bending proof portion
48 scope connector
49 universal cord
50 display device
51 menu region
511 scope eject button
512 profile button
513 patient button
514 white balance button
515 setting button
52 operation region
521 pump setting region (setting region)
522 pump switch (on-off switch)
523 pump adjustment switch (adjustment switch)
524 pump level section
525 lamp life section
526 lamp setting region (setting region)
527 lamp switch (on-off switch)
528 lamp adjustment switch (adjustment switch)
529 lamp level section
54 custom button region
541 custom button
542 custom region setting button
543 candidate button region
544 insertion marker
545 function description section
547 state section
548 icon section
549 name section
55 setting tab (second tab, second button)
551 select tab (first tab, first button)
552 image tab
553 function tab
554 system tab
555 home button
556 add button
557 lock button
558 delete button
559 option button
561 top screen (operation screen)
562 patient list screen
563 registration/editing screen
564 profile list screen
565 registration/editing screen
566 setting screen
567 select menu setting screen
568 custom button region editing screen
571 advance button
572 option button
573 sort button
574 close button
578 setting option button
579 setting display section
581 function icon
582 control button icon
583 foot switch icon
61 endoscopic image section
62 date and time section
63 stopwatch section
64 patient section
641 patient name section
642 patient ID section
643 patient age section
644 patient sex section
645 comment section
65 doctor section
661 patient ID entry section
662 patient name entry section
663 patient sex entry section
664 patient birthday entry section
665 patient age section
666 note section
668 cancel button
669 save button
71 profile DB
72 patient DB
81 setting area display unit
82 operation acceptance unit
83 change control unit
90 computer
96 portable recording medium
97 program
98 semiconductor memory

What is claimed is:

1. An endoscope processor, comprising:
a processor executing program code to perform:
displaying, by the processor, on a touch panel a setting region where an on-off switch accepting switching between an on state and an off state of a function of an endoscope is combined with an adjustment switch accepting adjustment of a level of the function;
accepting, by the processor, operations performed on the on-off switch and the adjustment switch that are displayed; and
changing, by the processor, an operating state of the function based on an accepted operation, wherein
the adjustment switch includes a track indicating an adjustable range and a slider portion movable along the track,
the accepting operation accepts a tap operation performed around the track at a position outside and spaced from the track, and
the processor also executing program code to move a position of the slider portion by a predetermined amount causing a predetermined amount of change in the level of the function of the endoscope in response to the tap operation performed at a location outside and spaced from the track.

* * * * *